(12) United States Patent
Ishibashi et al.

(10) Patent No.: US 7,255,935 B2
(45) Date of Patent: *Aug. 14, 2007

(54) ORGANIC ELECTROLUMINESCENT ELEMENT AND LUMINESCENT APPARATUS EMPLOYING THE SAME

(75) Inventors: Tadashi Ishibashi, Kanagawa (JP); Mari Ichimura, Kanagawa (JP); Naoyuki Ueda, Kanagawa (JP); Shinichiro Tamura, Kanagawa (JP)

(73) Assignee: Sony Corporation, Tokyo (JP)

( * ) Notice: Subject to any disclaimer, the term of this patent is extended or adjusted under 35 U.S.C. 154(b) by 575 days.

This patent is subject to a terminal disclaimer.

(21) Appl. No.: 10/009,021

(22) PCT Filed: Apr. 9, 2001

(86) PCT No.: PCT/JP01/03051

§ 371 (c)(1),
(2), (4) Date: Mar. 19, 2002

(87) PCT Pub. No.: WO01/77253

PCT Pub. Date: Oct. 18, 2001

(65) Prior Publication Data

US 2002/0106530 A1 Aug. 8, 2002

(30) Foreign Application Priority Data

Apr. 7, 2000 (JP) .............................. 2000-106430

(51) Int. Cl.
*H01J 1/62* (2006.01)

(52) U.S. Cl. ...................... 428/690; 428/917; 313/504; 313/506

(58) Field of Classification Search ................ 428/690, 428/917; 257/40, E51.04; 250/301.16; 313/504, 313/506, 509
See application file for complete search history.

(56) References Cited

U.S. PATENT DOCUMENTS 5,281,489 A * 1/1994 Mori et al. .................. 428/690

(Continued)

FOREIGN PATENT DOCUMENTS

EP 0388768 9/1990

(Continued)

*Primary Examiner*—Rena Dye
*Assistant Examiner*—Camie S. Thompson
(74) *Attorney, Agent, or Firm*—Sonnenschein Nath & Rosenthal LLP

(57) ABSTRACT

This invention provides an organic electroluminescent element which emits red light with high color purity, high luminance, and high reliability, owing to the compound used therein which has high fluorescence yields and good thermal stability. The organic electroluminescent element which is made up of a glass substrate (1), an ITO transparent electrode (2), a hole transfer layer (6), an electron transfer layer (7), and a metal electrode (3) (which are laminated in the order mentioned), with the hole transfer layer (6) and/or the electron transfer layer (7) being formed of a mixture containing at least one species of the aminostyryl compound represented by the following general formula [I], and a hole blocking layer (30) is interposed between the hole transfer layer (6) and the electron transfer layer (7).

$$Y^1\text{—CH}\!=\!\text{CH—}X^1\text{—CH}\!=\!\text{CH—}Y^2 \quad \text{General formula [I]}$$

[where, in the general formula [I] above, $X^1$ denotes any aryl group such as a phenyl group having a substituent groups such as a nitro group, and $Y^1$ and $Y^2$ each is a group having an aminophenyl group in the skeleton.]

17 Claims, 5 Drawing Sheets

U.S. PATENT DOCUMENTS

| | | |
|---|---|---|
| 6,228,514 B1 | 5/2001 | Tadashi et al. ............. 428/690 |
| 6,265,088 B1 * | 7/2001 | Tadashi et al. ............. 428/690 |
| 6,492,557 B1 * | 12/2002 | Ichimura et al. ............ 564/434 |
| 6,525,212 B1 * | 2/2003 | Ichimura et al. ............ 558/418 |
| 6,633,122 B2 * | 10/2003 | Kijima et al. ................ 313/506 |
| 6,660,411 B2 * | 12/2003 | Sato et al. .................. 428/690 |
| 2001/0033945 A1 | 10/2001 | Ishibashi et al. ............ 428/690 |

FOREIGN PATENT DOCUMENTS

| | | |
|---|---|---|
| EP | 0929104 | 7/1999 |
| EP | 0954205 | 11/1999 |
| EP | 0960927 | 12/1999 |
| EP | 0967834 | 12/1999 |
| EP | 1073128 | 1/2001 |
| JP | 2247278 | 10/1990 |
| JP | 06001973 | 1/1994 |
| JP | 1 1329731 | 11/1999 |
| JP | 2000 12224 | 1/2000 |
| JP | 2000 12226 | 1/2000 |

\* cited by examiner

ORGANIC ELECTROLUMINESCENT ELEMENT AND LUMINESCENT APPARATUS EMPLOYING THE SAME

BACKGROUND OF THE INVENTION

The present invention relates to an organic electroluminescent element (organic EL element) in which an organic layer having a luminescent region is arranged between an anode and a cathode, and also to a luminescent device (such as display device) in which the organic EL element is used.

BACKGROUND ART

Active research and development works are being carried out on light-weight, high-efficiency flat panel displays for use as the screens of computers and televisions.

At present, Braun tubes (CRT) are most commonly used as displays because of their high brightness and good color reproducibility. On the other hand, they suffer the disadvantage of being bulky and heavy and high in power consumption.

Although liquid-crystal displays of active matrix drive type have been commercialized as light-weight, high-efficiency flat panel displays, they have a narrow viewing angle and need back light with a large power consumption when used in a dark environment (because they do not emit light spontaneously). Moreover, they are not satisfactory in response to high-speed, high-resolution video signals, which are expected to be put to practical use in near future. Another disadvantage is difficulties in production of large-screen displays and high production cost.

An alternative to liquid crystal displays is a display with light-emitting diodes. It also suffers high production cost and presents difficulties in forming a matrix of light-emitting diodes on a single substrate. There are many problems to be solved before it is put to practical use as a low-price display which will displace Braun tubes.

These problems are expected to be solved by a new flat panel display which is attracting attention recently. It is the organic electroluminescent element (EL element) made of an organic luminescent material. Using an organic compound as the luminescent material is expected to realize a flat panel display which emits light spontaneously, has a high response speed, and has no dependence on viewing angle.

The organic electroluminescent element is composed of a transparent anode and a metal cathode, with an organic thin film interposed between them, the organic thin film containing a luminous material which emits light upon current injection. C. W. Tang, S. A. VanSlyke, et al. reported in Applied Physics Letters, vol. 51, No. 12, pp. 913-915 (1987) the development of an organic EL element of single-hetero structure in which the organic thin film is of double-layer structure consisting of a thin film of hole-transfer material and a thin film of electron-transfer material, so that the organic thin film emits light by recombination of holes and electrons injected into it from the anode and cathode, respectively.

In the element of this structure, either the hole transfer material or the electron transfer material functions also as a luminous material, and light emission takes place in the wavelength region corresponding to the energy gap at the ground state and excited state of the luminous material. The double-layer structure greatly reduces the drive voltage and improves the luminescence efficiency.

After that, C. Adachi, S. Tokita, T. Tsutsui, S. Saito, et al. reported in Japanese Journal of Applied Physics, Vol. 27, No. 2, pp. L269-L271 (1988) the development of an organic EL element of double-hetero structure having a triple-layer structure composed of hole-transfer material, luminous material, and electron transfer material. In addition, C. W. Tang, S. A. VanSlyke, and C. H. Chen, et al. reported in Journal of Applied Physics, Vol. 65, No. 9, pp. 3610-3616 (1989) the development of a new element structure in which the electron transfer material contains a luminous material. Their researches proved the feasibility of high-luminance light emission at a low voltage and advanced new developments.

The organic compound used as the luminous material is available in many kinds, and hence theoretically it will emit light of any desired color if its molecular structure is properly modified. It is easier to make an EL element with an organic compound than with an inorganic thin film, because an organic compound with proper molecular design produces high-purity three colors (red, green, and blue) necessary for the full-color display.

However, actual organic EL elements have many problems to be solved. It is difficult to develop an element capable of emitting red light stably with high luminance. It has been reported that red light is obtained from an electron transfer material which is tris (8-quinolinol) aluminum (Alq3 for short hereinafter) doped with DCM [4-dicyanomethylene-6-(p-dimethylaminostyryl)-2-methyl-4H-pyran]. (Chem. Funct. Dyes, Proc. Int. Symp., 2nd P. 536 (1993)) Unfortunately, it is not satisfactory in brightness and reliability for use as the display material.

T. Tsutsumi and D. U. Kim reported in Conference of Inorganic and Organic Electroluminescence (1996, Berlin) BSB-BCN. It gave a luminance higher than 1000 $cd/m^2$ but it is still unsatisfactory in chromaticity of red for full color.

At present, there is a demand for a luminous element capable of stably emitting red light with a higher luminance and a higher color purity.

There was proposed in Japanese Patent Laid-open No. 188649/1995 (Japanese Patent Application No. 148798/1994) a specific distyryl compound for use as an organic electroluminescent material. This compound is intended for blue color emission, not for red color emission.

SUMMARY OF THE INVENTION

It is an object of the present invention to provide an organic electroluminescent element which stably emits red light having high luminance and good color purity with the aid of a compound having high fluorescence yields and good thermostability.

It is another object of the present invention to provide an organic electroluminescent element containing a compound which inherently has high quantum yields, the element being so designed as to promote recombination of holes and electrons in the luminous layer, thereby permitting high-luminance, high-efficiency light emission.

In order to address the above-mentioned problems, the present inventors carried out extensive studies, which led to the finding that it is possible to provide an organic electroluminescent element emitting red light with high luminance and high reliability if it has the light-emitting region composed of a specific aminostyryl compound and a material capable of transmitting energy efficiently to the compound.

The present invention is directed to an organic electroluminescent element (occasionally referred to as the first organic EL element of the present invention hereinafter) in which an organic layer having a luminescent region is arranged between an anode and a cathode and an organic substance which emits light upon current injection is contained as a constituent, characterized in that said organic layer is constructed of at least one layer formed from a mixture containing at least one species of the aminostyryl compounds represented by the following general formula [I].

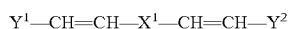   General formula [I]

[where, in the general formula [I] above, $X^1$ denotes any of the following general formulas (1) to (7)

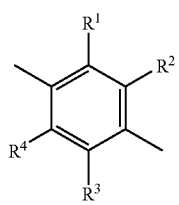 (1)

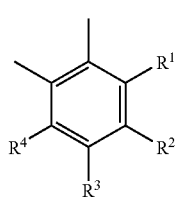 (2)

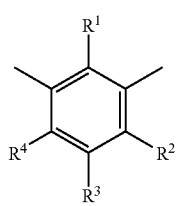 (3)

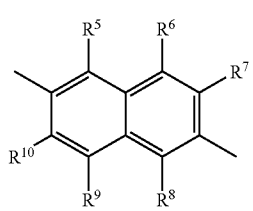 (4)

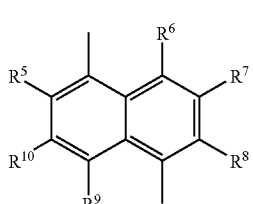 (5)

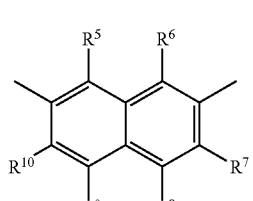 (6)

-continued

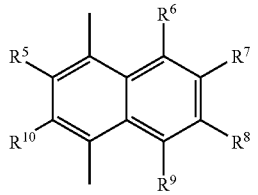 (7)

(where, in the general formulas (1) to (3) above, at least one (for example, one or two) of $R^1$ $R^4$ is a group selected from halogen atoms (such as fluorine atoms, chlorine atoms, and bromine atoms, the same shall apply hereinafter), nitro groups, cyano groups, and fluoroalkyl groups (such as trifluoromethyl group, the same shall apply hereinafter), and others are groups selected from hydrogen atom, alkyl groups, aryl groups, alkoxyl groups, halogen atoms, nitro groups, cyano groups, and fluoroalkyl groups, which are identical or different; in the general formulas (4) to (7), at least one (for example, one or two) of $R^5$ to $R^{10}$ is a group selected from halogen atoms, nitro groups, cyano groups, and fluoroalkyl groups, and others are groups selected from hydrogen atom, alkyl groups, aryl groups, alkoxyl groups, halogen atoms, nitro groups, cyano groups, and fluoroalkyl groups, which are identical or different.) $Y^1$ is a group represented by the following general formula (8) or (9), and $Y^2$ is a group represented by the following general formula (8), (9), or (10).

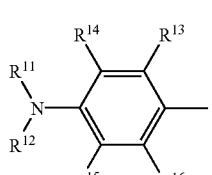 (8)

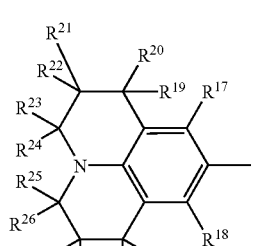 (9)

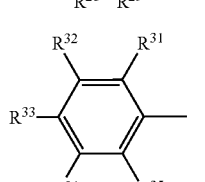 (10)

(where, in the general formulas (8) to (10) above, $R^{11}$ and $R^{12}$ each is a group selected from a hydrogen atom, alkyl groups with optional substituents, and aryl groups with optional substituents, which are identical or different; and $R^{13}$ to $R^{35}$ each is a group selected from a hydrogen atom, alkyl groups with optional substituents, and aryl groups with optional substituents, alkoxyl groups with optional substituents, halogen atoms, nitro groups, cyano groups, and fluoroalkyl groups, which are identical or different.)

In the general formula [I] above, $X^1$ is a group represented by any one of the following structural formulas (11) to (14)

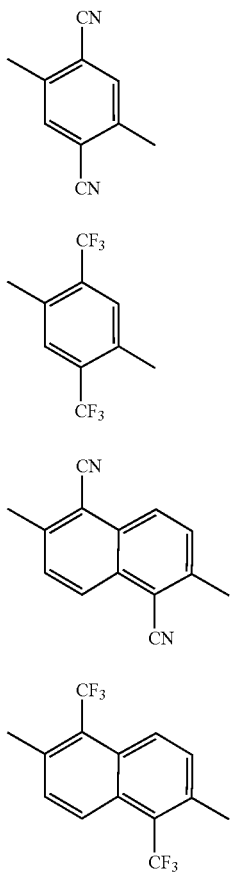

and $Y^1$ and $Y^2$ each may be a group represented by the following general formula (8) or (9). (the same shall apply hereinafter)

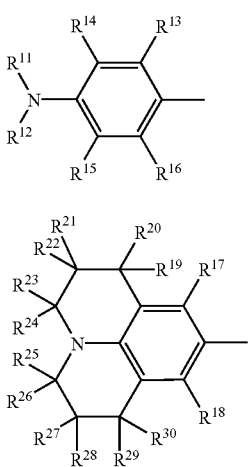

(where, in the general formulas (8) and (9) above, $R^{11}$ and $R^{12}$ are defined as above, $R^{13}$ to $R^{30}$ are defined as above (or a trifluoromethyl group if defined as fluoroalkyl groups).

In the first organic EL element of the present invention, the organic layer may be of organic multilayer structure composed of a hole transfer layer and an electron transfer layer, with at least the electron transfer layer in the organic multilayer structure being the layer of a mixture containing at least one species of the aminostyryl compounds represented by the general formula [I] above.

The organic layer may be of organic multilayer structure composed of a hole transfer layer and an electron transfer layer, with at least the hole transfer layer in the organic multilayer structure being the layer of a mixture containing at least one species of the aminostyryl compounds represented by the general formula [I] above.

The organic layer may be of organic multilayer structure composed of a hole transfer layer and an electron transfer layer, with the hole transfer layer being a layer of a mixture containing at least one species of the aminostyryl compounds represented by the general formula [I] above, and the electron transfer layer being the layer of a mixture containing at least one species of the aminostyryl compounds represented by the general formula [I] above.

The organic layer may be of organic multilayer structure composed of a hole transfer layer, a luminescent layer, and an electron transfer layer, with at least the luminescent layer in the organic multilayer structure being the layer of a mixture containing at least one species of the aminostyryl compounds represented by the general formula [I] above.

In the present invention, the material that can be used to form the mixture layer containing the aminostyryl compound include, in addition to the aminostyryl compound, hole transfer materials (such as aromatic amines), electron transfer materials (such as $Alq_3$ and pyrazoline), and a series of compounds generally used as a dopant for red light emission (such as DCM and its analogous compounds, porphylins, phthalocyanines, perylene compounds, Nile red, and squarilium compounds). The same shall apply hereinafter.

In the case where at least one species of the above-mentioned aminostyryl compounds is mixed with other compounds in the mixture layer, its amount is 0.1-95% (by weight) and the content of dopant may be determined within this range. (The same shall apply hereinafter.)

"Mixture layer" as used herein typically means a layer of a mixture of the above-mentioned aminostyryl compound and other compounds. It also means a layer of a mixture of two or more aminostyryl compounds included in the above-mentioned aminostyryl compounds. Such a mixture layer emits red light with desired luminance and chromaticity according to the combination of a plurality of compounds.

The organic electroluminescent element of the present invention is suitable for a light-emitting device which is constructed for use as a display device. (The same shall apply hereinafter.)

The present invention is also directed to an organic electroluminescent element (occasionally referred to as the second organic EL element of the present invention hereinafter) in which an organic layer having a luminescent region is arranged between an anode and a cathode, characterized in that said organic layer is constructed of at least one layer formed from a mixture containing at least one species (one, two or more species) of the aminostyryl compounds represented by the following structural formulas (15)-1 to (15)-12, (16)-1 to (16)-12, (17)-1 to (17)-6, and (18)-1 to (18)-6.

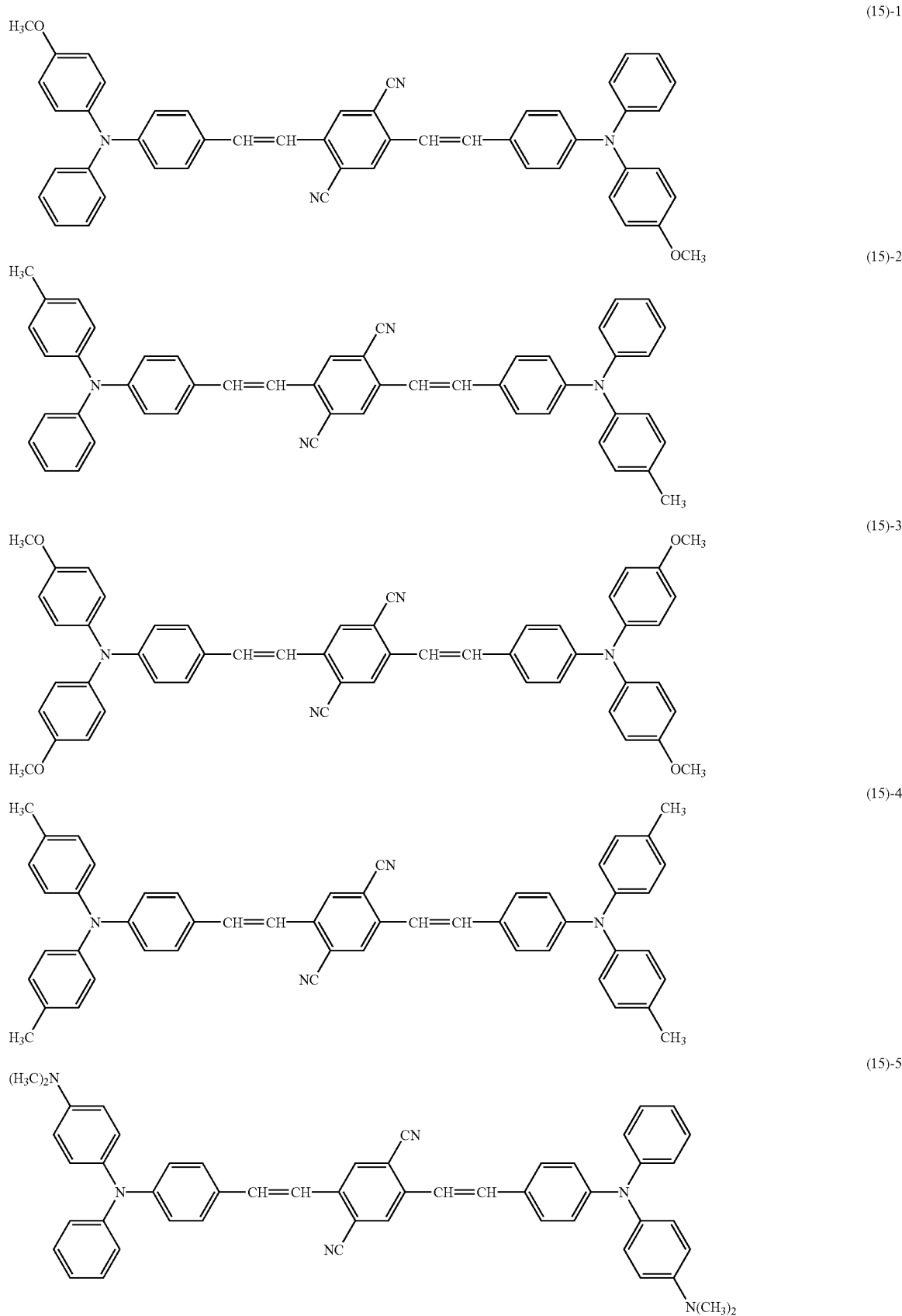

-continued
(15)-6
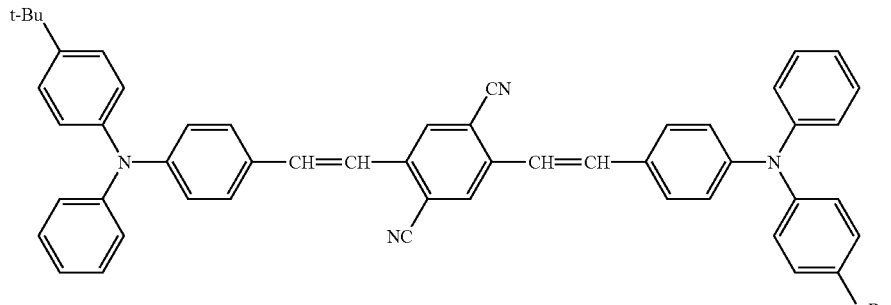
(15)-7
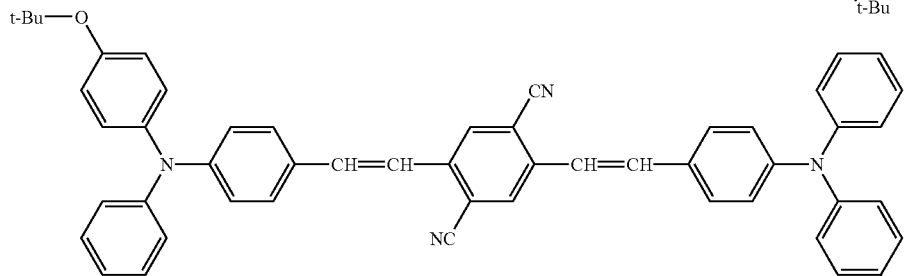
(15)-8
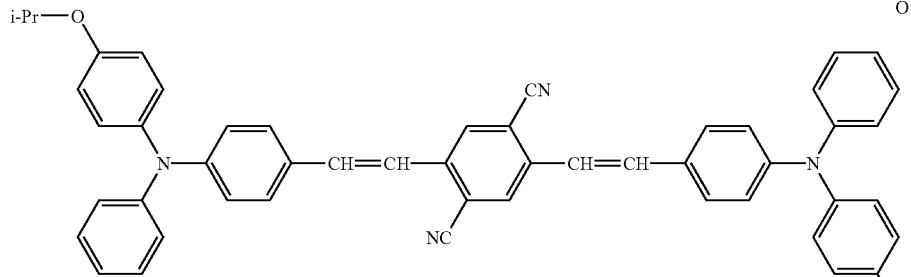
(15)-9
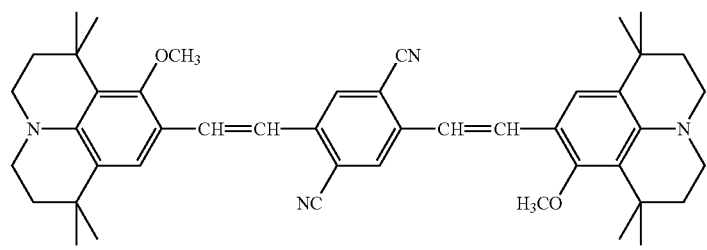
(15)-10
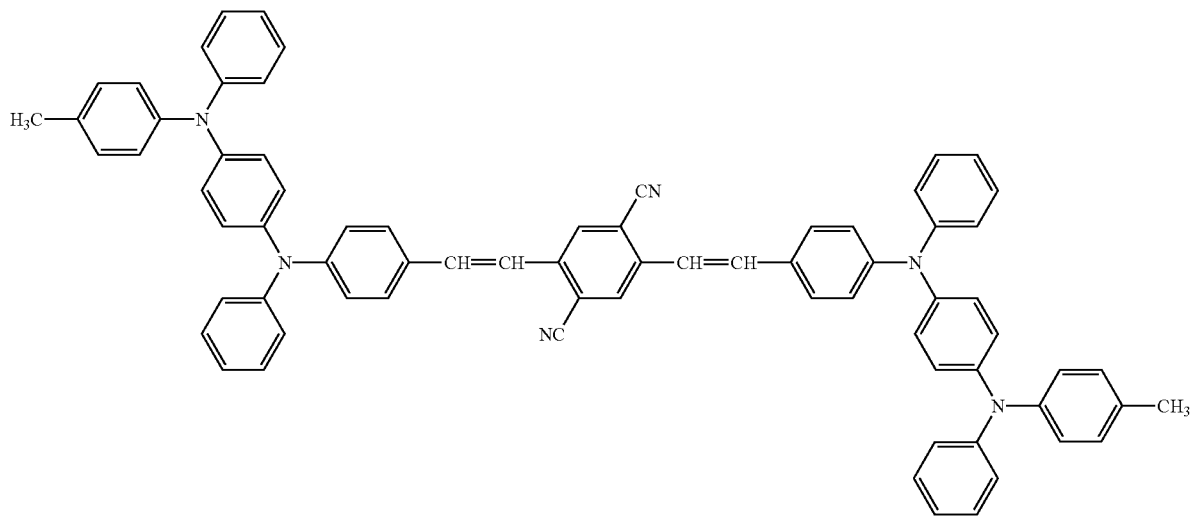

-continued
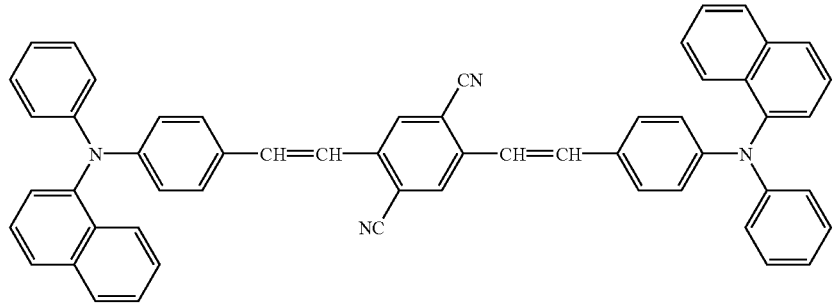
(15)-11
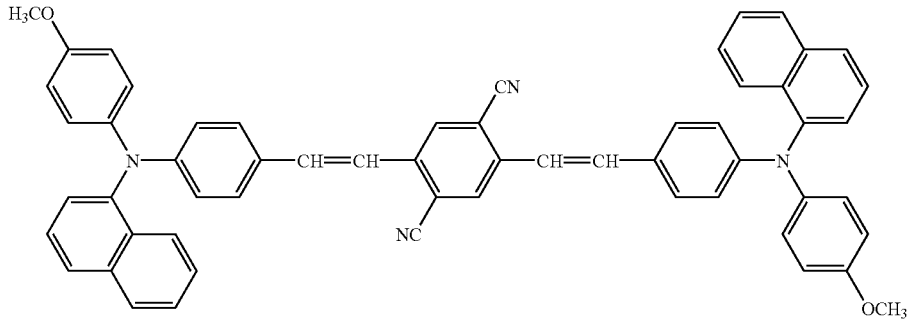
(15)-12
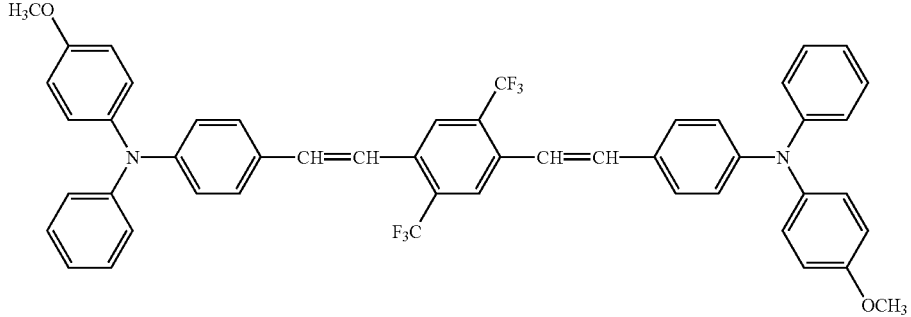
(16)-1
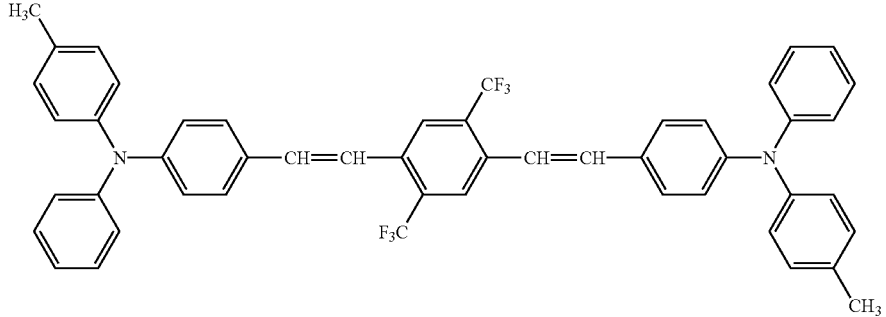
(16)-2
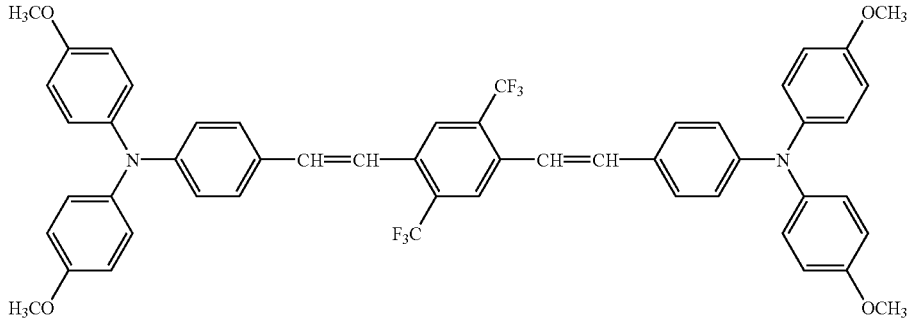
(16)-3

-continued
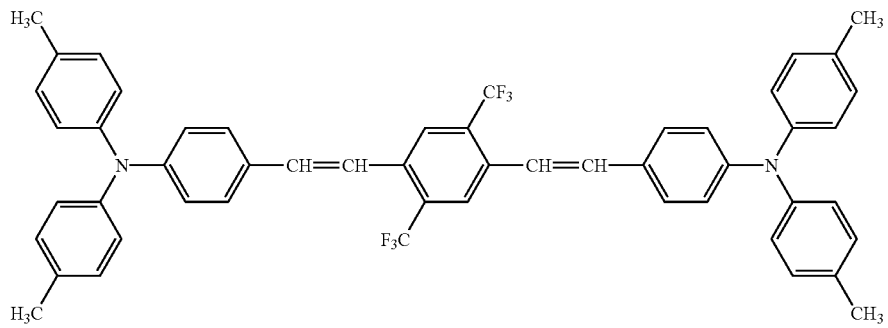
(16)-4
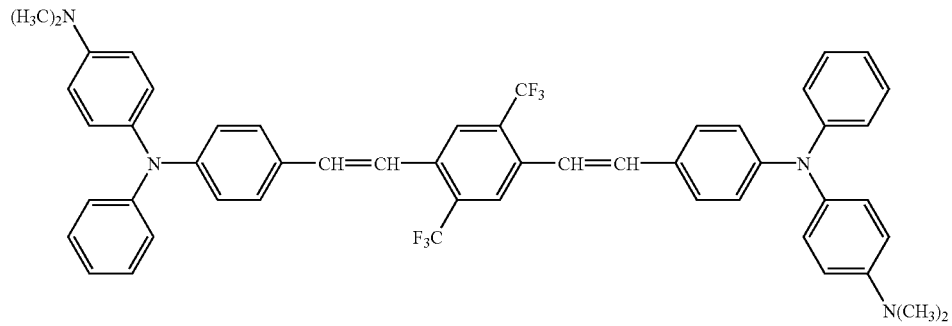
(16)-5
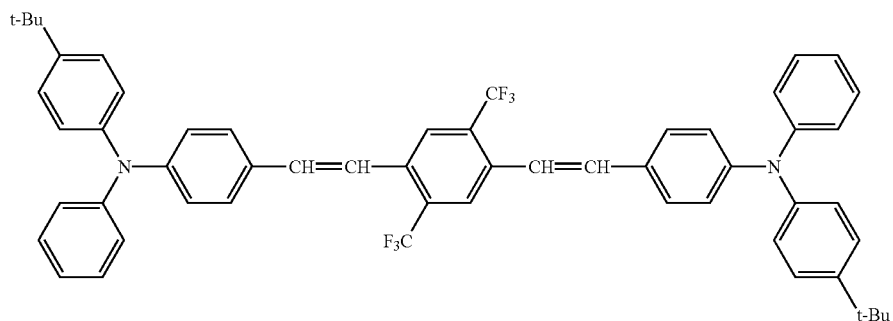
(16)-6
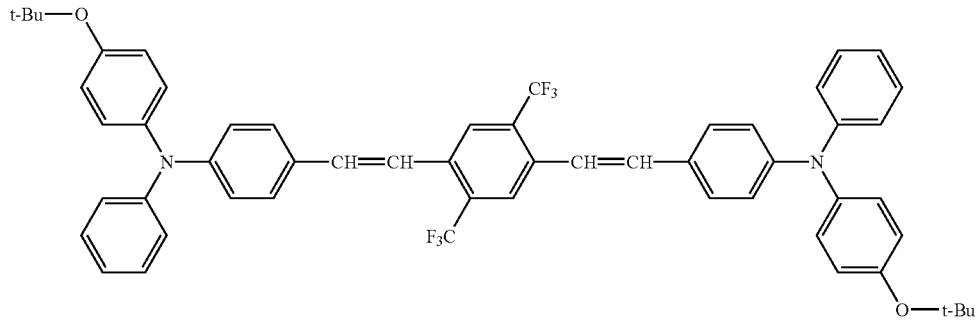
(16)-7
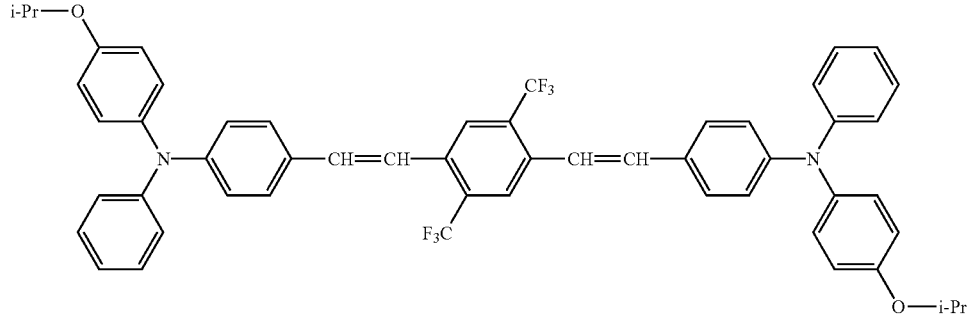
(16)-8

-continued
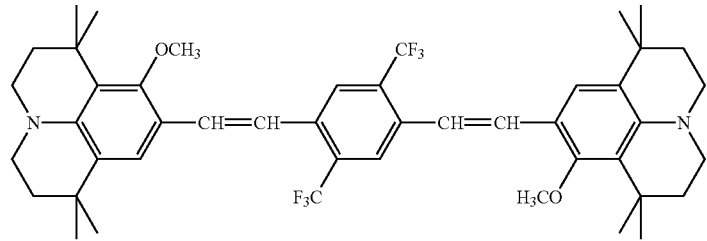
(16)-9
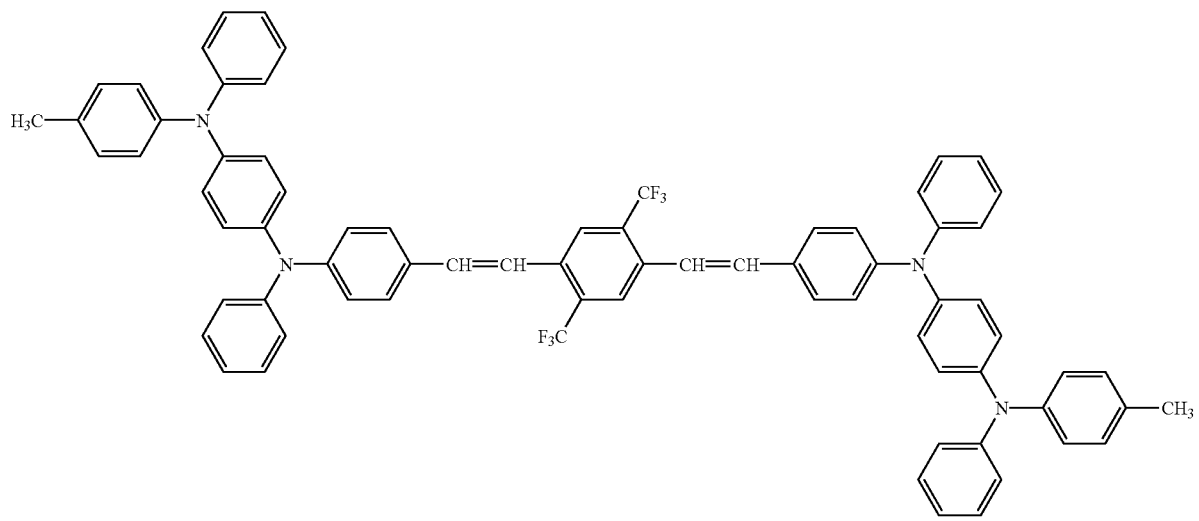
(16)-10
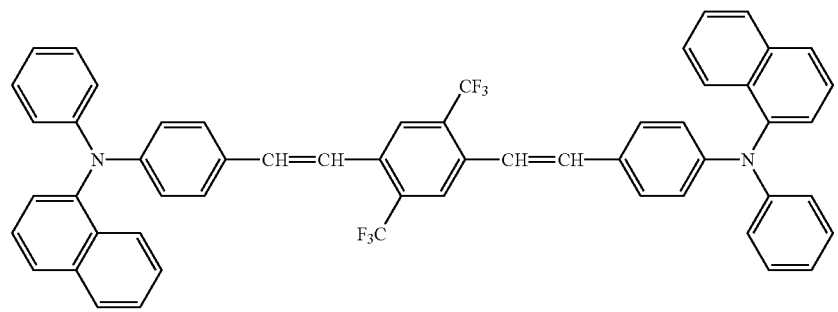
(16)-11
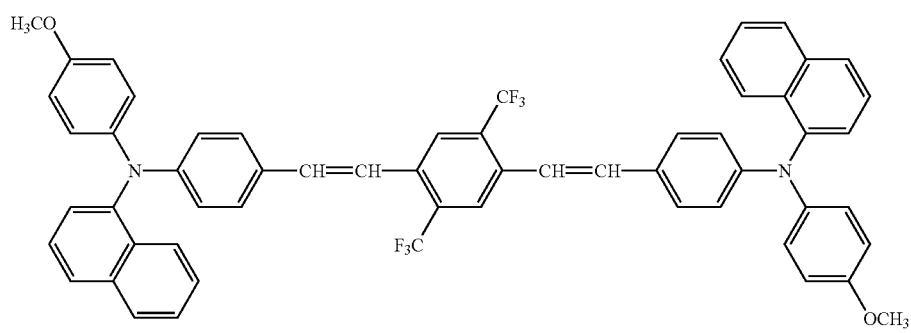
(16)-12

-continued
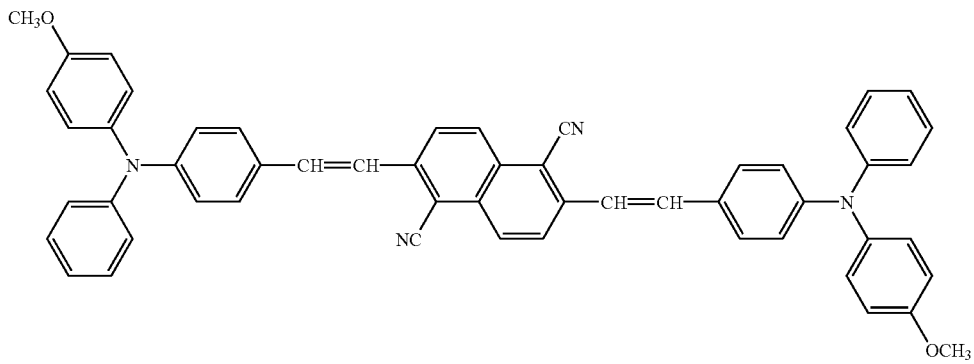
(17)-1
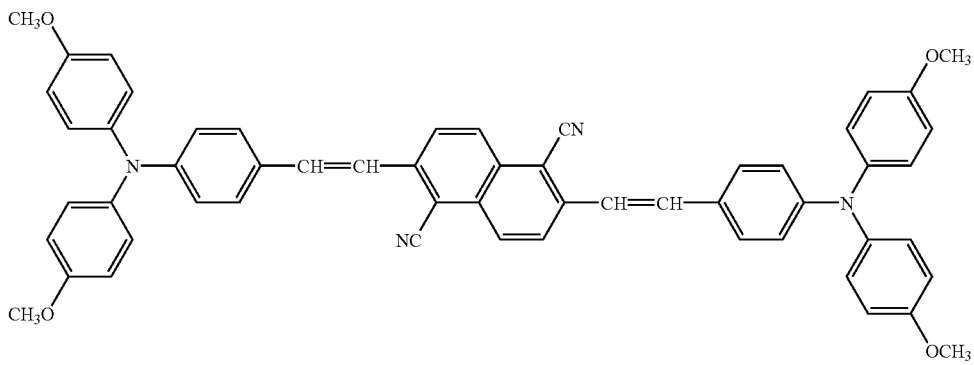
(17)-2
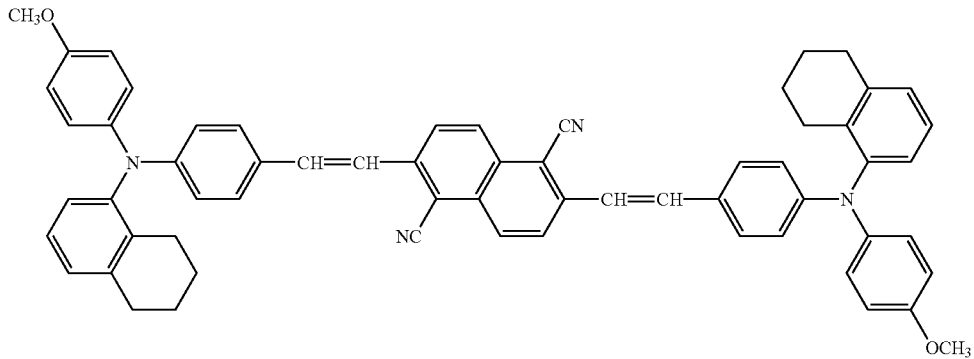
(17)-3
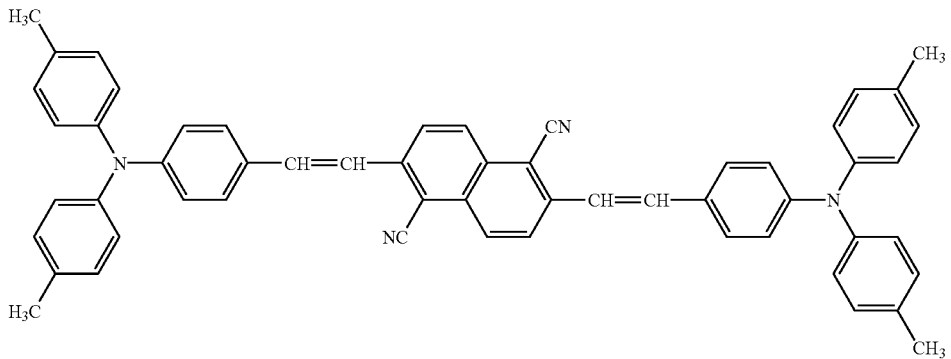
(17)-4

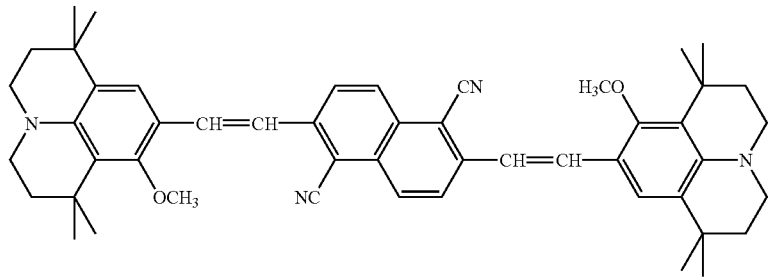
(17)-5
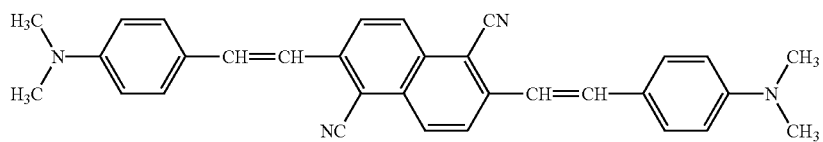
(17)-6
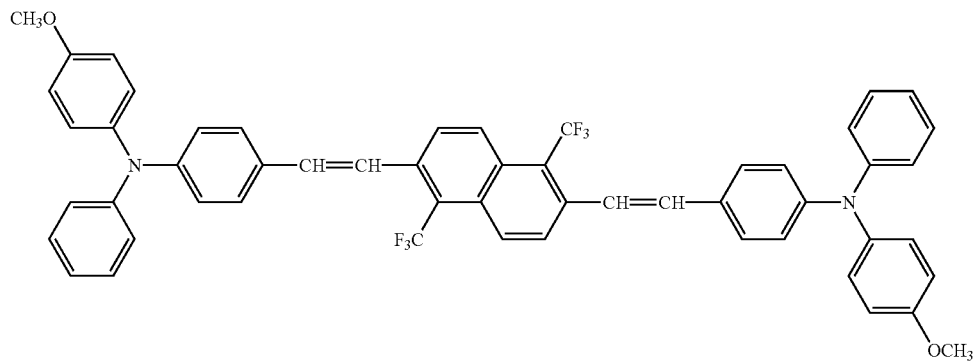
(18)-1
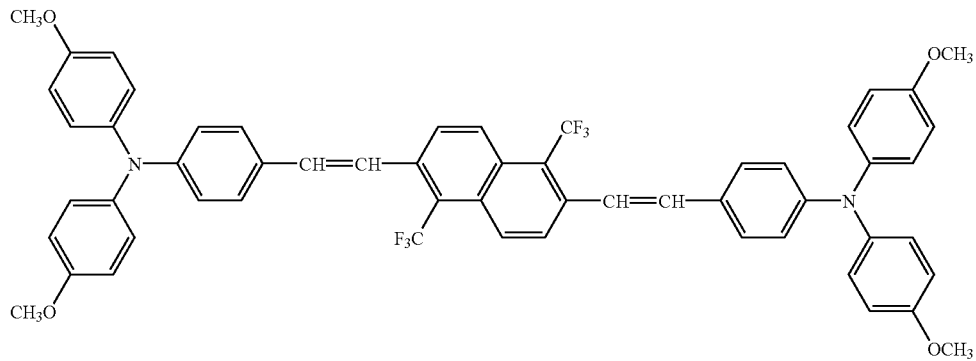
(18)-2
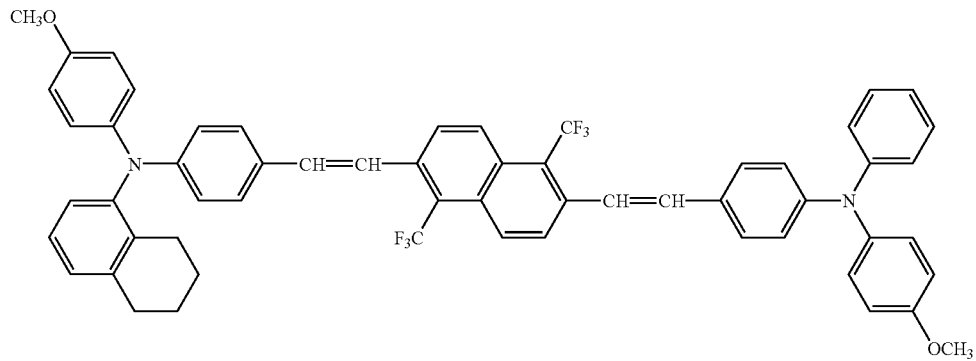
(18)-3

-continued (18)-4

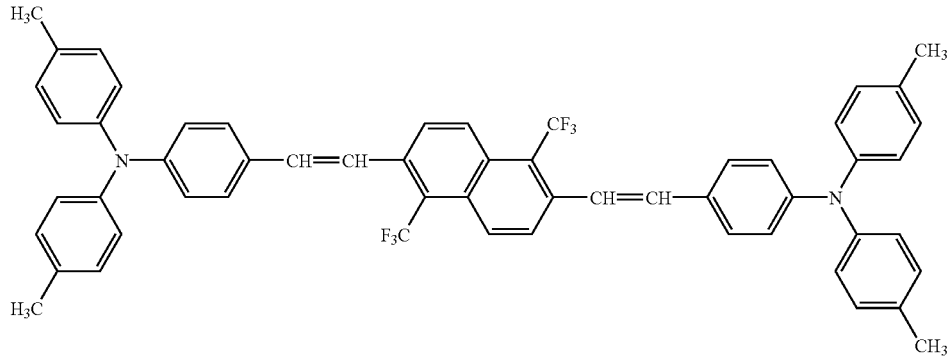

(18)-5

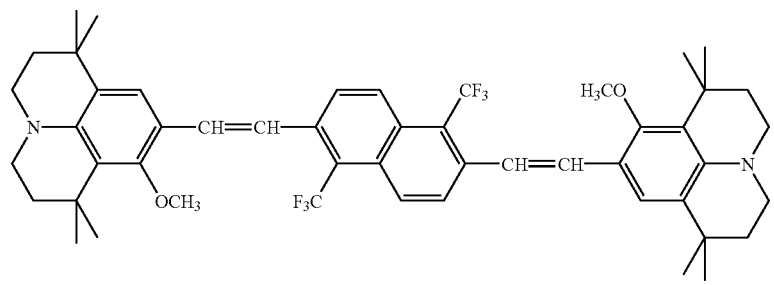

(18)-6

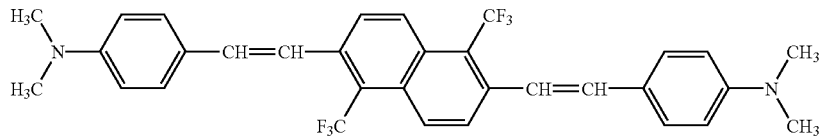

In the second organic EL element of the present invention, the organic layer may be of organic multilayer structure composed of a hole transfer layer and an electron transfer layer, with at least the electron transfer layer in the organic multilayer structure being the layer of a mixture containing at least one species of the aminostyryl compounds.

The organic layer may be of organic multilayer structure composed of a hole transfer layer and an electron transfer layer, with at least the hole transfer layer in the organic multilayer structure being the layer of a mixture containing at least one species of the aminostyryl compounds.

The organic layer may be of organic multilayer structure composed of a hole transfer layer and an electron transfer layer, with the hole transfer layer being a layer of a mixture containing at least one species of the aminostyryl compounds mentioned above, and the electron transfer layer being the layer of a mixture containing at least one species of the aminostyryl compounds.

The organic layer may be of organic multilayer structure composed of a hole transfer layer, a luminescent layer, and an electron transfer layer, with at least the luminescent layer in the organic multilayer structure being the layer of a mixture containing at least one species of the aminostyryl compounds.

The organic layer may be constructed such that at least one layer therein is a layer of a mixture containing at least one species of the aminostyryl compounds and a dye emitting red light which has the emission maximum in a range of 600 nm or more (for example, 600-700 nm, the same shall apply hereinafter).

In this case, the organic layer may be of organic multilayer structure composed of a hole transfer layer and an electron transfer layer, with said at least one layer in the laminate structure being the electron transfer layer.

Also, the organic layer may be of organic multilayer structure composed of a hole transfer layer and an electron transfer layer, with said at least one layer in the laminate structure being the hole transfer layer.

Also, the organic layer may be of organic multilayer structure composed of a hole transfer layer and an electron transfer layer, with the hole transfer layer being a layer of a mixture containing at least one species of the aminostyryl compounds and a dye emitting red light which has the emission maximum in a range of 600 nm or more, and the electron transfer layer being the layer of a mixture containing at least one species of the aminostyryl compounds and a dye emitting red light which has the emission maximum in a range of 600 nm or more.

Also, the organic layer may be of organic multilayer structure composed of a hole transfer layer, a luminescent layer, and an electron transfer layer, with the luminescent layer being the layer of a mixture containing at least one species of the aminostyryl compounds and a dye emitting red light which has the emission maximum in a range of 600 nm or more.

The present invention is also directed to an organic electroluminescent element (occasionally referred to as the third organic EL element of the present invention hereinafter) in which an organic layer having a luminescent region is arranged between an anode and a cathode, characterized in that said organic layer is constructed of at least one layer formed from a light-emitting mixture containing at least one species (one, two, or more species) of the aminostyryl compounds represented by the general formula [I] above and there exists a hole blocking layer adjacent to (particularly in contact with) the cathode of the layer formed from a light-emitting mixture.

In the third organic EL element of the present invention, the organic layer may be of organic multilayer structure composed of a hole transfer layer and an electron transfer layer, with at least the electron transfer layer in the organic multilayer structure being the layer of a mixture containing at least one species of the aminostyryl compounds represented by the general formula [I] above.

Also, the organic layer may be of organic multilayer structure composed of a hole transfer layer and an electron transfer layer, with at least the hole transfer layer in the organic multilayer structure being the layer of a mixture containing at least one species of the aminostyryl compounds represented by the general formula [I]above.

Also, the organic layer may be of organic multilayer structure composed of a hole transfer layer and an electron transfer layer, with the hole transfer layer being the layer of a light-emitting mixture containing at least one species of the aminostyryl compounds represented by the general formula [I] above, and the electron transfer layer being the layer of a light-emitting mixture containing at least one species of the aminostyryl compounds represented by the general formula [I] above, and there exists a hole blocking layer adjacent to the cathode of the layer formed from a light-emitting mixture capable of electron transfer.

The organic layer may be of organic multilayer structure composed of a hole transfer layer, a luminescent layer, and an electron transfer layer, with at least the luminescent layer in the organic multilayer structure being the layer of a light-emitting mixture containing at least one species of the aminostyryl compounds represented by the general formula [I] above.

In the third organic EL element of the present invention, the hole blocking layer should be one which promotes the recombination of holes and electrons in the luminescent layer, thereby efficiently emitting light with high luminance. The material suitable for such a hole blocking layer should preferably be one which has the following energy state. (The same shall apply hereinafter.) That is, the highest occupied molecular orbital level of the material forming the hole blocking layer is at a lower energy level than the highest occupied molecular orbital level of the material forming the layer in contact with the anode of the hole blocking layer. Besides, the lowest unoccupied molecular orbital level of the material forming the hole blocking layer is at a higher energy level than the lowest unoccupied molecular orbital level of the material forming the layer in contact with the anode of the hole blocking layer and is also at a lower energy level than the lowest unoccupied molecular orbital level of material forming the layer in contact with the cathode of the hole blocking layer.

Such materials include those phenanthroline derivatives which are disclosed in Japanese Patent Laid-open Nos. 79297/1998, 204258/1999, 204264/1999, and 204259/1999. They are not restricted to phenanthroline derivatives so long as they meet the above-mentioned condition of energy level. Those phenanthroline derivatives which can be used are shown below.

General formula of phenanthroline derivatives:

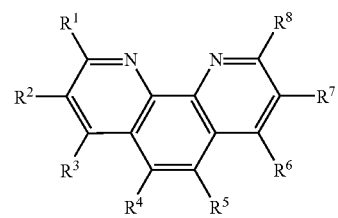

(where, in the general formula above, $R^1$ to $R^8$ each denotes a hydrogen atom, substituted or unsubstituted alkyl group, substituted or unsubstituted aryl group, substituted or unsubstituted amino group, halogen atom, cyano group, or hydroxyl group.)

Structural formula 1:

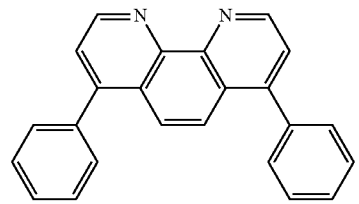

Structural formula 2:

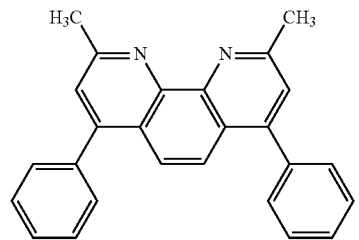

Structural formula 3:

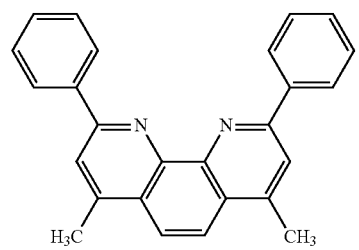

Structural formula 4:

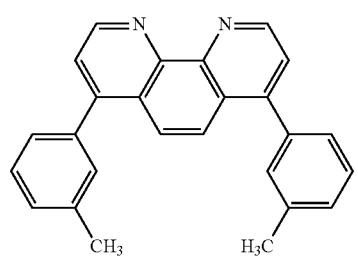

Structural formula 5:

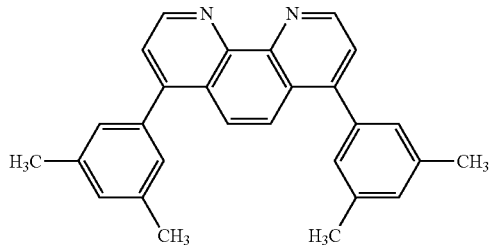

Structural formula 6:

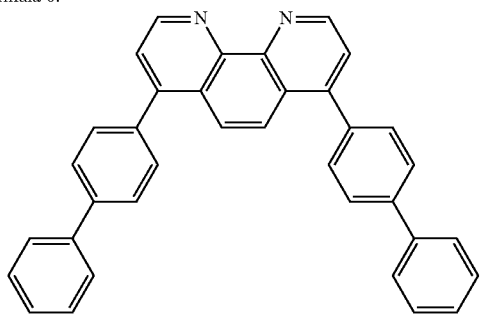

Structural formula 7:

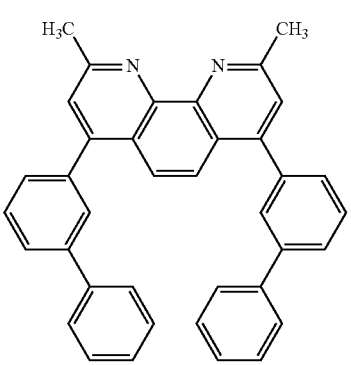

Structural formula 8:

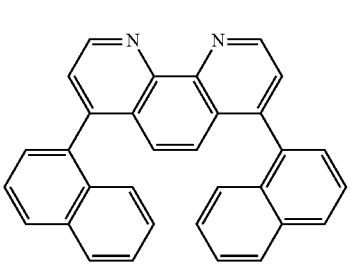

Structural formula 9:

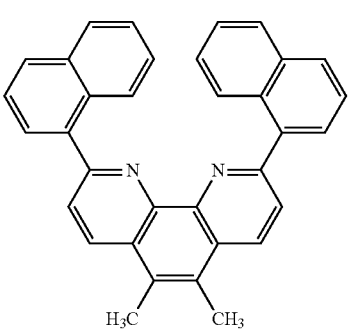

Structural formula 10:

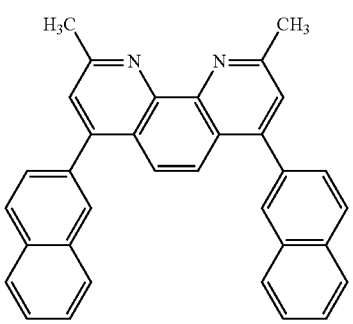

The present invention is directed to an organic electroluminescent element (occasionally referred to as the fourth organic EL element hereinafter) in which an organic layer having a luminescent region is arranged between an anode and a cathode, characterized in that said organic layer is constructed of at least one layer formed from a mixture containing at least one species (one, two, or more) of the aminostyryl compounds represented by the above-mentioned. structural formulas (15)-1 to (15)-12, (16)-1 to (16)-12, (17)-1 to (17)-6, and (18)-1 to (18)-6 and there exists a hole blocking layer adjacent to the cathode of the layer formed from a light-emitting mixture.

In the fourth organic EL element, the organic layer may be of organic multilayer structure composed of a hole transfer layer and an electron transfer layer, with at least the electron transfer layer in the organic multilayer structure being the layer of a light-emitting mixture containing at least one species of the aminostyryl compounds.

Also, the organic layer may be of organic multilayer structure composed of a hole transfer layer and an electron transfer layer, with at least the hole transfer layer in the organic multilayer structure being a layer of a light-emitting mixture containing at least one species of the aminostyryl compounds.

Also, the organic layer may be of organic multilayer structure composed of a hole transfer layer and an electron transfer layer, with the hole transfer layer being a layer of a light-emitting mixture containing at least one species of the aminostyryl compounds, and the electron transfer layer being the layer of a light-emitting mixture containing at least one species of the aminostyryl compounds, and there exists a hole blocking layer adjacent to the cathode of the layer formed from a light-emitting mixture capable of electron transfer.

Also, the organic layer may be of organic multilayer structure composed of a hole transfer layer, a luminescent layer, and an electron transfer layer, with at least the luminescent layer in the organic multilayer structure being a layer of a light-emitting mixture containing at least one species of the aminostyryl compounds mentioned above.

Also, the organic layer may be constructed such that said at least one layer therein is the layer of a light-emitting mixture containing at least one species of the aminostyryl compounds and a dye emitting red light which has the emission maximum in a range of 600 nm or more.

In this case, the organic layer may be of organic multilayer structure composed of a hole transfer layer and an electron transfer layer, with said at least one layer in the laminate structure being the electron transfer layer.

Also, the organic layer may be of organic multilayer structure composed of a hole transfer layer and an electron transfer layer, with said at least one layer in the laminate structure being the hole transfer layer.

Also, the organic layer may be of organic multilayer structure composed of a hole transfer layer and an electron transfer layer, with the hole transfer layer being the layer of a light-emitting mixture containing at least one species of the aminostyryl compounds and a dye emitting red light which has the emission maximum in the region beyond 600 nm, and the electron transfer layer being a layer of a light-emitting mixture containing at least one species of the aminostyryl compounds and a dye emitting red light which has the emission maximum in a range of 600 nm or more, and there exists a hole blocking layer adjacent to the cathode of the layer formed from a light-emitting mixture capable of electron transfer.

Also, the organic layer may be of organic multilayer structure composed of a hole transfer layer, a luminescent layer, and an electron transfer layer, with the luminescent layer being the layer of a light-emitting mixture containing at least one species of the aminostyryl compounds and a dye emitting red light which has the emission maximum in a range of 600 nm or more.

The present invention is also directed to an organic electroluminescent element (occasionally referred to as the fifth organic EL element of the present invention hereinafter) in which an organic layer having a luminescent region is arranged between an anode and a cathode, characterized in that said organic layer is constructed of at least one layer formed from a aminostyryl compound represented by the above-mentioned general formula [I] and there exists a hole blocking layer adjacent to (particularly in contact with) the cathode of the layer of aminostyryl compound.

In the fifth organic electroluminescent element of the present invention, the organic layer may be of organic multilayer structure composed of a hole transfer layer and an electron transfer layer, with at least the electron transfer layer in the organic multilayer structure being a layer of said aminostyryl compound.

Also, the organic layer may be of organic multilayer structure composed of a hole transfer layer and an electron transfer layer, with at least the hole transfer layer in the organic multilayer structure being the layer of said aminostyryl compound.

Also, the organic layer may be of organic multilayer structure composed of a hole transfer layer and an electron transfer layer, with the hole transfer layer being the layer of the aminostyryl compound, and the electron transfer layer being the layer of the aminostyryl compound, and there exists the hole blocking layer adjacent to the cathode of the layer of aminostyryl compound capable of electron transfer.

Also, the organic layer may be of organic multilayer structure composed of a hole transfer layer, a luminescent layer, and an electron transfer layer, with at least the luminescent layer in the organic multilayer structure being the layer of the aminostyryl compound.

In the fifth organic EL element of the present invention, the hole blocking layer may be constructed in the same way as that in the third organic EL element of the present invention.

The present invention is-also directed to an organic electroluminescent element (occasionally referred to as the sixth organic element of the present invention) in which an organic layer having a luminescent region is arranged between an anode and a cathode, characterized in that said organic layer is constructed of at least one layer formed solely from an aminostyryl compound selected from the aminostyryl compounds represented by the above-mentioned structural formulas (15)-1 to (15)-12, (16)-1 to (16)-12, (17)-1 to (17)-6, and (18)-1 to (18)-6, and there exists a hole blocking layer adjacent to the cathode of the layer of said aminostyryl compound.

In the sixth organic EL element of the present invention, the organic layer may be of organic multilayer structure composed of a hole transfer layer and an electron transfer layer, with at least the electron transfer layer in the organic multilayer structure being the layer of said aminostyryl compound.

Also, the organic layer may be of organic multilayer structure composed of a hole transfer layer and an electron transfer layer, with at least the hole transfer layer in the organic multilayer structure being the layer of said aminostyryl compound.

Also, the organic layer many be of organic multilayer structure composed of a hole transfer layer and an electron transfer layer, with the hole transfer layer being the layer of the aminostyryl compound, and the electron transfer layer being the layer of the aminostyryl compound, and there exists the hole blocking layer adjacent to the cathode of the layer of aminostyryl compound capable of electron transfer.

Also, the organic layer may be of organic multilayer structure composed of a hole transfer layer, a luminescent layer, and an electron transfer layer, with at least the luminescent layer in the organic multilayer structure being the layer of the aminostyryl compound.

FIGS. 1 to 9 show the examples of the organic electroluminescent element (organic EL element) pertaining to the present invention.

FIG. 1 shows a transmission-type organic electroluminescent element A which is constructed such that the emitted light 20 passes through the cathode 3. The emitted light 20 is also visible from the side of the protective layer 4. FIG. 2 shows a reflection-type organic electroluminescent element B which is constructed such that the emitted light 20 is reflected by the cathode 3.

In FIGS. 1 and 2, there is shown a substrate 1 on which is formed the organic electroluminescent element. It may be made of glass, plastics, or any other appropriate material. In the case where the organic electroluminescent element is used in combination with any other display element the substrate may be used in common. There is shown a transparent electrode (anode) 2, which may be made of ITO (indium tin oxide) or $SnO_2$.

There is shown an organic luminescent layer 5, which contains the above-mentioned aminostyryl compound as a luminescent material. (The aminostyryl compound may be used individually in combination with any other compound or more than one kind of aminostyryl compound may be used in combination with one another. The same shall apply hereinafter.) The organic luminescent layer capable of obtaining organic electroluminescent light 20 may have any known layer construction. In the case where either of the hole transfer layer or the electron transfer layer is formed from a luminescent material, the luminescent layer may be formed from thin layers placed one over another, as explained later. Both or either of the hole transfer layer and the electron transfer layer may be of laminate structure composed of thin films of a plurality of materials or may be a thin film composed of a plurality of materials. This structure may be used to increase the charge transfer performance to such an extent as to meet the object of the present invention. Another layer structure that can be used to increase the luminescent performance includes one in which a thin film of at least one kind of fluorescent material is interposed between the hole transfer layer and the electron transfer layer, or one in which at least one kind of fluorescent material is contained in both the hole transfer layer and the electron transfer layer. In this case the layer structure may contain an additional thin film to control the hole transfer or electron transfer, thereby improving the luminescence efficiency.

The aminostyryl compound represented by the above-mentioned general formula [1] is capable of both electron transfer and hole transfer; therefore, it can be used as the light-emitting layer which functions also as the electron transfer layer or as the light-emitting layer which functions also as the hole transfer layer. The electroluminescent element may be constructed such that the light-emitting layer (which is formed from said compound) is interposed between the electron transfer layer and the hole transfer layer.

Incidentally, in FIGS. 1 and 2, there is shown a cathode 3. The cathode may be formed from an alloy of active metal (such as Li, Mg, and Ca) and metal (such as Ag, Al, and In), or may be formed from layers of these metals. In the case of an organic electroluminescent element of transmission type, the cathode may have an adequate thickness so that a desired light transmittance is attained for specific uses. In addition, there is shown a sealing/protective layer 4, which entirely covers the organic electroluminescent element to ensure its performance. It can be formed from any material which maintains air tightness.

The organic electroluminescent element according to the present invention may have an organic layer of laminate structure (or single-hetero structure) which is composed of a hole transfer layer and an electron transfer layer. In this case, the hole transfer layer or the electron transfer layer may be formed from a mixture containing the above-mentioned aminostyryl compound. Alternatively, the organic layer may be of double-hetero structure, in which a hole transfer layer, a luminescent layer, and an electron transfer layer are sequentially laminated on top of the other. In this case, the luminescent layer is formed from a mixture containing the above-mentioned aminostyryl compound.

An embodiment of the organic electroluminescent element of organic multilayer structure as mentioned above is illustrated in FIG. 3. It consists of a transparent substrate 1, a transparent anode 2, an organic layer 5a (composed of a hole transfer layer 6 and an electron transfer layer 7), and a cathode 3, which are sequentially placed on top of the other. The entire laminate structure is sealed with a protective layer 4. (Organic electroluminescent element C of single-hetero structure)

The element of layer structure shown in FIG. 3 (in which the luminescent layer is omitted) emits light 20 of desired wavelength from the interface between the hole transfer layer 6 and the electron transfer layer 7. The emitted light is visible through the substrate 1.

An embodiment of laminate structure shown in FIG. 4 consists of a transparent substrate 1, a transparent anode 2, an organic layer 5b (composed of a hole transfer layer 10; a luminescent layer 11, and an electron transfer layer 12), and a cathode 3, which are sequentially placed on top of the other. The entire laminate structure is sealed with a protective layer 4. (Organic electroluminescent element D of double-hetero structure)

The organic electroluminescent element shown in FIG. 4 works as follows. A dc voltage applied across the anode 2 and the cathode 3 causes holes (injected from the anode 2) to reach the luminescent layer 11 through the hole transfer layer 10 and also causes electrons (injected from the cathode 3) to reach the luminescent layer 11 through the electron transfer layer 12. As the result, recombination of electrons and holes takes place in the luminescent layer 11, thereby giving rise to singlet excitons which emit light of desired wavelength.

In the above-mentioned organic electroluminescent elements C and D, the substrate 1 may be formed from any transparent material such as glass and plastics. If this element is used in combination with other display element or if the elements of laminate structure as shown in FIGS. 3 and 4 are arranged in a matrix, one substrate may be used in common. Also, the elements C and D may be either of transmission type or of reflection type.

The anode 2 is a transparent electrode, which may be made of ITO or $SnO_2$. A thin film of organic substance or organometallic compound may be interposed between the anode 2 and the hole transfer layer 6 (or 10), for improvement in the charge injection efficiency. In the case where the protective film 4 is made of an electrically conductive material such as metal, then the anode 2 may be surrounded by an insulating film.

In the organic electroluminescent element C, the organic layer 5a is composed of the hole transfer layer 6 and the electron transfer layer 7, and the above-mentioned aminostyryl compound is contained in either of them. In this case, the hole transfer layer 6 or the electron transfer layer 7 emits light. In the organic electroluminescent element D, the organic layer 5b is composed of the hole transfer layer 10, the luminescent layer 11 (containing the above-mentioned aminostyryl compound), and the electron transfer layer 12 which are laminated on top of the other. The layer structure may be modified in any other way. For example, either or both of the hole transfer layer and the electron transfer layer may emit light.

In addition, the hole transfer layer may be constructed of laminate of several kinds of hole transfer materials for improvement in the hole transfer performance.

In the organic electroluminescent element C, the luminescent layer may be the electron transferring luminescent layer 7. In this case, light is emitted from the hole transfer layer 6 or the interface thereof depending on voltage applied from the power source 8. Likewise, in the organic electroluminescent element D, the electron transfer layer 12 or the hole transfer layer 10 may also function as the luminescent layer 11. A desirable structure for improved luminescent performance is such that a luminescent layer 11 containing at least one kind of fluorescent material is interposed between the hole transfer layer 11 and the electron transfer layer 12. Alternatively, the fluorescent material may be contained in either or both of the hole transfer layer and the electron transfer layer. In this case, the layer structure may contain a thin film (such as hole blocking layer and exciton generating layer) to control the transfer of holes or electrons for improvement in the light-emitting performance.

The cathode 3 may be formed from an alloy of active metal (such as Li, Mg, and Ca) and metal (such as Ag, Al, and In). These metals may be used in the form of laminate layers. The thickness and material of the cathode should be properly selected according to the use of the organic electroluminescent element.

The protective layer 4 functions as a sealing film. It should cover the organic electroluminescent element entirely so as to improve the charge injection efficiency and the light-emitting efficiency. It may be formed from any material (such as aluminum, gold, and chromium in the form of metal or alloy) so long as it keeps air tightness.

The above-mentioned organic electroluminescent elements work upon application of direct current. However, they may be operated by pulse current or alternating current. The magnitude of current and voltage is not specifically restricted so long as the element is not broken. It is desirable that the element emits light efficiency with a small amount of electric energy in view of the power consumption and life of the organic electroluminescent elements.

The organic EL elements A to D shown in FIGS. 1 to 4 may be modified as shown in FIGS. 5 to 9 (designated by A' to D', respectively). They have a hole blocking layer 30 adjacent to the luminescent layer 5, the hole transfer layer 6, the electron transfer layer 7, or the luminescent layer 11 (the side facing the cathode 3). The above-mentioned aminostyryl compound may be used individually in combination with any other compound or more than one kind of aminostyryl compound may be used in combination with one another, or a single aminostyryl compound may form the layer.

The organic electroluminescent elements of the present invention may be used to construct a flat display as shown in FIG. 10. For full-color display, the organic layer 5 (5a, 5b), each capable of emitting primary color of red (R), green (G), and blue (B), are interposed between the cathode 3 and the anode 2. The cathode 3 and anode 2 may be stripes intersecting each other. Each element is selected by the luminance signal circuit 14 and the control circuit 15 having a shift register. A signal voltage is applied according to the selection, so that the organic layer (pixel) at the intersection of the selected cathode 3 and anode 2 emits light.

An embodiment of simple matrix (8×3 RGB) is shown in FIG. 10. It is constructed such that a laminate 5 is interposed between the cathode 3 and the anode 2. This laminate is composed of the hole transfer layer and at least either of the luminescent layer and the electron transfer layer. (See FIG. 3 or 4.) Both the cathode and the anode are patterned in stripe form so that they intersect each other at right angles. Signal voltage is applied sequentially by the control circuits 15 (with a shift register) and the luminance signal circuit 14. The element at the intersection emits light. The EL element constructed in this way can be used as a display for characters and signs and it can also be used as an image reproducing apparatus. If the stripe pattern of the cathode 3 and anode 2 is arranged for each of red (R), green (G), and blue (B) colors, a multi-color or full-color solid flat display panel can be constructed.

DETAILED DESCRIPTION OF THE INVENTION

The invention will be described in more detail with reference to the following examples, which are not intended to restrict the scope thereof.

EXAMPLE 1

This example demonstrates the production of an organic electroluminescent element of single hetero structure in which the luminescent layer capable of hole transfer is made of a mixture of an aminostyryl compound represented by the following structural formula (15)-3 and a-NPD (a-naphthylphenyldiamine). The former is one of the aminostyryl compounds represented by the above-mentioned general formula [I].

Structural formula (15)-3:

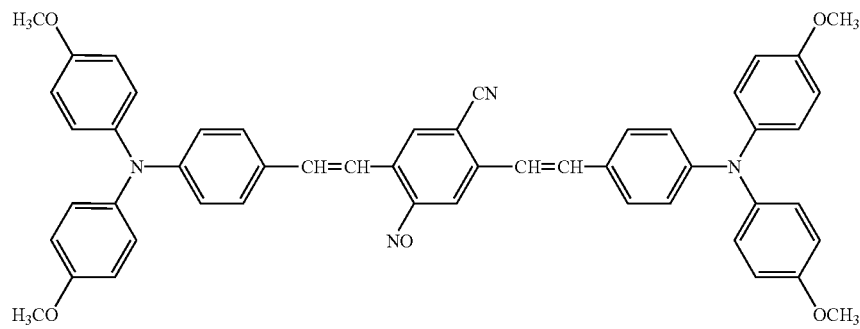

a-NPD:

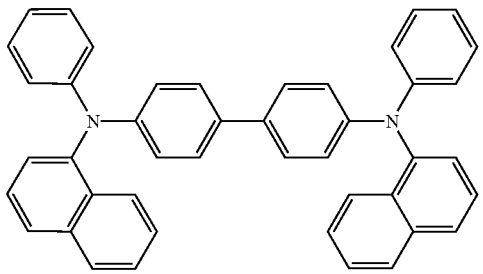

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited by vacuum deposition (at $10^{-4}$ Pa or less) the aminostyryl compound of the above-mentioned structural formula (15)-3 and a-NPD (as the hole transfer material). There was formed a 50-nm thick hole transfer layer (functioning also as a luminescent layer) consisting of the two components in a ratio of 1:1 by weight. The rate of deposition was 0.1 nm/sec.

Then, on the hole transfer layer was formed a 50-nm thick electron transfer layer by vacuum deposition from $Alq_3$ (tris(8-quinolinol)aluminum) represented by the following structural formula. The rate of deposition was 0.2 nm/sec.

$Alq_3$:

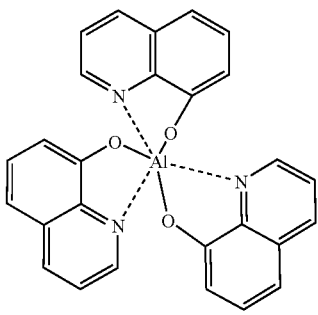

Figure 1:
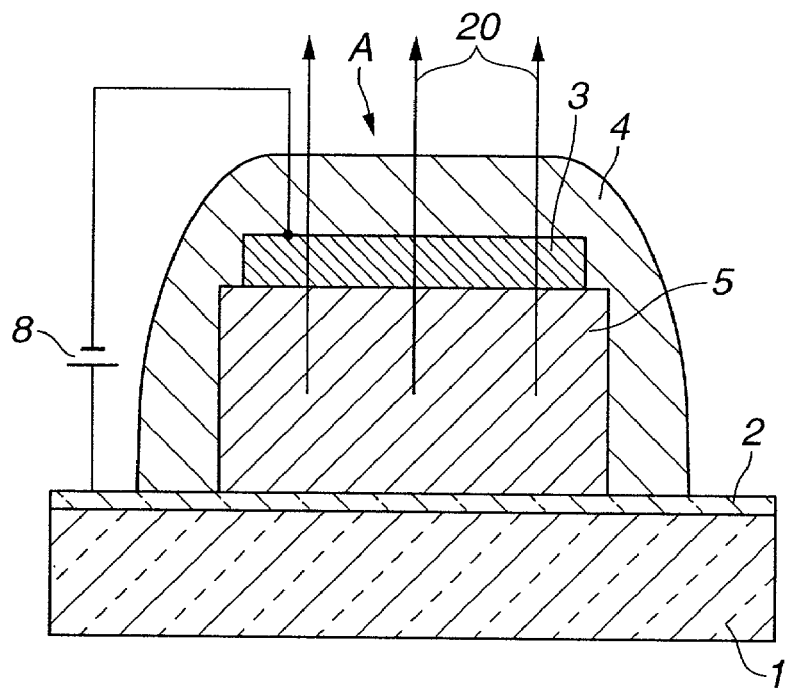
FIG. 1 is a schematic sectional view showing important parts of the organic electroluminescent element in one example of the present invention.
Figure 2:
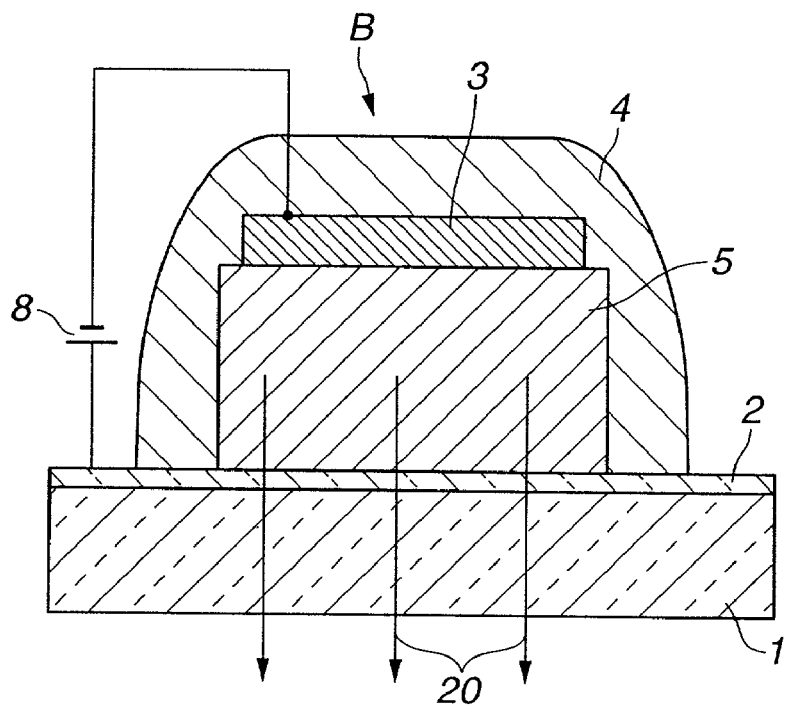
FIG. 2 is a schematic sectional view showing important parts of the organic electroluminescent element in another example of the present invention.
Figure 3:
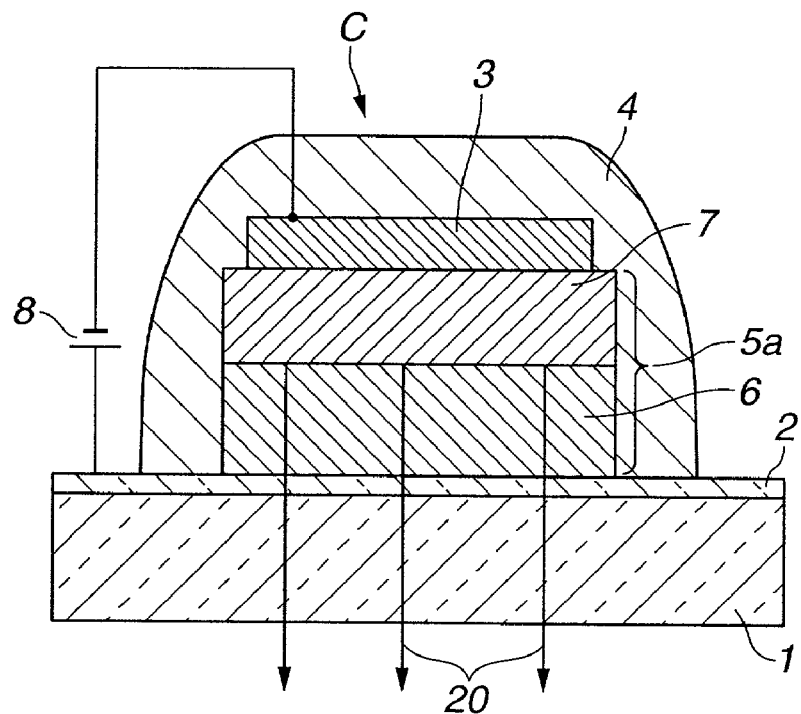
FIG. 3 is a schematic sectional view showing important parts of the organic electroluminescent element in another example of the present invention.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 3.

The organic electroluminescent element of Example 1 produced in this manner was examined for luminescent characteristics by applying a forward bias dc voltage in a nitrogen atmosphere. It emitted red light. By spectral analysis with a spectroscope having a photodiode array as a detector (made by Otsuka Electronics Co., Ltd.), the emitted light was found to have the luminescent peak at about 630 nm. In addition, the emitted light was found to have a luminance of 2000 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 900 hours for the element to decrease in luminance by half.

EXAMPLE 2

This example demonstrates the production of an organic electroluminescent element of single hetero structure in which the luminescent layer capable of electron transfer is made of a mixture of an aminostyryl compound represented by the above-mentioned structural formula (15)-3 and $Alq_3$. The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited a-NPD by vacuum deposition (at $10^{-4}$ Pa or less) to form a 50-nm thick film. The rate of deposition was 0.1-nm/sec.

Then, on the hole transfer layer was formed a layer of a 1:1 mixture (by weight) composed of the aminostyryl compound of the above-mentioned structural formula (15)-3 and $Alq_3$ (as the electron transfer material). Thus there was formed a 50-nm thick electron transfer layer (which functions also as the luminescent layer) consisting of the aminostyryl compound of structural formula (15)-3 and $Alq_3$. The rate of deposition was 0.2 nm/sec each.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 3.

The organic electroluminescent element of Example 2 produced in this manner was examined for luminescent characteristics by applying a forward bias dc voltage in a nitrogen atmosphere. It emitted red light. By spectral analysis in the same way as in Example 1, the emitted light was found to have the luminescent peak at about 630 nm. In addition, the emitted light was found to have a luminance of 1200 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 800 hours for the element to decrease in luminance by half.

EXAMPLE 3

This example demonstrates the production of an organic electroluminescent element of double hetero structure in which the luminescent layer capable of electron transfer is made of a mixture of an aminostyryl compound represented by the above-mentioned structural formula (15)-3 and $Alq_3$.

The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited a-NPD by vacuum deposition (at $10^{-4}$ Pa or less) to form a 30-nm thick film. The rate of deposition was 0.2 nm/sec.

Then, on the hole transfer layer was formed a layer of a 1:1 mixture (by weight) composed of the aminostyryl compound of the above-mentioned structural formula (15)-3 and Alq$_3$ (as the luminescent material). Thus there was formed a 30-nm thick luminescent layer consisting of the aminostyryl compound of structural formula (15)-3 and Alq$_3$. The rate of deposition was 0.2 nm/sec each.

Further, on the luminescent layer was formed a 30 nm thick electron transfer layer by vacuum deposition from Alq$_3$. The rate of deposition was 0.2 nm/sec.

Figure 4:
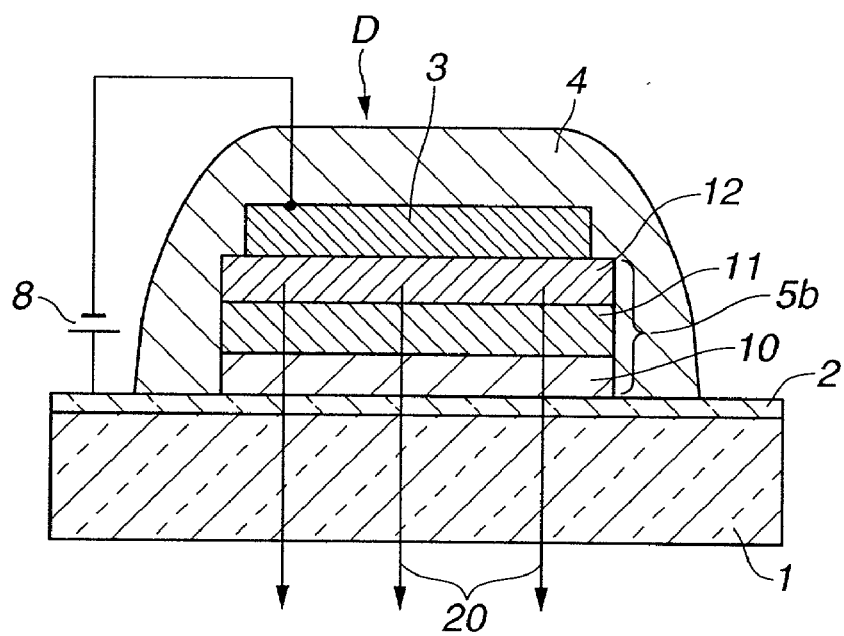
FIG. 4 is a schematic sectional view showing important parts of the organic electroluminescent element in another example of the present invention.
Figure 5:
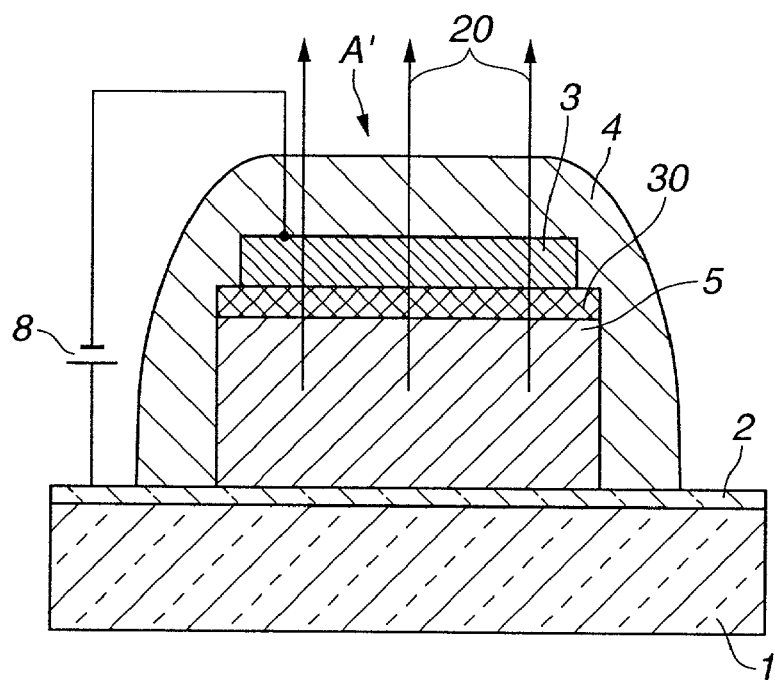
FIG. 5 is a schematic sectional view showing important parts of the organic electroluminescent element in another example of the present invention.
Figure 6:
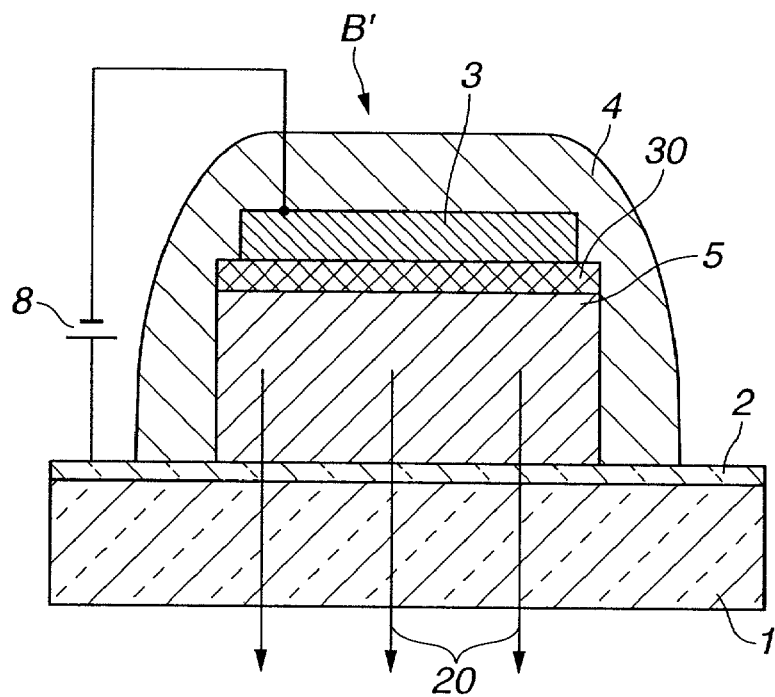
FIG. 6 is a schematic sectional view showing important parts of the organic electroluminescent element in another example of the present invention.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 4.

The organic electroluminescent element produced in this manner was examined for luminescent characteristics by applying a forward bias dc voltage in a nitrogen atmosphere. It emitted red light. By spectral analysis in the same way as in Example 1, the emitted light was found to have the luminescent peak at about 630 nm. In addition, the emitted light was found to have a luminance of 2500 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1500 hours for the element to decrease in luminance by half.

EXAMPLE 4

This example demonstrates the production of an organic electroluminescent element of double hetero structure in which the luminescent layer is made of a mixture of an aminostyryl compound represented by the above-mentioned structural formula (15)-3 and an aminostyryl compound represented by the following structural formula (15)-1. The former is one of the aminostyryl compounds represented by the above-mentioned general formula [I].

Structural formula (15)-1:

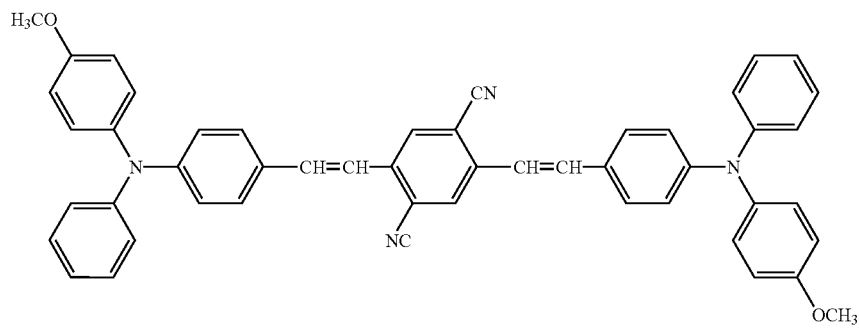

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited a-NPD by vacuum deposition (at lower than $10^{-4}$ Pa) to form a 30-nm thick film. The rate of deposition was 0.2 nm/sec.

Then, on the hole transfer layer was formed a layer of a 1:3 mixture (by weight) composed of the aminostyryl compound of the above-mentioned structural formula (15)-3 and the aminostyryl compound of the above-mentioned structural formula (15)-1. Thus there was formed a 30-nm thick luminescent layer consisting of the aminostyryl compound of structural formula (15)-3 and the aminostyryl compound of structural formula (15)-1. The rate of deposition was 0.1 nm/sec for the former compound and 0.3 nm/sec for the latter compound.

Further, on the luminescent layer was formed a 30-nm thick electron transfer layer by vacuum deposition from Alq$_3$. The rate of deposition was 0.2 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 4.

The organic electroluminescent element of Example 3 produced in this manner was examined for luminescent characteristics by applying a forward bias dc voltage in a nitrogen atmosphere. It emitted red light. By spectral analysis in the same way as in Example 1, the emitted light was found to have the luminescent peak at about 640 nm. In addition, the emitted light was found to have a luminance of 3000 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1200 hours for the element to decrease in luminance by half.

EXAMPLE 5

This example demonstrates the production of an organic electroluminescent element of single hetero structure in which the luminescent layer capable of electron transfer is made of a mixture of an aminostyryl compound represented by the above-mentioned structural formula (15)-3 and DCM represented by the following structural formula. The former is one of the aminostyryl compounds represented by the above-mentioned general formula [I].

DCM:

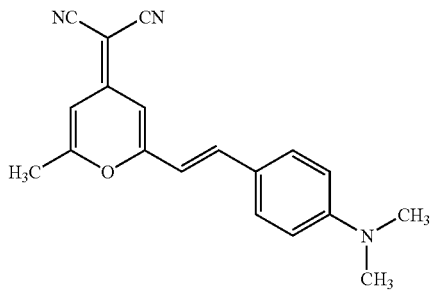

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited a-NPD of the above-mentioned structure by vacuum deposition (at $10^{-4}$ Pa or less) to form a 50-nm thick film. The rate of deposition was 0.1 nm/sec.

Then, on the hole transfer layer was formed a layer of a 10:1 mixture (by weight) composed of the aminostyryl compound of the above-mentioned structural formula (15)-3 and the above-mentioned DCM. Thus there was formed a 50-nm thick electron transfer layer (which functions also as the luminescent layer) consisting of the aminostyryl compound of structural formula (15)-3 and the above-mentioned DCM. The rate of deposition was 0.5 nm/sec for the former compound and 0.05 nm/sec for the latter compound.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 3.

The organic electroluminescent element of Example 5 produced in this manner was examined for luminescent characteristics by applying a forward bias dc voltage in a nitrogen atmosphere. It emitted red light. By spectral analysis in the same way as in Example 1, the emitted light was found to have the luminescent peak at about 630 nm. In addition, the emitted light was found to have a luminance of 800 $cd/m^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 $cd/m^2$ was allowed to emit light -continuously by application of constant current. It took 500 hours for the element to decrease in luminance by half.

EXAMPLE 6

This example demonstrates the production of an organic electroluminescent element of single hetero structure in which the luminescent layer capable of electron transfer is made of a mixture of an aminostyryl compound represented by the following structural formula (15)-2 and $Alq_3$. The former is one of the aminostyryl compounds represented by the above-mentioned general formula [I].

Structural formula (15)-2:

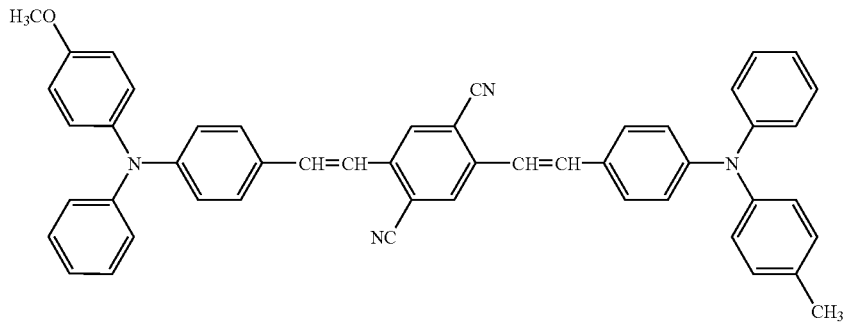

The organic electroluminescent element was identical with that of Example 2 in layer structure and method of film formation.

The organic electroluminescent element of Example 6 produced in this manner was examined for luminescent characteristics by applying a forward bias dc voltage in a nitrogen atmosphere. It emitted orange light. By spectral analysis in the same way as in Example 1, the emitted light was found to have the luminescent peak at about 590 nm. In addition, the emitted light was found to have a luminance of 850 $cd/m^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 $cd/m^2$ was allowed to emit light continuously by application of constant current. It took 600 hours for the element to decrease in luminance by half.

EXAMPLE 7

This example demonstrates the production of an organic electroluminescent element of single hetero structure in which the luminescent layer capable of electron transfer is made of a mixture of an aminostyryl compound represented by the following structural formula (15)-4 and $Alq_3$. The former is one of the aminostyryl compounds represented by the above-mentioned general formula [I].

Structural formula (15)-4:

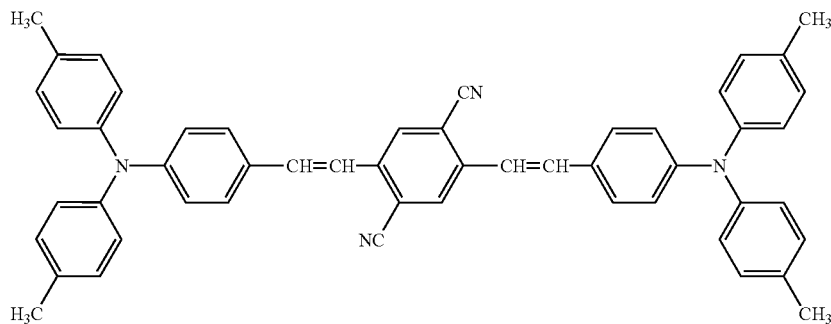

The organic electroluminescent element was identical with that of Example 2 in layer structure and method of film formation.

The organic electroluminescent element of Example 7 produced in this manner was examined for luminescent characteristics by applying a forward bias dc voltage in a nitrogen atmosphere. It emitted red light. By spectral analysis in the same way as in Example 1, the emitted light was found to have the luminescent peak at about 610 nm. In addition, the emitted light was found to have a luminance of 800 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 450 hours for the element to decrease in luminance by half.

EXAMPLE 8

This example demonstrates the production of an organic electroluminescent element of single hetero structure in which the luminescent layer capable of electron transfer is made of a mixture of an aminostyryl compound represented by the following structural formula (15)-6 and Alq$_3$. The former is one of the aminostyryl compounds represented by the above-mentioned general formula [I].

Structural formula (15)-6:

The organic electroluminescent element was identical with that of Example 2 in layer structure and method of film formation.

The organic electroluminescent element of Example 8 produced in this manner was examined for luminescent characteristics by applying a forward bias dc voltage in a nitrogen atmosphere. It emitted orange light. By spectral analysis in the same way as in Example 1, the emitted light was found to have the luminescent peak at about 585 nm. In addition, the emitted light was found to have a luminance of 500 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 200 hours for the element to decrease in luminance by half.

EXAMPLE 9

This example demonstrates the production of an organic electroluminescent element of single hetero structure in which the luminescent layer capable of electron transfer is made of a mixture of an aminostyryl compound represented by the following structural formula (15)-7 and Alq$_3$. The former is one of the aminostyryl compounds represented by the above-mentioned general formula [I].

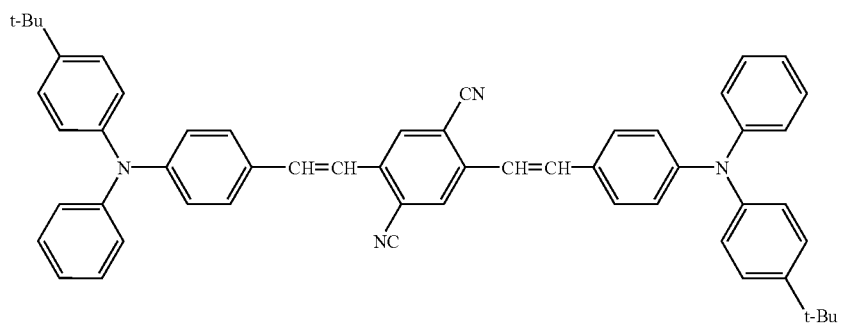

Structural formula (15)-7:

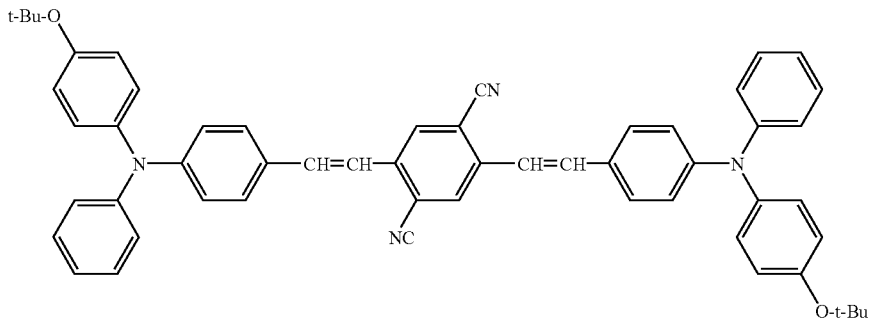

The organic electroluminescent element was identical with that of Example 2 in layer structure and method of film formation.

The organic electroluminescent element of Example 9 produced in this manner was examined for luminescent characteristics by applying a forward bias dc voltage in a nitrogen atmosphere. It emitted red light. By spectral analysis in, the same way as in Example 1, the emitted light was found to have the luminescent peak at about 615 nm. In addition, the emitted light was found to have a luminance of 580 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 300 hours for the element to decrease in luminance by half.

EXAMPLE 10

This example demonstrates the production of an organic electroluminescent element of single hetero structure in which the luminescent layer capable of electron transfer is made of a mixture of an aminostyryl compound represented by the following structural formula (15)-8 and Alq$_3$. The former is one of the aminostyryl compounds represented by the above-mentioned general formula [I].

Structural formula (15)-8:

The organic electroluminescent element was identical with that of Example 2 in layer structure and method of film formation.

The organic electroluminescent element of Example 10 produced in this manner was examined for luminescent characteristics by applying a forward bias dc voltage in a nitrogen atmosphere. It emitted red light. By spectral analysis in the same way as in Example 1, the emitted light was found to have the luminescent peak at about 610 nm. In addition, the emitted light was found to have a luminance of 430 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 150 hours for the element to decrease in luminance by half.

EXAMPLE 11

This example demonstrates the production of an organic electroluminescent element of single hetero structure in which the luminescent layer capable of electron transfer is made of a mixture of an aminostyryl compound represented by the following structural formula (15)-9 and Alq$_3$. The former is one of the aminostyryl compounds represented by the above-mentioned general formula [I].

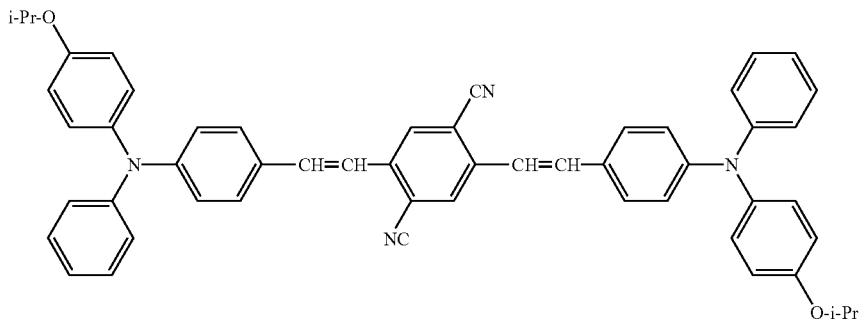

Structural formula (15)-9:

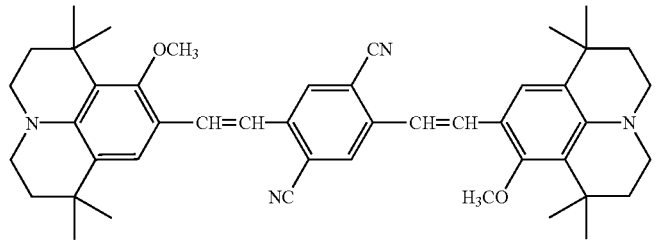

The organic electroluminescent element was identical with that of Example 2 in layer structure and method of film formation.

The organic electroluminescent element of Example 11 produced in this manner was examined for luminescent characteristics by applying a forward bias dc voltage in a nitrogen atmosphere. It emitted red light. By spectral analysis in the same way as in Example 1, the emitted light was found to have the luminescent peak at about 640 nm. In addition, the emitted light was found to have a luminance of 800 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 450 hours for the element to decrease in luminance by half.

EXAMPLE 12

This example demonstrates the production of an organic electroluminescent element of single hetero structure in which the luminescent layer capable of electron transfer is made of a mixture of an aminostyryl compound represented by the following structural formula (15)-11 and Alq₃. The former is one of the aminostyryl compounds represented by the above-mentioned general formula [I].

Structural formula (15)-11:

The organic electroluminescent element was identical with that of Example 2 in layer structure and method of film formation.

The organic electroluminescent element of Example 12 produced in this manner was examined for luminescent characteristics by applying a forward bias dc voltage in a nitrogen atmosphere. It emitted orange light. By spectral analysis in the same way as in Example 1, the emitted light was found to have the luminescent peak at about 580 nm. In addition, the emitted light was found to have a luminance of 1000 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 750 hours for the element to decrease in luminance by half.

EXAMPLE 13

This example demonstrates the production of an organic electroluminescent element of single hetero structure in which the luminescent layer capable of electron transfer is made of a mixture of an aminostyryl compound represented by the following structural formula (15)-12 and Alq₃. The former is one of the aminostyryl compounds represented by the above-mentioned general formula [I].

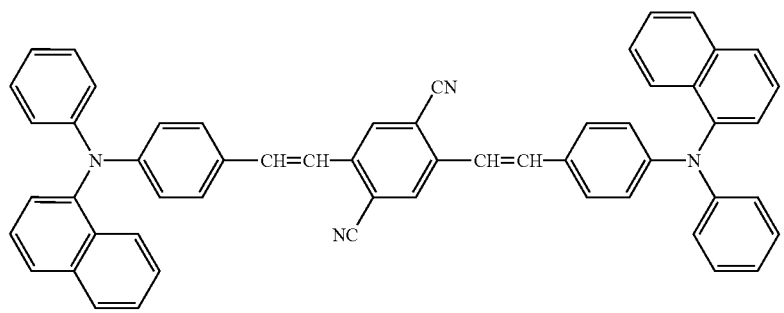

Structural formula (15)-12:

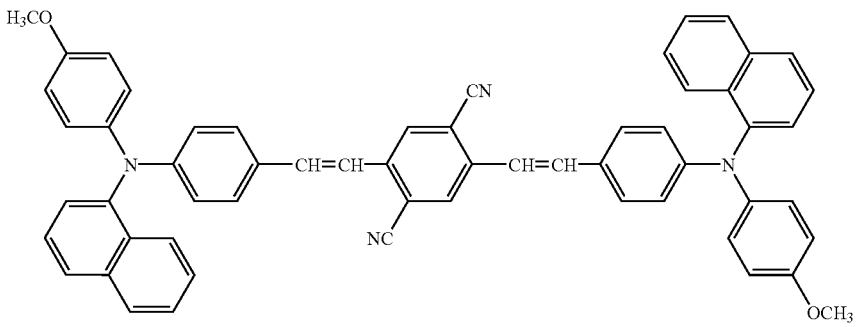

The organic electroluminescent element was identical with that of Example 2 in layer structure and method of film formation.

The organic electroluminescent element of Example 13 produced in this manner was examined for luminescent characteristics by applying a forward bias dc voltage in a nitrogen atmosphere. It emitted orange light. By spectral analysis in the same way as in Example 1, the emitted light was found to have the luminescent peak at about 600 nm. In addition, the emitted light was found to have a luminance of 850 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 600 hours for the element to decrease in luminance by half.

EXAMPLE 14

This example demonstrates the production of an organic electroluminescent element of single hetero structure in which the luminescent layer capable of electron transfer is made of a mixture of an aminostyryl compound represented by the following structural formula (17)-1 and Alq$_3$. The former is one of the aminostyryl compounds represented by the above-mentioned general formula [I].

Structural formula (17)-1:

The organic electroluminescent element was identical with that of Example 2 in layer structure and method of film formation.

The organic electroluminescent element of Example 14 produced in this manner was examined for luminescent characteristics by applying a forward bias dc voltage in a nitrogen atmosphere. It emitted red light. By spectral analysis in the same way as in Example 1, the emitted light was found to have the luminescent peak at about 620 nm. In addition, the emitted light was found to have a luminance of 1500 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 800 hours for the element to decrease in luminance by half.

EXAMPLE 15

This example demonstrates the production of an organic electroluminescent element of single hetero structure in which the luminescent layer capable of electron transfer is made of a mixture of an aminostyryl compound represented by the following structural formula (17)-2 and Alq$_3$. The former is one of the aminostyryl compounds represented by the above-mentioned general formula [I].

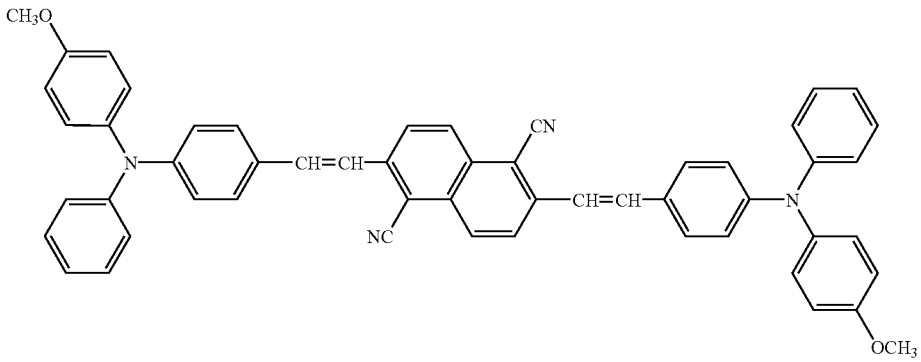

Structural formula (17)-2:

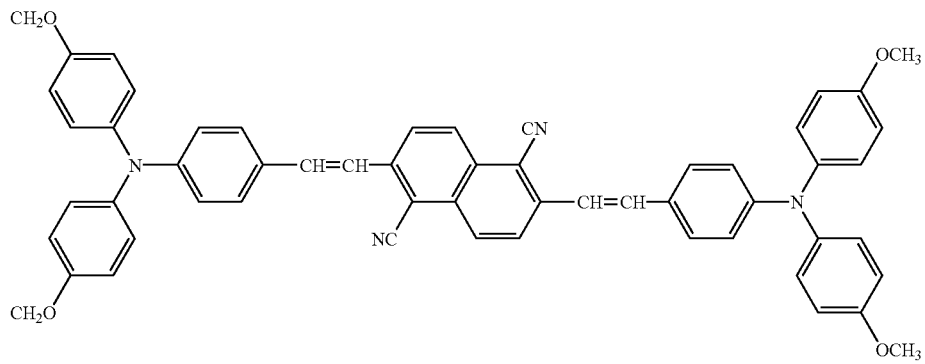

The organic electroluminescent element was identical with that of Example 2 in layer structure and method of film formation.

The organic electroluminescent element of Example 15 produced in this manner was examined for luminescent characteristics by applying a forward bias dc voltage in a nitrogen atmosphere. It emitted red light. By spectral analysis in the same way as in Example 1, the emitted light was found to have the luminescent peak at about 645 nm. In addition, the emitted light was found to have a luminance of 1200 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 700 hours for the element to decrease in luminance by half.

EXAMPLE 16

This example demonstrates the production of an organic electroluminescent element of single hetero structure in which the luminescent layer capable of electron transfer is made of a mixture of an aminostyryl compound represented by the following structural formula (17)-3 and Alq$_3$. The former is one of the aminostyryl compounds represented by the above-mentioned general formula [I].

Structural formula (17)-3:

The organic electroluminescent element was identical with that of Example 2 in layer structure and method of film formation.

The organic electroluminescent element produced in this manner was examined for luminescent characteristics by applying a forward bias dc voltage in a nitrogen atmosphere. It emitted red light. By spectral analysis in the same way as in Example 1, the emitted light was found to have the luminescent peak at about 590 nm. In addition, the emitted light was found to have a luminance of 780 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 500 hours for the element to decrease in luminance by half.

EXAMPLE 17

This example demonstrates the production of an organic electroluminescent element of single hetero structure in which the luminescent layer capable of electron transfer is made of a mixture of an aminostyryl compound represented by the following structural formula (17)-4 and Alq$_3$. The former is one of the aminostyryl compounds represented by the above-mentioned general formula [I].

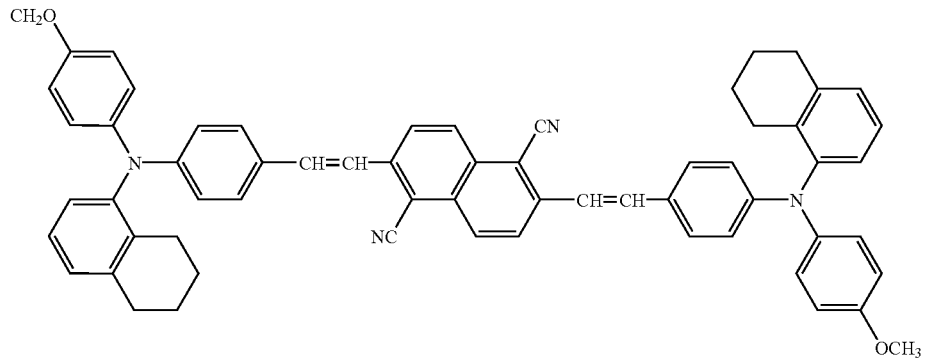

Structural formula (17)-4:

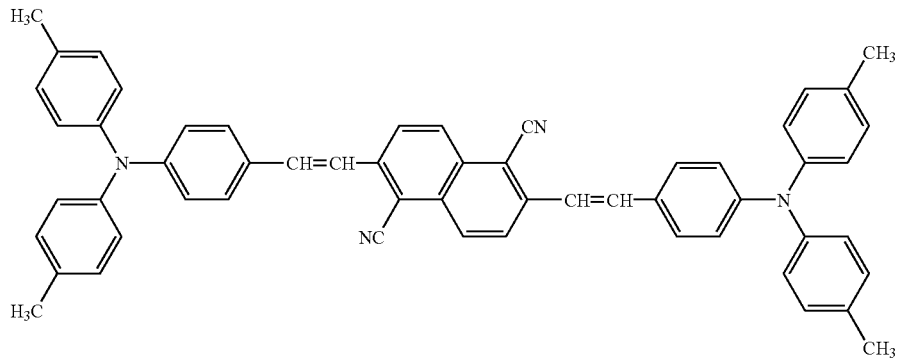

The organic electroluminescent element was identical with that of Example 2 in layer structure and method of film formation.

The organic electroluminescent element of Example 17 produced in this manner was examined for luminescent characteristics by applying a forward bias dc voltage in a nitrogen atmosphere. It emitted red light. By spectral analysis in the same way as in Example 1, the emitted light was found to have the luminescent peak at about 620 nm. In addition, the emitted light was found to have a luminance of 1100 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 600 hours for the element to decrease in luminance by half.

EXAMPLE 18

This example demonstrates the production of an organic electroluminescent element of single hetero structure in which the luminescent layer capable of electron transfer is made of a mixture of an aminostyryl compound represented by the following structural formula (17)-5 and Alq$_3$. The former is one of the aminostyryl compounds represented by the above-mentioned general formula [I].

Structural formula (17)-5:

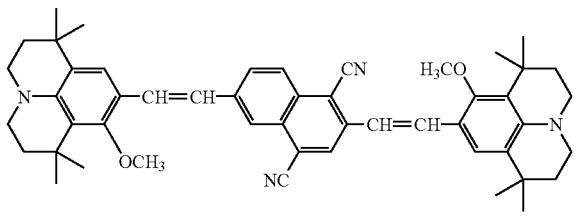

The organic electroluminescent element was identical with that of Example 2 in layer structure and method of film formation.

The organic electroluminescent element of Example 18 produced in this manner was examined for luminescent characteristics by applying a forward bias dc voltage in a nitrogen atmosphere. It emitted red light. By spectral analysis in the same way as in Example 1, the emitted light was found to have the luminescent peak at about 650 nm. In addition, the emitted light was found to have a luminance of 700 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It t ook 400 hours for the element to decrease in luminance by half.

EXAMPLE 19

This example demonstrates the production of an organic electroluminescent element of single hetero structure in which the luminescent layer capable of electron transfer is made of a mixture of an aminostyryl compound represented by the following structural formula (15)-5 and Alq$_3$. The former is one of the aminostyryl compounds represented by the above-mentioned general formula [I].

Structural formula (15)-5:

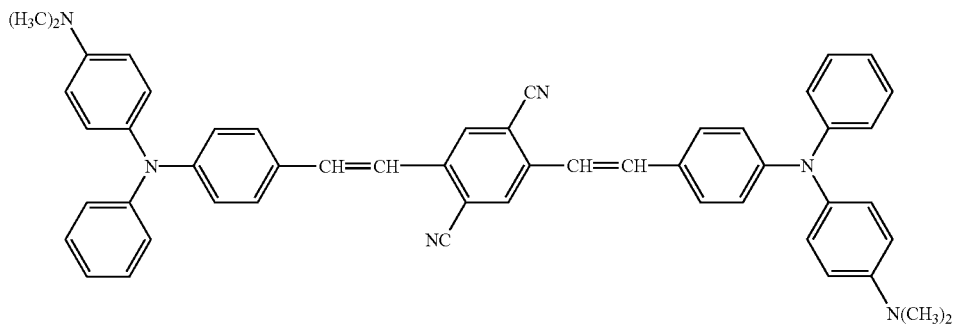

The organic electroluminescent element was identical with that of Example 2 in layer structure and method of film formation.

The organic electroluminescent element of Example produced in this manner was examined for luminescent characteristics by applying a forward bias dc voltage in a nitrogen atmosphere. It emitted red light. By spectral analysis in the same way as in Example 1, the emitted light was found to have the luminescent peak at about 655 nm. In addition, the emitted light was found to have a luminance of 1500 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 700 hours for the element to decrease in luminance by half.

EXAMPLE 20

This example demonstrates the production of an organic electroluminescent element of single hetero structure in which the luminescent layer capable of hole transfer is made of a mixture of an aminostyryl compound represented by the above-mentioned structural formula (15)-3 and a-NPD, and the luminescent layer capable of electron transfer is made of a mixture of an aminostyryl compound represented by the above-mentioned structural formula (15)-3 and Alq$_3$. The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate were deposited by vacuum deposition (at 10$^{-4}$ Pa or less) the aminostyryl compound of the above-mentioned structural formula (15)-3 and a-NPD (as the hole transfer material). There was formed a 50-nm thick hole transfer layer (functioning also as a luminescent layer) consisting of the two components in a ratio of 1:1 by weight. The rate of deposition was 0.1 nm/sec.

Then, on the hole transfer layer (functioning also as a luminescent layer) were deposited by vacuum deposition the aminostyryl compound of the above-mentioned structural formula (15)-3 and Alq$_3$ (as the electron transfer material). There was formed a 50-nm thick electron transfer layer (functioning also as a luminescent layer) consisting of the two components in a ratio of 1:1 by weight. The rate of deposition was 0.1 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element of Example 20 as shown FIG. 3.

The organic electroluminescent element of Example 20 produced in this manner was examined for luminescent characteristics by applying a forward bias dc voltage in a nitrogen atmosphere. It emitted red light. By spectral analysis with a spectroscope having a photodiode array as a detector (made by Otsuka Electronics Co., Ltd.), the emitted light was found to have the luminescent peak at about 635 nm. In addition, the emitted light was found to have a luminance of 1800 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1000 hours for the element to decrease in luminance by half.

EXAMPLE 21

This example demonstrates the production of an organic electroluminescent element in which the luminescent layer capable of hole transfer is made of a mixture of an aminostyryl compound represented by the above-mentioned structural formula (15)-3 and a-NPD (a-naphthylphenyldiamine). The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate were deposited by vacuum deposition (at 10$^{-4}$ Pa or less) the aminostyryl compound of the above-mentioned structural formula (15)-3 and a-NPD (as the hole transfer material). There was formed a 50-nm thick hole transfer layer (functioning also as a luminescent layer) consisting of the two components in a ratio of 1:1 by weight. The rate of deposition was 0.1 nm/sec.

Then, on the hole transfer layer (functioning also as a luminescent layer) was deposited by vacuum deposition vasocuproin of the following structural formula. There was formed a 15-nm thick hole blocking layer. The rate of deposition was 0.1 nm/sec.

Vasocuproin:

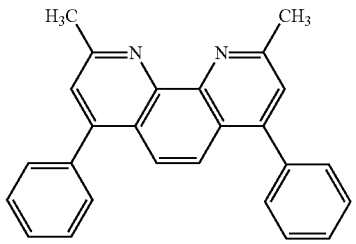

Then, on the hole blocking layer was deposited Alq$_3$ (tris(8-quinolinol)aluminum) of the above-mentioned structural formula. There was formed a 50-nm thick electron transfer layer. The rate of deposition was 0.2 nm/sec.

Figure 7:
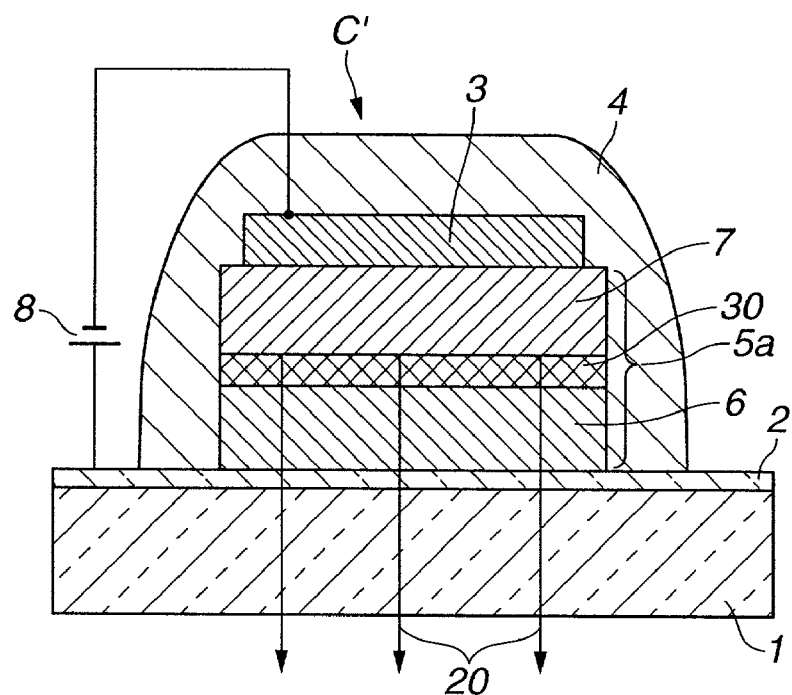
FIG. 7 is a schematic sectional view showing important parts of the organic electroluminescent element in another example of the present invention.
Figure 8:
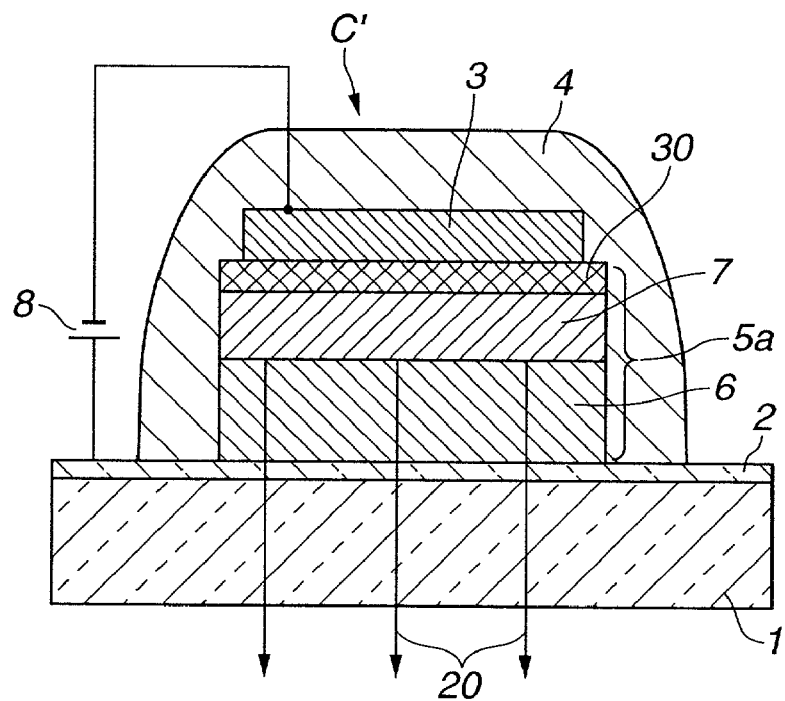
FIG. 8 is a schematic sectional view showing important parts of the organic electroluminescent element in another example of the present invention.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element of Example 21 as shown FIG. 7.

The organic electroluminescent element of Example 21 produced in this manner was examined for luminescent characteristics by applying a forward bias dc voltage in a nitrogen atmosphere. It emitted red light. By spectral analysis with a spectroscope having a photodiode array as a detector (made by Otsuka Electronics Co., Ltd.), the emitted light was found to have the luminescent peak at about 630 nm. In addition, the emitted light was found to have a luminance of 2500 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1000 hours for the element to decrease in luminance by half.

EXAMPLE 22

This example demonstrates the production of an organic electroluminescent element in which the luminescent layer capable of electron transfer is made of a mixture of an aminostyryl compound represented by the above-mentioned structural formula (15)-3 and Alq$_3$. The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited by vacuum deposition (at 10$^{-4}$ Pa or less) a-NPD by the under-mentioned structural formula to form a 30-nm thick film. The rate of deposition was 0.1 nm/sec.

Then, on the hole transfer layer was co-deposited by vacuum deposition a 1:1 mixture (by weight) of the compound of the above-mentioned structural formula (15)-3 and Alq$_3$ as the electron transfer material. There was formed a 30-nm thick electron transfer layer (functioning also as a luminescent layer) composed of the above-mentioned two components. The rate of deposition was 0.2 nm/sec.

Then, on the hole transfer layer (functioning also as a luminescent layer) was deposited by vacuum deposition vasocuproin of the above-mentioned structural formula. There was formed a 15-nm thick hole blocking layer. The rate of deposition was 0.1 nm/sec.

Then, on the hole blocking layer was deposited Alq$_3$ of the above-mentioned structural formula as the electron transfer layer material. There was formed a 30-nm thick electron transfer layer. The rate of deposition was 0.2 nm/sec.

Figure 9:
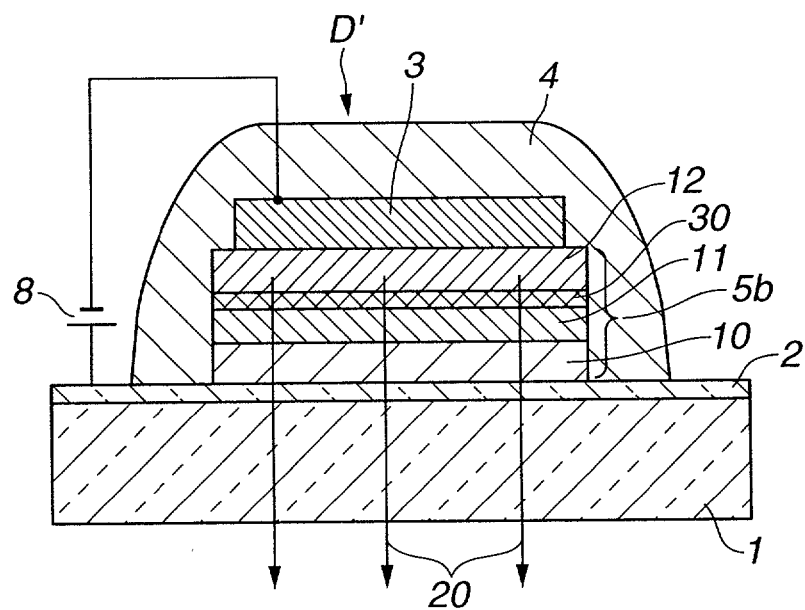
FIG. 9 is a schematic sectional view showing important parts of the organic electroluminescent element in another example of the present invention.
Figure 10:
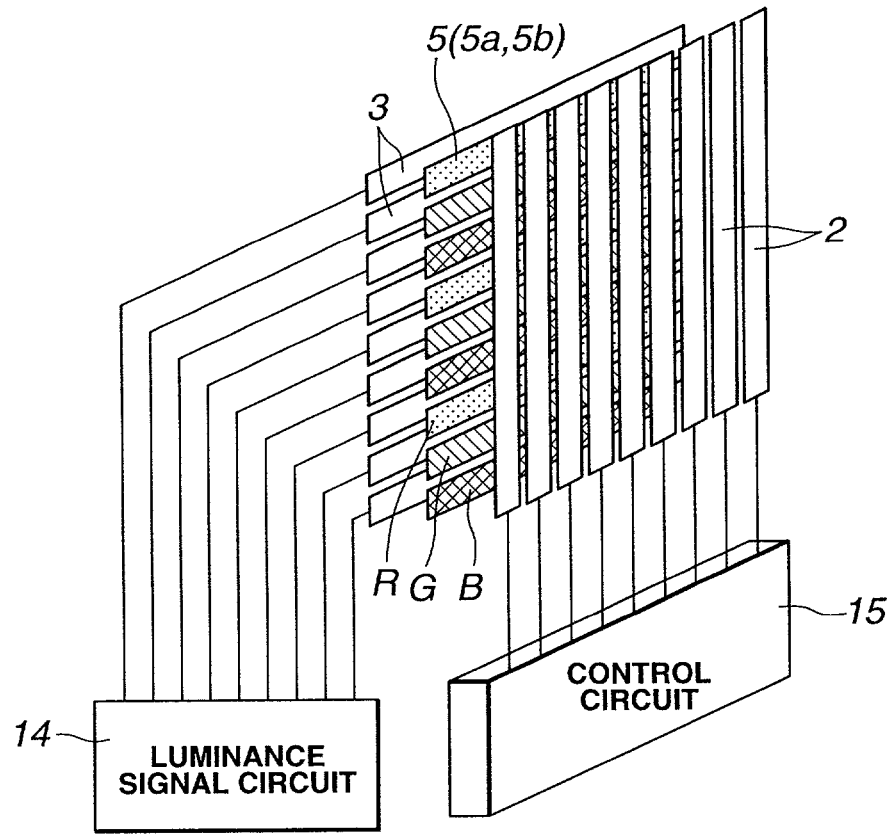
FIG. 10 is a diagram showing the structure of a full-color flat display composed of the organic electroluminescent elements according to the present invention.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 9.

The organic electroluminescent element of Example 22 produced in this manner was examined for luminescent characteristics by applying a forward bias dc voltage in a nitrogen atmosphere. It emitted red light. By spectral analysis in the same way as in Example 21, the emitted light was found to have the luminescent peak at about 630 nm. In addition, the emitted light was found to have a luminance of 3400 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1200 hours for the element to decrease in luminance by half.

EXAMPLE 23

This example demonstrates the production of an organic electroluminescent element in which the luminescent layer is made of a mixture of an aminostyryl compound represented by the above-mentioned structural formula (15)-3 and an aminostyryl compound represented by the above-mentioned structural formula (15)-1.

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited by vacuum deposition (at 10$^{-4}$ Pa or less) a-NPD to form a 30-nm thick film. The rate of deposition was 0.2 nm/sec.

Then, on the hole transfer layer was co-deposited by vacuum deposition a 1:3 mixture (by weight) of the compound of the above-mentioned structural formula (15)-3 and the compound of the above-mentioned structural formula (15)-1 as the luminescent material. There was formed a 30-nm thick luminescent layer composed of the above-mentioned two compounds. The rate of deposition was 0.1 nm/sec for the former compound and 0.3 nm/sec for the latter compound.

Then, on the luminescent layer was deposited by vacuum deposition vasocuproin of the above-mentioned structural formula as the hole blocking layer material. There was formed a 15-nm thick hole blocking layer. The rate of deposition was 0.1 nm/sec.

Then, on the hole blocking layer was deposited Alq$_3$ of the above-mentioned structural formula as the electron transfer material. There was formed a 30-nm thick electron transfer layer. The rate of deposition was 0.2 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element of Example 23 as shown FIG. 9.

The organic electroluminescent element of Example 23 produced in this manner was examined for luminescent characteristics by applying a forward bias dc voltage in a nitrogen atmosphere. It emitted red light. By spectral analysis in the same way as in Example 21, the emitted light was found to have the luminescent peak at about 640 nm. In addition, the emitted light was found to have a luminance of 4000 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1600 hours for the element to decrease in luminance by half.

EXAMPLE 24

This example demonstrates the production of an organic electroluminescent element in which the electron transfer layer is made of a mixture of an aminostyryl compound of the above-mentioned structural formula (15)-3 and DCM of the above-mentioned structural formula. The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited by vacuum deposition (at 10$^{-4}$ Pa or less) a-NPD to form a 30-nm thick film. The rate of deposition was 0.1 nm/sec.

Then, on the hole transfer layer was co-deposited by vacuum deposition a 10:1 mixture (by weight) of the compound of the above-mentioned structural formula (15)-3 and the above-mentioned DCM. There was formed a 30-nm thick electron transfer layer (functioning also as a luminescent layer) composed of the above-mentioned two compounds. The rate of deposition was 0.5 nm/sec for the former compound and 0.05 nm/sec for the latter compound.

Then, on the luminescent layer was deposited by vacuum deposition vasocuproin of the above-mentioned structural formula as the hole blocking layer material. There was formed a 15-nm thick hole blocking layer. The rate of deposition was 0.1 nm/sec.

Then, on the hole blocking layer was deposited Alq$_3$ of the above-mentioned structural formula as the electron transfer material. There was formed a 30-nm thick electron transfer layer. The rate of deposition was 0.2 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 9.

The organic electroluminescent element of Example 24 produced in this manner was examined for luminescent characteristics by applying a forward bias dc voltage in a nitrogen atmosphere. It emitted red light. By spectral analysis in the same way as in Example 21, the emitted light was found to have the luminescent peak at about 630 nm. In addition, the emitted light was found to have a luminance of 1000 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 600 hours for the element to decrease in luminance by half.

EXAMPLE 25

This example demonstrates the production of an organic electroluminescent element in which the electron transfer layer is made of a mixture of an aminostyryl compound of the above-mentioned structural formula (15)-2 and Alq$_3$. The former is one of the aminostyryl compounds represented by the above-mentioned general formula [I].

The organic electroluminescent element was identical with that of Example 22 in layer structure and method of film formation.

The organic electroluminescent element of Example 25 produced in this manner was examined for luminescent characteristics by applying a forward bias dc voltage in a nitrogen atmosphere. It emitted orange light. By spectral analysis in the same way as in Example 21, the emitted light was found to have the luminescent peak at about 590 nm. In addition, the emitted light was found to have a luminance of 1100 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 700 hours for the element to decrease in luminance by half.

EXAMPLE 26

This example demonstrates the production of an organic electroluminescent element in which the electron transfer layer is made of a mixture of an aminostyryl compound of the above-mentioned structural formula (15)-4 and Alq$_3$. The former is one of the aminostyryl compounds represented by the above-mentioned general formula [I].

The organic electroluminescent element was identical with that of Example 22 in layer structure and method of film formation.

The organic electroluminescent element of Example 26 produced in this manner was examined for luminescent characteristics by applying a forward bias dc voltage in a nitrogen atmosphere. It emitted red light. By spectral analysis in the same way as in Example 21, the emitted light was found to have the luminescent peak at about 610 nm. In addition, the emitted light was found to have a luminance of 1000 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 550 hours for the element to decrease in luminance by half.

EXAMPLE 27

This example demonstrates the production of an organic electroluminescent element in which the electron transfer layer is made of a mixture of an aminostyryl compound of the above-mentioned structural formula (15)-6 and $Alq_3$. The former is one of the aminostyryl compounds represented by the above-mentioned general formula [I].

The organic electroluminescent element was identical with that of Example 22 in layer structure and method of film formation.

The organic electroluminescent element of Example 27 produced in this manner was examined for luminescent characteristics by applying a forward bias dc voltage in a nitrogen atmosphere. It emitted orange light. By spectral analysis in the same way as in Example 21, the emitted light was found to have the luminescent peak at about 585 nm. In addition, the emitted light was found to have a luminance of 600 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 300 hours for the element to decrease in luminance by half.

EXAMPLE 28

This example demonstrates the production of an organic electroluminescent element in which the electron transfer layer is made of a mixture of an aminostyryl compound of the above-mentioned structural formula (15)-7 and $Alq_3$.

The organic electroluminescent element was identical with that of Example 22 in layer structure and method of film formation.

The organic electroluminescent element of Example 28 produced in this manner was examined for luminescent characteristics by applying a forward bias dc voltage in a nitrogen atmosphere. It emitted red light. By spectral analysis in the same way as in Example 21, the emitted light was found to have the luminescent peak at about 615 nm. In addition, the emitted light was found to have a luminance of 650 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 350 hours for the element to decrease in luminance by half.

EXAMPLE 29

This example demonstrates the production of an organic electroluminescent element in which the electron transfer layer is made of a mixture of an aminostyryl compound of the above-mentioned structural formula (15)-8 and $Alq_3$. The former is one of the aminostyryl compounds represented by the above-mentioned general formula [I].

The organic electroluminescent element was identical with that of Example 22 in layer structure and method of film formation.

The organic electroluminescent element of Example 29 produced in this manner was examined for luminescent characteristics by applying a forward bias dc voltage in a nitrogen atmosphere. It emitted red light. By spectral analysis in the same way as in Example 21, the emitted light was found to have the luminescent peak at about 610 nm. In addition, the emitted light was found to have a luminance of 500 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 200 hours for the element to decrease in luminance by half.

EXAMPLE 30

This example demonstrates the production of an organic electroluminescent element in which the electron transfer layer is made of a mixture of an aminostyryl compound of the above-mentioned structural formula (15)-9 and $Alq_3$. The former is one of the aminostyryl compounds represented by the above-mentioned general formula [I].

The organic electroluminescent element was identical with that of Example 22 in layer structure and method of film formation.

The organic electroluminescent element of Example 30 produced in this manner was examined for luminescent characteristics by applying a forward bias dc voltage in a nitrogen atmosphere It emitted red light. By spectral analysis in the same way as in Example 21, the emitted light was found to have the luminescent peak at about 640 nm. In addition, the emitted light was found to have a luminance of 920 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 480 hours for the element to decrease in luminance by half.

EXAMPLE 31

This example demonstrates the production of an organic electroluminescent element in which the electron transfer layer is made of a mixture of an aminostyryl compound of the above-mentioned structural formula (15)-l11 and $Alq_3$. The former is one of the aminostyryl compounds represented by the above-mentioned general formula [I].

The organic electroluminescent element was identical with that of Example 22 in layer structure and method of film formation.

The organic electroluminescent element of Example 31 produced in this manner was examined for luminescent characteristics by applying a forward bias dc voltage in a nitrogen atmosphere. It emitted orange light. By spectral analysis in the same way as in Example 21, the emitted light was found to have the luminescent peak at about 580 nm. In addition, the emitted light was found to have a luminance of 1100 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with

EXAMPLE 32

This example demonstrates the production of an organic electroluminescent element in which the electron transfer layer is made of a mixture of an aminostyryl compound of the above-mentioned structural formula (15)-12 and Alq$_3$. The former is one of the aminostyryl compounds represented by the above-mentioned general formula [I].

The organic electroluminescent element was identical with that of Example 22 in layer structure and method of film formation.

The organic electroluminescent element of Example 32 produced in this manner was examined for luminescent characteristics by applying a forward bias dc voltage in a nitrogen atmosphere. It emitted orange light. By spectral analysis in the same way as in Example 21, the emitted light was found to have the luminescent peak at about 600 nm. In addition, the emitted light was found to have a luminance of 900 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 660 hours for the element to decrease in luminance by half.

EXAMPLE 33

This example demonstrates the production of an organic electroluminescent element in which the electron transfer layer is made of a mixture of an aminostyryl compound of the above-mentioned structural formula (17)-1 and Alq$_3$. The former is one of the aminostyryl compounds represented by the above-mentioned general formula [I].

The organic electroluminescent element was identical with that of Example 22 in layer structure and method of film formation.

The organic electroluminescent element of Example 33 produced in this manner was examined for luminescent characteristics by applying a forward bias dc voltage in a nitrogen atmosphere. It emitted red light. By spectral analysis in the same way as in Example 21, the emitted light was found to have the luminescent peak at about 620 nm. In addition, the emitted light was found to have a luminance of 1650 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 880 hours for the element to decrease in luminance by half.

EXAMPLE 34

This example demonstrates the production of an organic electroluminescent element in which the electron transfer layer is made of a mixture of an aminostyryl compound of the above-mentioned structural formula (17)-2 and Alq$_3$. The former is one of the aminostyryl compounds represented by the above-mentioned general formula [I].

The organic electroluminescent element was identical with that of Example 22 in layer structure and method of film formation.

The organic electroluminescent element produced in this manner was examined for luminescent characteristics by applying a forward bias dc voltage in a nitrogen atmosphere. It emitted red light. By spectral analysis in the same way as in Example 21, the emitted light was found to have the luminescent peak at about 645 nm. In addition, the emitted light was found to have a luminance of 1300 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 800 hours for the element to decrease in luminance by half.

EXAMPLE 35

This example demonstrates the production of an organic electroluminescent element in which the electron transfer layer is made of a mixture of an aminostyryl compound of the above-mentioned structural formula (17)-3 and Alq$_3$. The former is one of the aminostyryl compounds represented by the above-mentioned general formula [I].

The organic electroluminescent element was identical with that of Example 22 in layer structure and method of film formation.

The organic electroluminescent element produced in this manner was examined for luminescent characteristics by applying a forward bias dc voltage in a nitrogen atmosphere. It emitted red light. By spectral analysis in the same way as in Example 21, the emitted light was found to have the luminescent peak at about 600 nm. In addition, the emitted light was found to have a luminance of 1450 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 700 hours for the element to decrease in luminance by half.

EXAMPLE 36

This example demonstrates the production of an organic electroluminescent element in which the electron transfer layer is made of a mixture of an aminostyryl compound of the above-mentioned structural formula (17)-4 and Alq$_3$. The former is one of the aminostyryl compounds represented by the above-mentioned general formula [I].

The organic electroluminescent element was identical with that of Example 22 in layer structure and method of film formation.

The organic electroluminescent element of Example 36 produced in this manner was examined for luminescent characteristics by applying a forward bias dc voltage in a nitrogen atmosphere. It emitted red light. By spectral analysis in the same way as in Example 21, the emitted light was found to have the luminescent peak at about 620 nm. In addition, the emitted light was found to have a luminance of 1200 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 650 hours for the element to decrease in luminance by half.

EXAMPLE 37

This example demonstrates the production of an organic electroluminescent element in which the electron transfer layer is made of a mixture of an aminostyryl compound of the above-mentioned structural formula (17)-5 and Alq₃. The former is one of the aminostyryl compounds represented by the above-mentioned general formula [I].

The organic electroluminescent element was identical with that of Example 22 in layer structure and method of film formation.

The organic electroluminescent element of Example 37 produced in this manner was examined for luminescent characteristics by applying a forward bias dc voltage in a nitrogen atmosphere. It emitted red light. By spectral analysis in the same way as in Example 21, the emitted light was found to have the luminescent peak at about 650 nm. In addition, the emitted light was found to have a luminance of 800 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 500 hours for the element to decrease in luminance by half.

EXAMPLE 38

This example demonstrates the production of an organic electroluminescent element in which the electron transfer layer is made of a mixture of an aminostyryl compound of the above-mentioned structural formula (15)-5 and Alq₃.

The organic electroluminescent element was identical with that of Example 22 in layer structure and method of film formation.

The organic electroluminescent element of Example 38 produced in this manner was examined for luminescent characteristics by applying a forward bias dc voltage in a nitrogen atmosphere. It emitted red light. By spectral analysis in the same way as in Example 21, the emitted light was found to have the luminescent peak at about 655 nm. In addition, the emitted light was found to have a luminance of 1720 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 780 hours for the element to decrease in luminance by half.

EXAMPLE 39

This example demonstrates the production of an organic electroluminescent element in which the hole transfer layer is made of a mixture of an aminostyryl compound of the above-mentioned structural formula (15)-3 and a-NPD and the electron transfer layer is made of a mixture of an aminostyryl compound of the above-mentioned structural formula (15)-3 and Alq₃. The former is one of the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate were deposited by vacuum deposition (at 10⁻⁴ Pa or less) the compound of the above-mentioned structural formula (15)-3 and a-NPD (as the hole transfer material). There was formed a 30-nm thick hole transfer layer (functioning also as a luminescent layer) consisting of the two components mixed in a ratio of 1:1 by weight. The rate of deposition was 0.1 nm/sec each.

Then, on the hole transfer layer (functioning also as a luminescent layer) was co-deposited by vacuum deposition a 1:1 mixture (by weight) of the compound of the above-mentioned structural formula (15)-3 and Alq₃ (as an electron transfer material). There was formed a 30-nm thick electron transfer layer (functioning also as a luminescent layer) composed of the above-mentioned two compounds. The rate of deposition was 0.2 nm/sec each.

Then, on the electron transfer layer (functioning also as a luminescent layer) was deposited by vacuum deposition vasocuproin of the above-mentioned structural formula as the hole blocking layer material. There was formed a 15-nm thick hole blocking layer. The rate of deposition was 0.1 nm/sec.

Then, on the hole blocking layer was deposited Alq₃ of the above-mentioned structural formula as the electron transfer material. There was formed a 30-nm thick electron transfer layer. The rate of deposition was 0.2 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element of Example 39 as shown FIG. 9.

The organic electroluminescent element of Example 39 produced in this manner was examined for luminescent characteristics by applying a forward bias dc voltage in a nitrogen atmosphere. It emitted red light. By spectral analysis with a spectroscope having a photodiode array as a detector (made by Otsuka Electronics Co., Ltd.), the emitted light was found to have the luminescent peak at about 635 nm. In addition, the emitted light was found to have a luminance of 2900 cd/m² at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m² was allowed to emit light continuously by application of constant current. It took 1100 hours for the element to decrease in luminance by half.

EXAMPLE 40

This example demonstrates the production of an organic electroluminescent element in which the hole transfer layer is made of an aminostyryl compound of the above-mentioned structural formula (15)-3 in the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered ,with a metal mask having a plurality of unit openings each measuring 2.0×2.0 mm. On the substrate was deposited by vacuum deposition (at $10^{-4}$ Pa or less) the aminostyryl compound of the above-mentioned structural formula (15)-3. There was formed a 50-nm thick hole transfer layer (functioning also as a luminescent layer). The rate of deposition was 0.1 nm/sec each.

Then, on the hole transfer layer was deposited by vacuum deposition vasocuproin of the above-mentioned structural formula as the hole blocking layer material. There was formed a 15-nm thick hole blocking layer. The rate of deposition was 0.1 nm/sec.

Then, on the hole blocking layer was deposited $Alq_3$ (tris(8-quinolinol)aluminum) of the above-mentioned structural formula as the electron transfer layer material. There was formed a 50-nm thick electron transfer layer. The rate of deposition was 0.2 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element of Example 40 as shown FIG. 7.

The organic electroluminescent element of Example 40 produced in this manner was examined for luminescent characteristics by applying a forward bias dc voltage in a nitrogen atmosphere. It emitted red light. By spectral analysis with a spectroscope having a photodiode array as a detector (made by Otsuka Electronics Co., Ltd.), the emitted light was found to have the luminescent peak at about 640 nm. In addition, the emitted light was found to have a luminance of 3000 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1100 hours for the element to decrease in luminance by half.

EXAMPLE 41

This example demonstrates the production of an organic electroluminescent element in which the luminescent layer capable of electron transfers made an aminostyryl compound of the above-mentioned structural formula (15)-3 in the aminostyryl compounds represented by the above-mentioned general formula [I].

First, the process was started by setting in a vacuum vapor deposition apparatus a glass substrate (30×30 mm) having a 100-nm thick anode of ITO formed on one side thereof. The substrate was covered with a metal mask having a plurality of unit openings each measuring 2.0×2.0 mm. On the substrate was deposited by vacuum deposition (at $10^{-4}$ Pa or less) a-NPD of the under-mentioned structural formula. There was formed a 30-nm thick layer. The rate of deposition was 0.1 nm/sec each.

Then, on the hole transfer layer was deposited by vacuum deposition the compound of the above-mentioned structural formula (15)-3. There was formed a 30-nm thick electron transfer layer (functioning also as a luminescent layer) of the compound of the above-mentioned structural formula (15)-3. The rate of deposition was 0.2 nm/sec.

Then, on the luminescent blocking layer was deposited vasocuproin of the above-mentioned structural formula as the hole blocking layer material. There was formed a 15-nm thick hole blocking layer. The rate of deposition was 0.1 nm/sec.

Then, on the hole blocking layer was deposited $Alq_3$ of the above-mentioned structural formula as the electron transfer layer material. There was formed a 30 nm thick electron transfer layer. The rate of deposition was 0.2 nm/sec.

The cathode (in laminate structure) was formed from Mg and Ag by vacuum deposition. The Mg film was 50 nm thick and the Ag film was 150 nm thick. The rate of deposition was 1 nm/sec. Thus there was obtained the organic electroluminescent element as shown FIG. 9.

The organic electroluminescent element of Example 41 produced in this manner was examined for luminescent characteristics by applying a forward bias dc voltage in a nitrogen atmosphere. It emitted red light. By spectral analysis in the same way as in Example 40, the emitted light was found to have the luminescent peak at about 640 nm. In addition, the emitted light was found to have a luminance of 3800 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1500 hours for the element to decrease in luminance by half.

EXAMPLE 42

This example demonstrates the production of an organic electroluminescent element in which the electron transfer layer is made of an aminostyryl compound of the above-mentioned structural formula (15)-2 in the aminostyryl compounds represented by the above-mentioned general formula [I].

The organic electroluminescent element was identical with that of Example 41 in layer structure and method of film formation.

The organic electroluminescent element produced in this manner was examined for luminescent characteristics by applying a forward bias dc voltage in a nitrogen atmosphere. It emitted orange light. By spectral analysis in the same way as in Example 40, the emitted light was found to have the luminescent peak at about 600 nm. In addition, the emitted light was found to have a luminance of 1200 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 800 hours for the element to decrease in luminance by half.

EXAMPLE 43

This example demonstrates the production of an organic electroluminescent element in which the electron transfer layer is made of an aminostyryl compound of the above-mentioned structural formula (15)-4 in the aminostyryl compounds represented by the above-mentioned general formula [I].

The organic electroluminescent element was identical with that of Example 41 in layer structure and method of film formation.

The organic electroluminescent element produced in this manner was examined for luminescent characteristics by applying a forward bias dc voltage in a nitrogen atmosphere. It emitted red light. By spectral analysis in the same way as in Example 40, the emitted light was found to have the luminescent peak at about 620 nm. In addition, the emitted light was found to have a luminance of 1100 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 600 hours for the element to decrease in luminance by half.

EXAMPLE 44

This example demonstrates the production of an organic electroluminescent element in which the electron transfer layer is made of a compound of the above-mentioned structural formula (15)-6 in the aminostyryl compounds represented by the above-mentioned general formula [I].

The organic electroluminescent element was identical with that of Example 41 in layer structure and method of film formation.

The organic electroluminescent element of Example 44 produced in this manner was examined for luminescent characteristics by applying a forward bias dc voltage in a nitrogen atmosphere. It emitted orange light. By spectral analysis in the same way as in Example 40, the emitted light was found to have the luminescent peak at about 595 nm. In addition, the emitted light was found to have a luminance of 700 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 300 hours for the element to decrease in luminance by half.

EXAMPLE 45

This example demonstrates the production of an organic electroluminescent element in which the electron transfer layer is made of an aminostyryl compound of the above-mentioned structural formula (15)-7 in the aminostyryl compounds represented by the above-mentioned general formula [I].

The organic electroluminescent element was identical with that of Example 41 in layer structure and method of film formation.

The organic electroluminescent element of Example 45 produced in this manner was examined for luminescent characteristics by applying a forward bias dc voltage in a nitrogen atmosphere. It emitted orange light. By spectral analysis in the same way as in Example 40, the emitted light was found to have the luminescent peak at about 620 nm. In addition, the emitted light was found to have a luminance of 750 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 450 hours for the element to decrease in luminance by half.

EXAMPLE 46

This example demonstrates the production of an organic electroluminescent element in which the electron transfer layer is made of an aminostyryl compound of the above-mentioned structural formula (15)-8 in the aminostyryl compounds represented by the above-mentioned general formula [I].

The organic electroluminescent element was identical with that of Example 41 in layer structure and method of film formation.

The organic electroluminescent element of Example 46 produced in this manner was examined for luminescent characteristics by applying a forward bias dc voltage in a nitrogen atmosphere. It emitted red light. By spectral analysis in the same way as in Example 40, the emitted light was found to have the luminescent peak at about 620 nm. In addition, the emitted light was found to have a luminance of 520 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 250 hours for the element to decrease in luminance by half.

EXAMPLE 47

This example demonstrates the production of an organic electroluminescent element in which the electron transfer layer is made of an aminostyryl compound of the above-mentioned structural formula (15)-9 in the aminostyryl compounds represented by the above-mentioned general formula [I].

The organic electroluminescent element was identical with that of Example 41 in layer structure and method of film formation.

The organic electroluminescent element of Example 47 produced in this manner was examined for luminescent characteristics by applying a forward bias dc voltage in a nitrogen atmosphere. It emitted red light. By spectral analysis in the same way as in Example 40, the emitted light was found to have the luminescent peak at about 650 nm. In addition, the emitted light was found to have a luminance of 1000 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 600 hours for the element to decrease in luminance by half.

EXAMPLE 48

This example demonstrates the production of an organic electroluminescent element in which the electron transfer layer is made of an aminostyryl compound of the above-mentioned structural formula (15)-11 in the aminostyryl compounds represented by the above-mentioned general formula [I].

The organic electroluminescent element was identical with that of Example 41 in layer structure and method of film formation.

The organic electroluminescent element of Example 48 produced in this manner was examined for luminescent characteristics by applying a forward bias dc voltage in a nitrogen atmosphere. It emitted orange light. By spectral analysis in the same way as in Example 40, the emitted light was found to have the luminescent peak at about 590 nm. In addition, the emitted light was found to have a luminance of 1200 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 850 hours for the element to decrease in luminance by half.

EXAMPLE 49

This example demonstrates the production of an organic electroluminescent element in which the electron transfer layer is made of an aminostyryl compound of the above-mentioned structural formula (15)-12 in the aminostyryl compounds represented by the above-mentioned general formula [I].

The organic electroluminescent element was identical with that of Example 41 in layer structure and method of film formation.

The organic electroluminescent element of Example 49 produced in this manner was examined for luminescent characteristics by applying a forward bias dc voltage in a nitrogen atmosphere. It emitted red light. By spectral analysis in the same way as in Example 40, the emitted light was found to have the luminescent peak at about 610 nm. In addition, the emitted light was found to have a luminance of 930 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 700 hours for the element to decrease in luminance by half.

EXAMPLE 50

This example demonstrates the production of an organic electroluminescent element in which the electron transfer layer is made of an aminostyryl compound of the above-mentioned structural formula (17)-1 in the aminostyryl compounds represented by the above-mentioned general formula [I].

The organic electroluminescent element was identical with that of Example 41 in layer structure and method of film formation.

The organic electroluminescent element produced in this manner was examined for luminescent characteristics by applying a forward bias dc voltage in a nitrogen atmosphere. It emitted red light. By spectral analysis in the same way as in Example 40, the emitted light was found to have the luminescent peak at about 630 nm. In addition, the emitted light was found to have a luminance of 1700 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 1000 hours for the element to decrease in luminance by half.

EXAMPLE 51

This example demonstrates the production of an organic electroluminescent element in which the electron transfer layer is made of a compound of the above-mentioned structural formula (17)-2 in the aminostyryl compounds represented by the above-mentioned general formula [I].

The organic electroluminescent element was identical with that of Example 41 in layer structure and method of film formation.

The organic electroluminescent element of Example 51 produced in this manner was examined for luminescent characteristics by applying a forward bias dc voltage in a nitrogen atmosphere. It emitted orange light. By spectral analysis in the same way as in Example 40, the emitted light was found to have the luminescent peak at about 655 nm. In addition, the emitted light was found to have a luminance of 1400 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 850 hours for the element to decrease in luminance by half.

EXAMPLE 52

This example demonstrates the production of an organic electroluminescent element in which the electron transfer layer is made of an aminostyryl compound of the above-mentioned structural formula (17)-3.

The organic electroluminescent element was identical with that of Example 41 in layer structure and method of film formation.

The organic electroluminescent element of Example 52 produced in this manner was examined for luminescent characteristics by applying a forward bias dc voltage in a nitrogen atmosphere. It emitted red light. By spectral analysis in the same way as in Example 40, the emitted light was found to have the luminescent peak at about 600 nm. In addition, the emitted light was found to have a luminance of 900 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 650 hours for the element to decrease in luminance by half.

EXAMPLE 53

This example demonstrates the production of an organic electroluminescent element in which the electron transfer layer is made of a compound of the above-mentioned structural formula (17)-4 in the aminostyryl compounds represented by the above-mentioned general formula [I].

The organic electroluminescent element was identical with that of Example 41 in layer structure and method of film formation.

The organic electroluminescent element produced in this manner was examined for luminescent characteristics by applying a forward bias dc voltage in a nitrogen atmosphere. It emitted red light. By spectral analysis in the same way as in Example 40, the emitted light was found to have the luminescent peak at about 630 nm. In addition, the emitted light was found to have a luminance of 1300 cd/m$^2$ at 8V according to the measurements of luminance at various voltages.

The organic electroluminescent element of Example 53 was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 750 hours for the element to decrease in luminance by half.

EXAMPLE 54

This example demonstrates the production of an organic electroluminescent element in which the electron transfer layer is made of a compound of the above-mentioned structural formula (17)-5 in the aminostyryl compounds represented by the above-mentioned general formula [I].

The organic electroluminescent element was identical with that of Example 41 in layer structure and method of film formation.

The organic electroluminescent element of Example 54 produced in this manner was examined for luminescent characteristics by applying a forward bias dc voltage in a nitrogen atmosphere. It emitted red light. By spectral analysis in the same way as in Example 40, the emitted light was found to have the luminescent peak at about 660 nm. In addition, the emitted light was found to have a luminance of 800 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 500 hours for the element to decrease in luminance by half.

EXAMPLE 55

This example demonstrates the production of an organic electroluminescent element in which the electron transfer layer is made of an aminostyryl compound of the above-mentioned structural formula (15)-5 in the aminostyryl compounds represented by the above-mentioned general formula [I].

The organic electroluminescent element was identical with that of Example 41 in layer structure and method of film formation.

The organic electroluminescent element of Example 55 produced in this manner was examined for luminescent characteristics by applying a forward bias dc voltage in a nitrogen atmosphere. It emitted red light. By spectral analysis in the same way as in Example 40, the emitted light was found to have the luminescent peak at about 660 nm. In addition, the emitted light was found to have a luminance of 1700 cd/m$^2$ at 8V according to the measurements of luminance at various voltages.

The organic electroluminescent element was allowed to stand for one month in a nitrogen atmosphere after it had been produced. It remained intact without any sign of deterioration. For accelerated deterioration, the element with an initial luminance of 200 cd/m$^2$ was allowed to emit light continuously by application of constant current. It took 900 hours for the element to decrease in luminance by half.

INDUSTRIAL APPLICABILITY

The organic electroluminescent element of the present invention is constructed such that an organic layer having a luminescent region is arranged between an anode and a cathode. The organic layer is composed of more than one layer, and at least one layer contains at least one species of aminostyryl compounds represented by the above-mentioned general formula [I] alone or in the form of a mixture. Therefore, the luminescent region can be formed from such a specific aminostyryl compound and/or a material capable of efficient energy transmission to it. Thus, the organic electroluminescent element has high fluorescence yields and good thermal stability, and emits red light with high color purity, high luminance, and high reliability.

In addition, the organic electroluminescent element has a hole blocking layer as mentioned above. This hole blocking layer promotes recombination of holes and electrons in the luminescent layer, although the organic electroluminescent element containing the above-mentioned aminostyryl compound inherently has high quantum yields. Thus the organic electroluminescent element emits light with high luminance and high efficiency.

What is claimed is:

1. An electroluminescent element comprising:
   (a) a cathode and an anode,
   (b) an organic layer disposed between the anode and the cathode, the organic layer comprising a luminescent organic material, the luminescent organic material comprising:
      (i) at least one aminostyryl compound selected from the group consisting of 15-2 to 15-12, 16-1 to 16-12, (15)-1

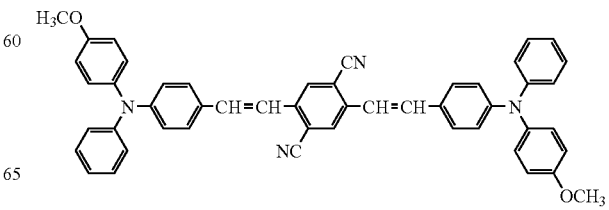

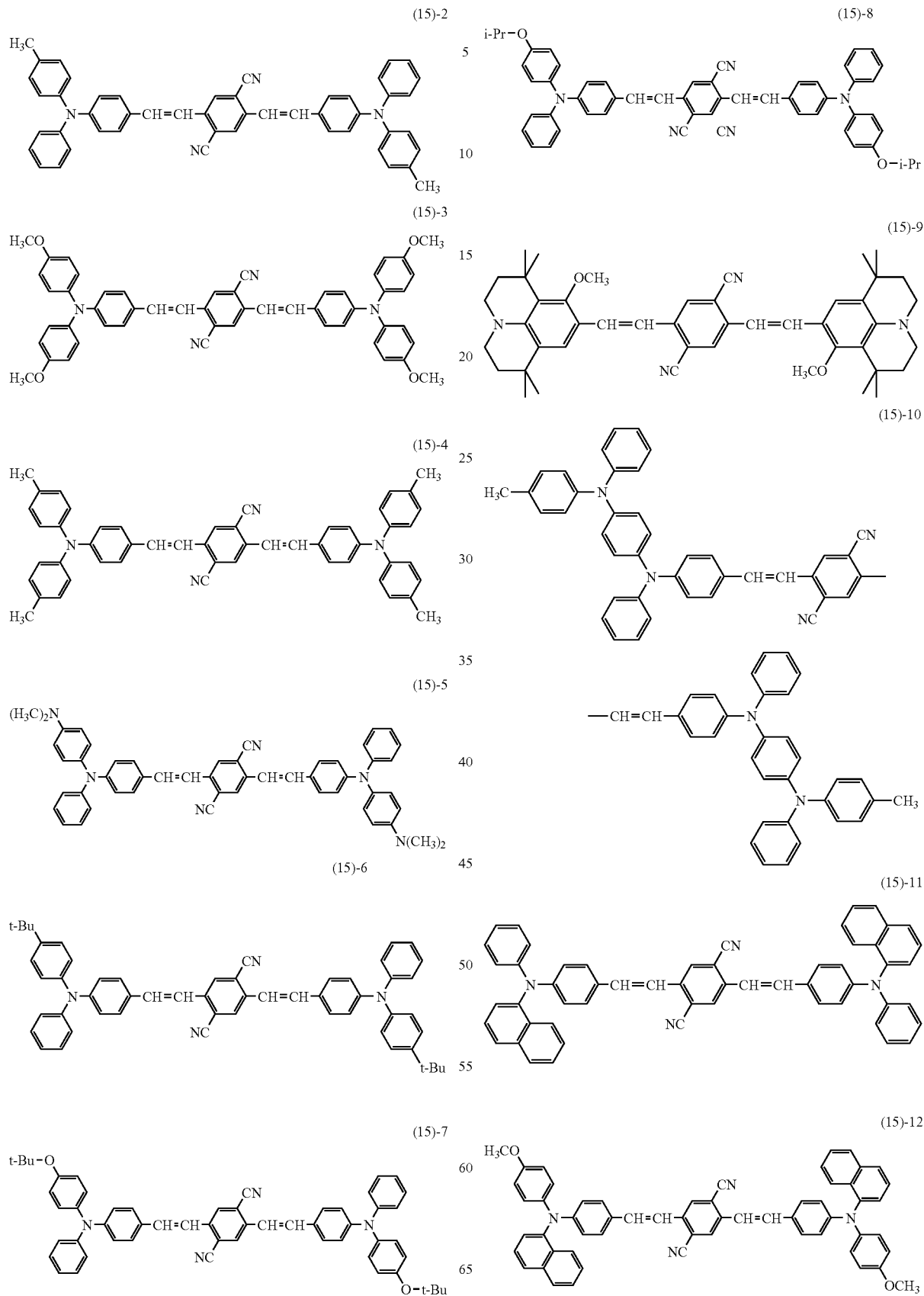

-continued
(16)-1
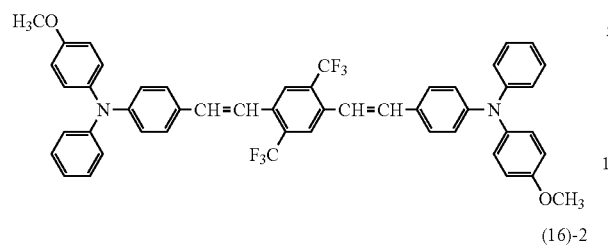
(16)-2
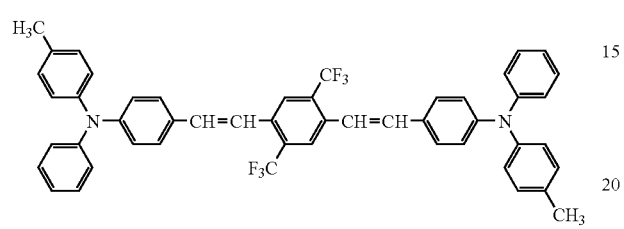
(16)-3
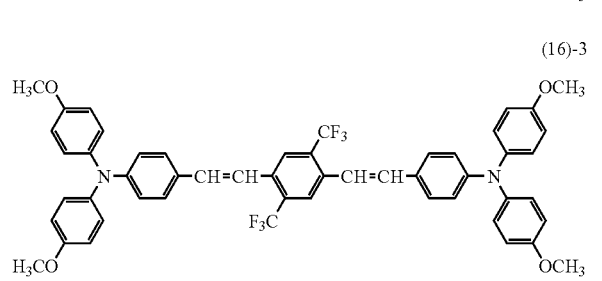
(16)-4
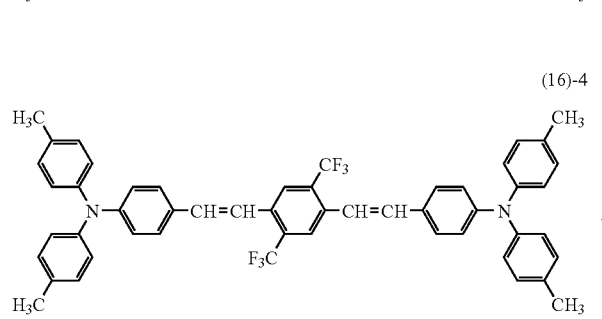
(16)-5
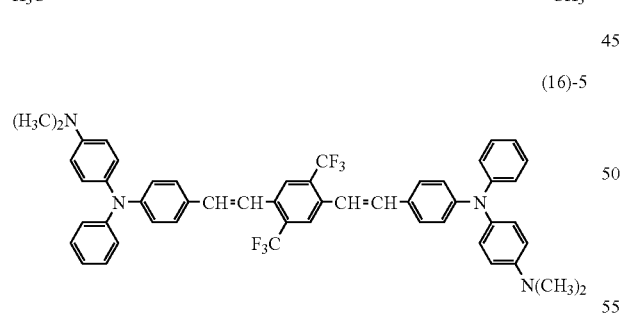
(16)-6
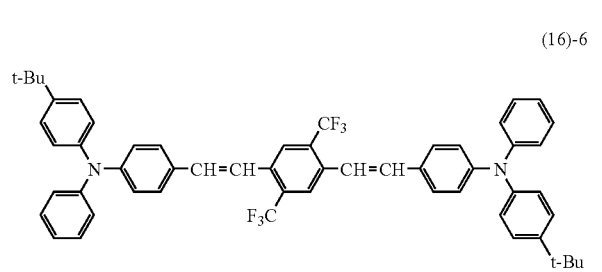
-continued
(16)-7
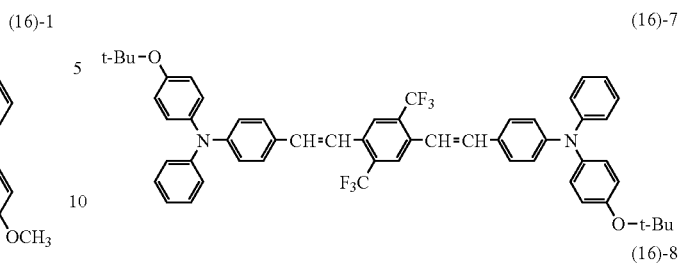
(16)-8
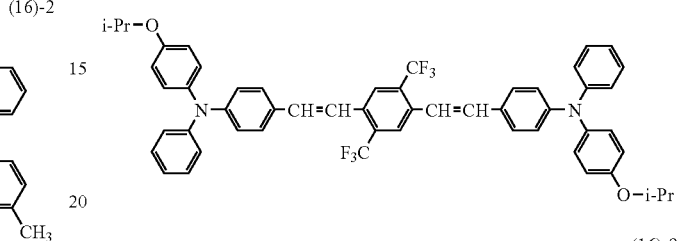
(16)-9
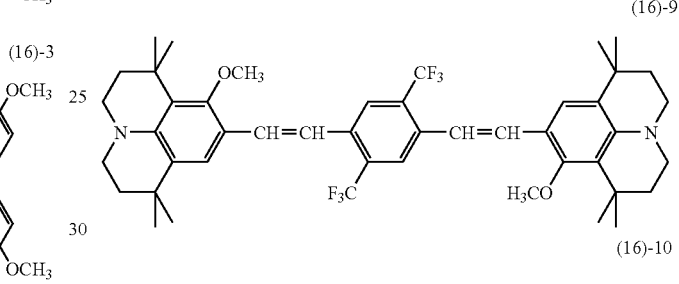
(16)-10
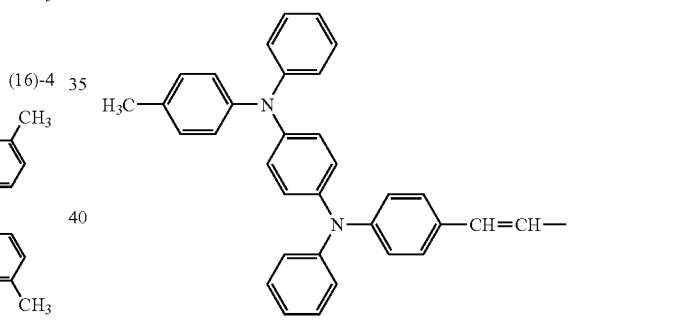
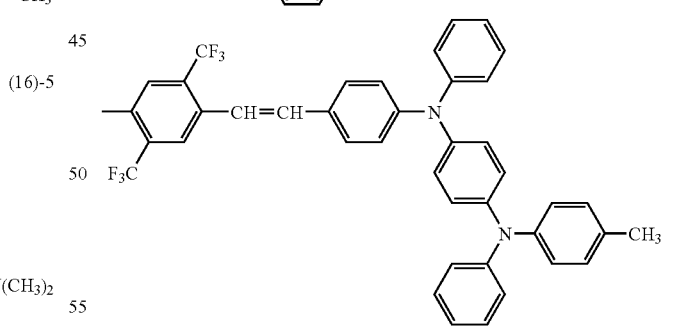
(16)-11
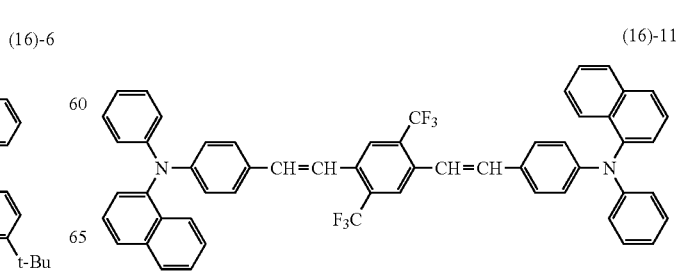

-continued
(16)-12
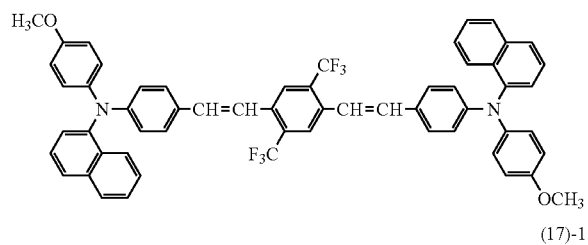
(17)-1
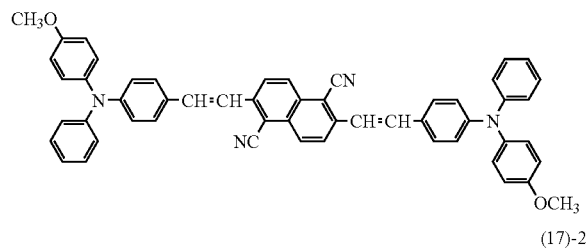
(17)-2
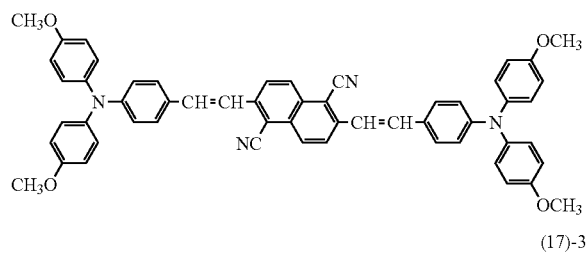
(17)-3
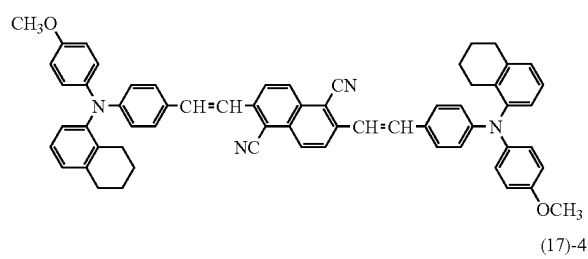
(17)-4
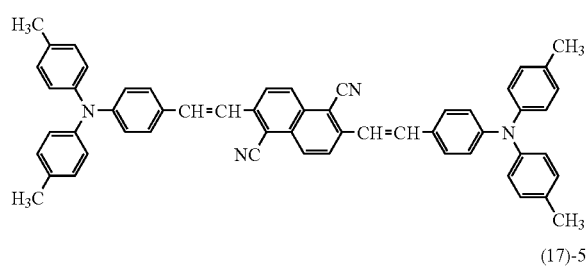
(17)-5
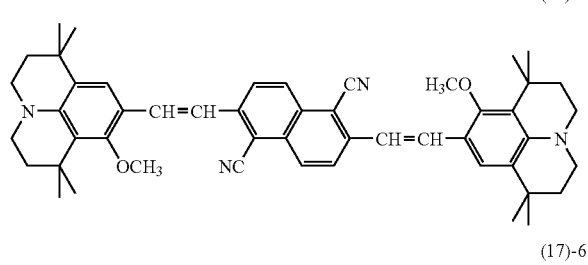
(17)-6
-continued
(18)-1
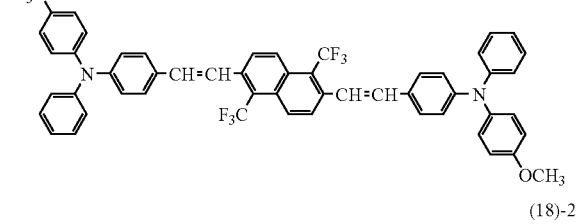
(18)-2
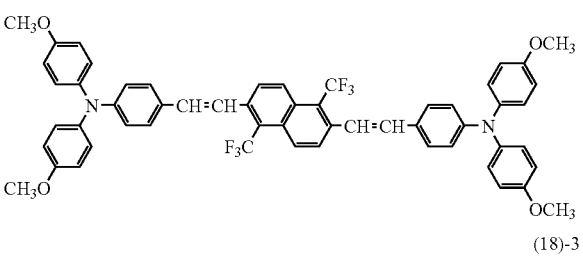
(18)-3
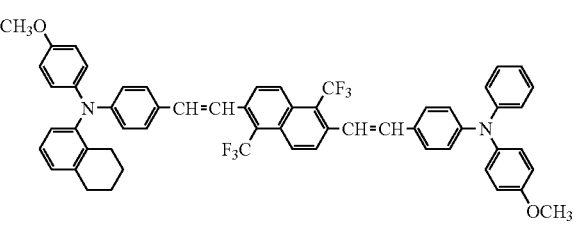
(18)-4
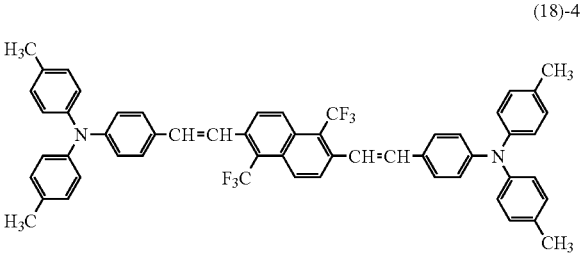
(18)-5
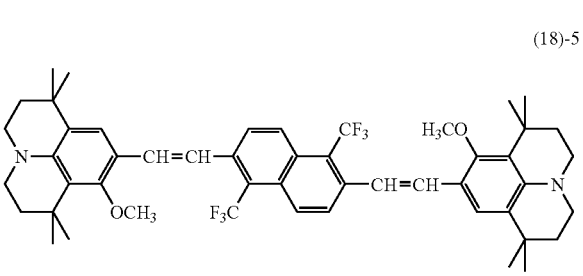
(18)-6
(ii) at least one compound selected from the group consisting of hole transport materials, electron transport materials, and dopants for red light emission
(c) a hole blocking layer disposed between the cathode and organic layer (b), wherein said hole blocking layer comprises one or more compounds of formula A

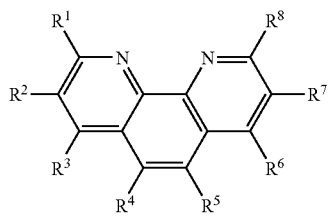

wherein $R^1$ to $R^8$ are independently selected from hydrogen, alkyl, aryl, amino, halogen, cyano and hydroxyl.

2. The electroluminescent element as defined in claim 1, wherein the organic layer is of organic multilayer structure composed of a hole transfer layer and an electron transfer layer, wherein the electron transfer layer in the organic multilayer structure comprises a light-emitting mixture, said light-emitting mixture containing at least one of said aminostyryl compounds.

3. The electroluminescent element as defined in claim 1, wherein the organic layer is of organic multilayer structure composed of a hole transfer layer and an electron transfer layer, wherein the hole transfer layer in the organic multilayer structure comprises a light-emitting mixture, said light-emitting mixture containing at least one species of the aminostyryl compounds.

4. The electroluminescent element as defined in claim 1, wherein the organic layer is of organic multilayer structure composed of a hole transfer layer and an electron transfer layer, wherein the hole transfer layer comprises a first light-emitting mixture, said light-emitting containing at least one of said aminostyryl compounds, and wherein the electron transfer layer comprises a second light-emitting mixture, said second light-emitting mixture containing at least one of said aminostyryl compounds the electroluminescent element further comprising a hole blocking layer between the cathode and the electron transfer layer.

5. The electroluminescent element as defined in claim 1, wherein the organic layer is of organic multilayer structure composed of a hole transfer layer, a luminescent layer, and an electron transfer layer, wherein the luminescent layer in the organic multilayer structure comprises a light-emitting mixture, said light-emitting mixture containing at least one of said aminostyryl compounds.

6. The electroluminescent element as defined in claim 1, wherein the organic layer is constructed such that said at least one layer therein is the layer of a light-emitting mixture containing at least one species of the aminostyryl compounds and a dye emitting red light which has the emission maximum in the range of 600 nm or more.

7. The electroluminescent element as defined in claim 6, wherein the organic layer comprises a hole transfer layer and an electron transfer layer.

8. The electroluminescent element as defined in claim 1, wherein the organic layer is of organic multilayer structure composed of a hole transfer layer and an electron transfer layer, wherein the hole transfer layer comprises a first light-emitting mixture, wherein said light-emitting mixture contains at least one of said aminostyryl compounds and a dye emitting red light with the emission maximum at a wavelength of at least 600 nm, and wherein the electron transfer comprises a second light-emitting mixture, said second light-emitting mixture containing at least of said aminostyryl compounds and a dye emitting red light with the emission maximum at a frequency of at least 600 nm or more, the electroluminescent element further comprising a hole blocking layer between the cathode and the electron transfer layer.

9. The electroluminescent element as defined in claim 1, wherein the organic layer is of organic multilayer structure composed of a hole transfer layer, a luminescent layer, and an electron transfer layer, wherein the luminescent layer comprises a light-emitting mixture containing at least one of said aminostyryl compounds and a dye emitting red light with the emission maximum at a wavelength of at least 600 nm or more.

10. An electroluminescent element comprising:
(a) a cathode and an anode,
(b) an organic layer disposed between the anode and the cathode, the organic layer comprising a luminescent organic material comprising at least one distyryl compound selected from the group consisting of 15-2 to 15-12, 16-1 to 16-12,

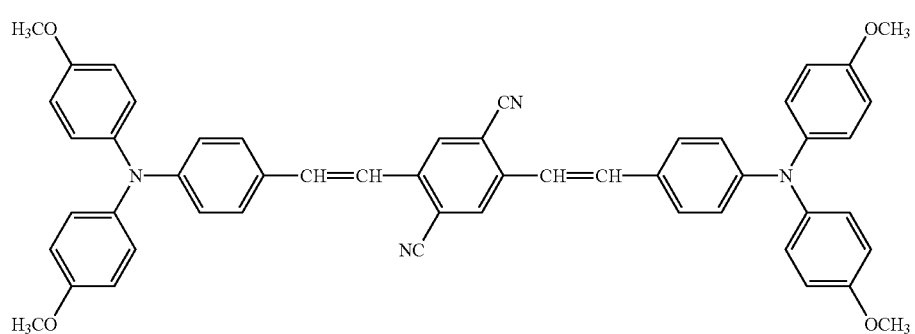
(15)-3
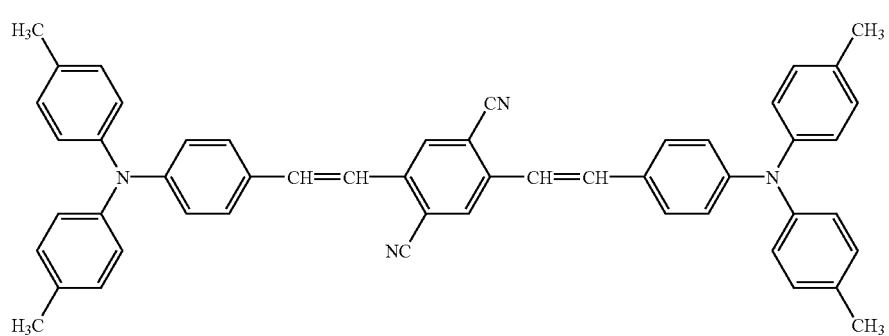
(15)-4
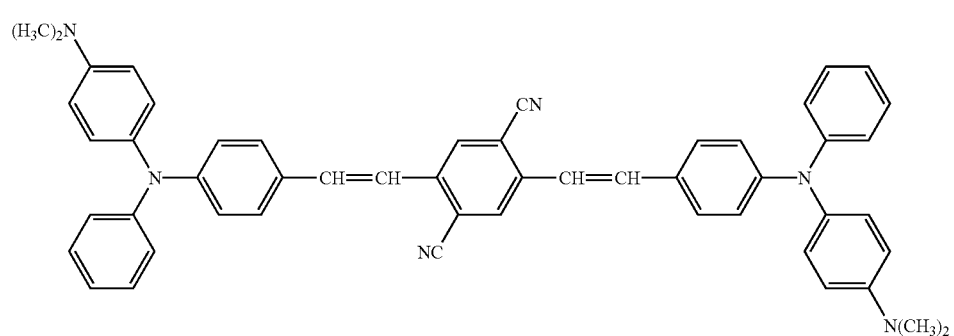
(15)-5
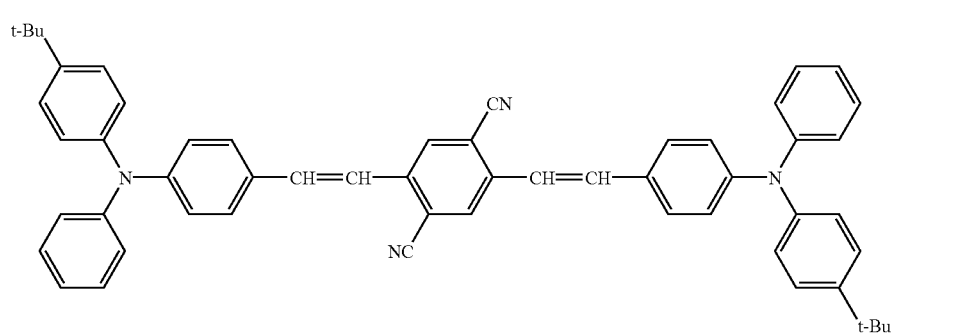
(15)-6
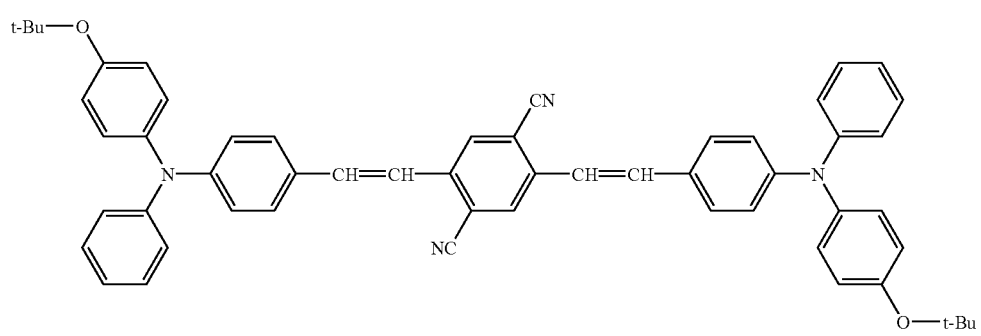
(15)-7

-continued
(15)-8
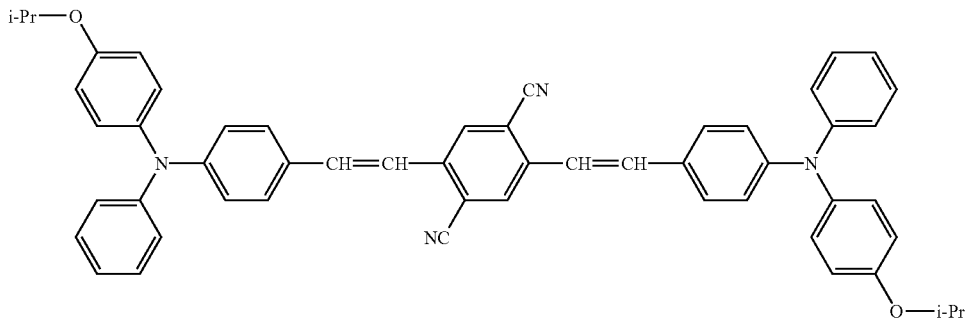
(15)-9
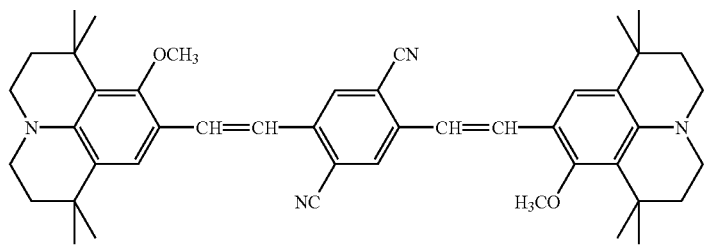
(15)-10
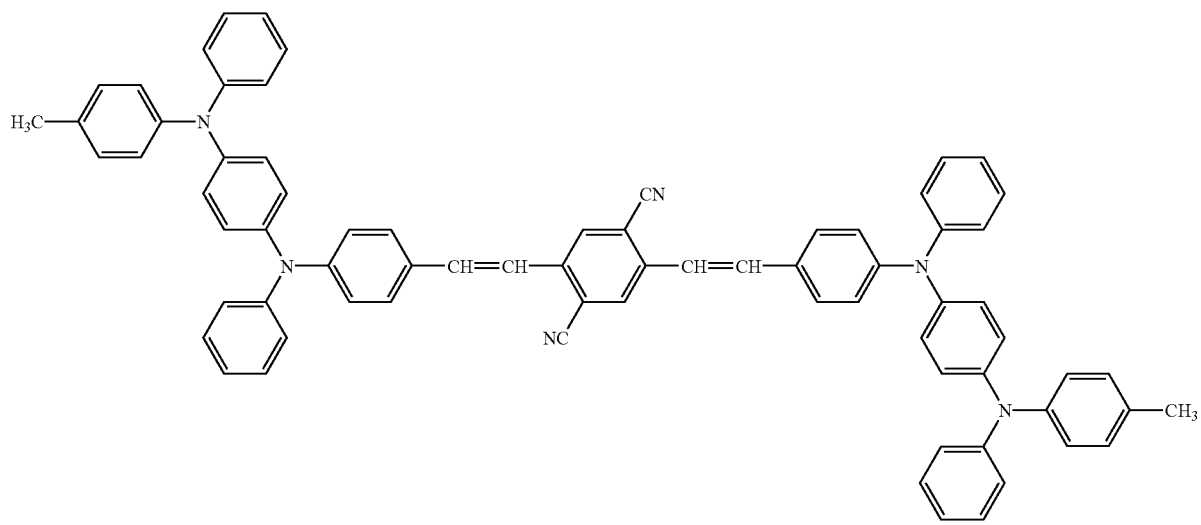
(15)-11
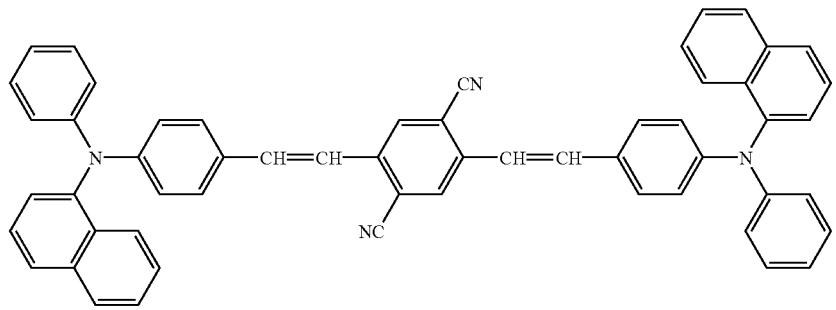

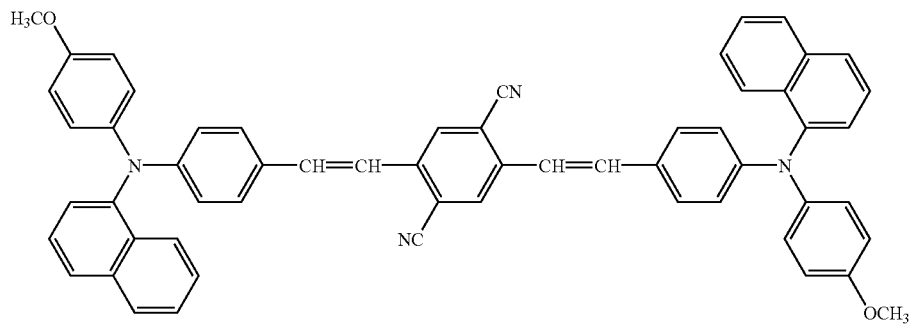
(15)-12
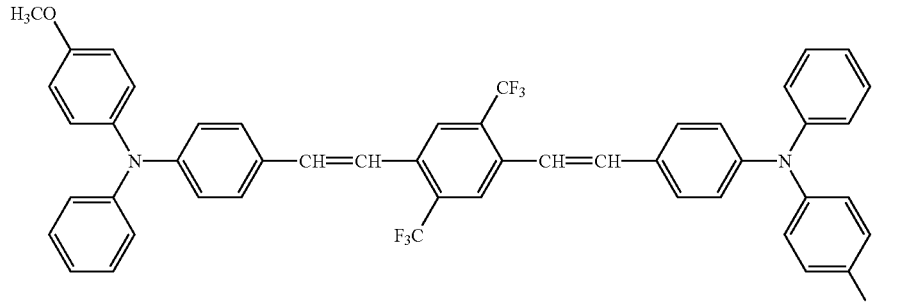
(16)-1
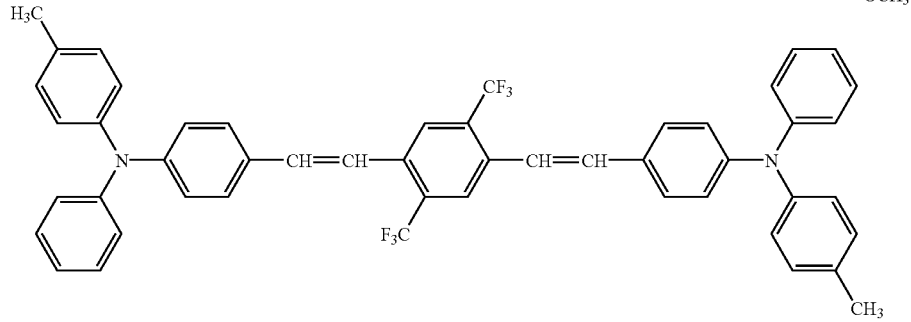
(16)-2
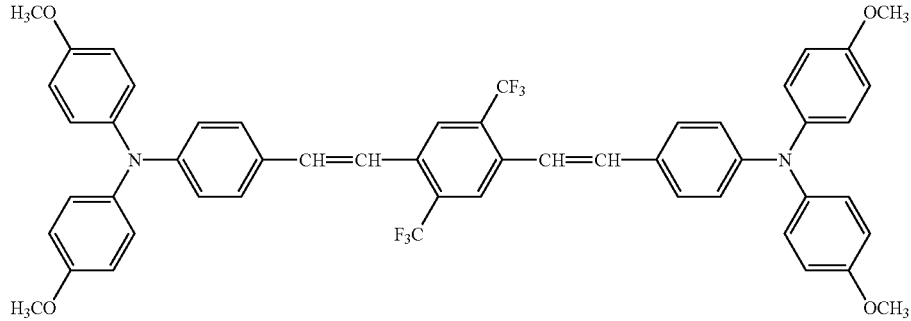
(16)-3
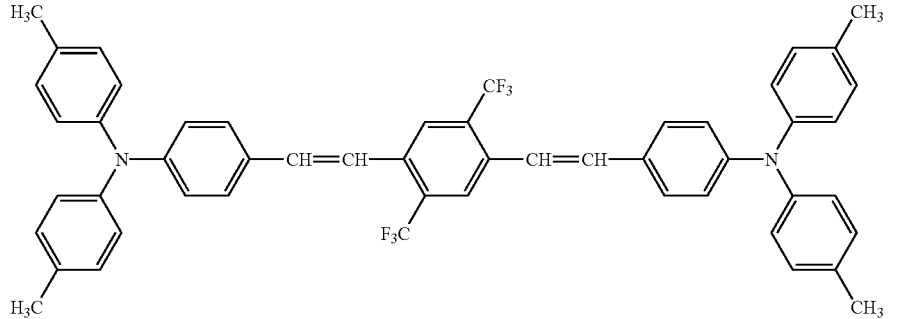
(16)-4

-continued
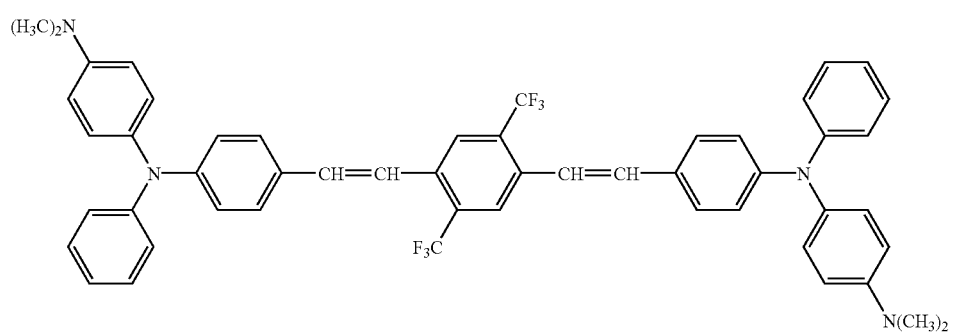
(16)-5
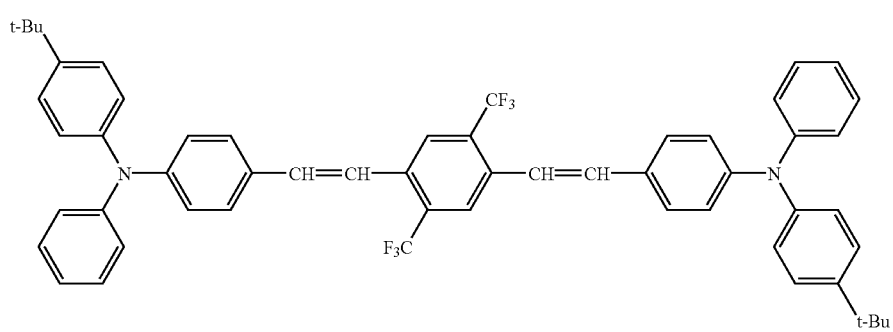
(16)-6
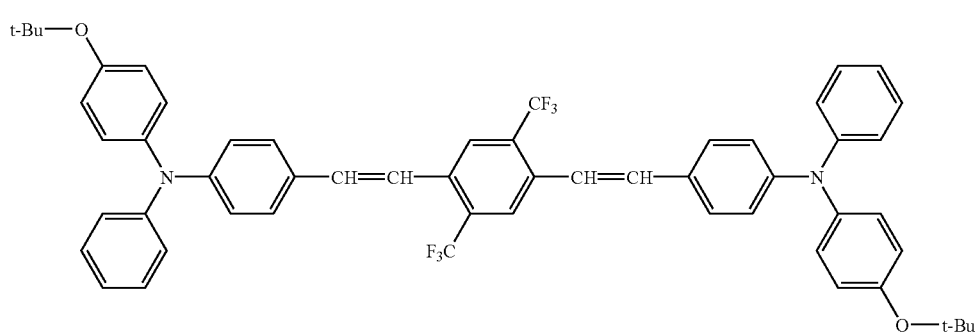
(16)-7
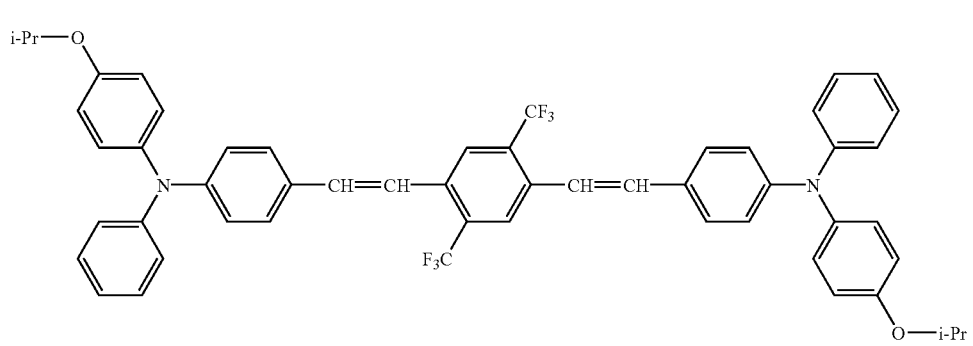
(16)-8
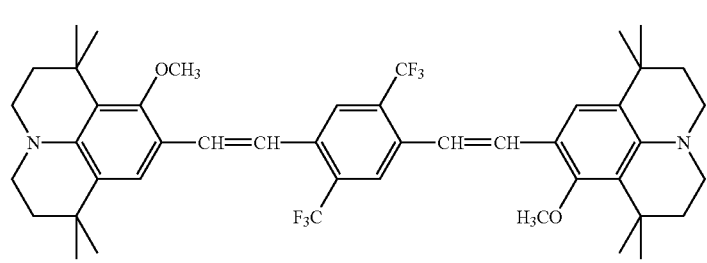
(16)-9

-continued
(16)-10
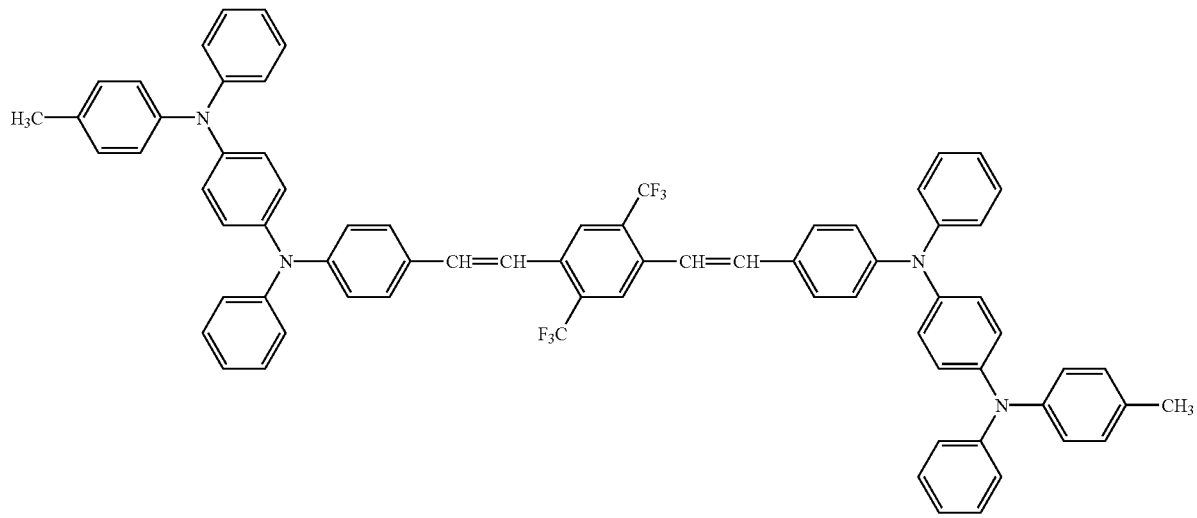
(16)-11
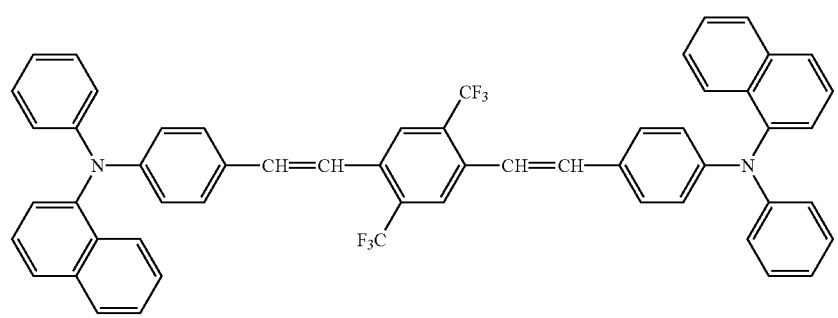
(16)-12
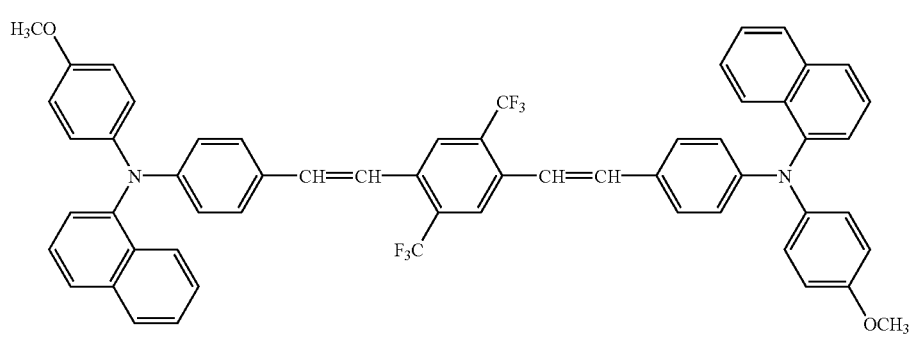
(17)-1
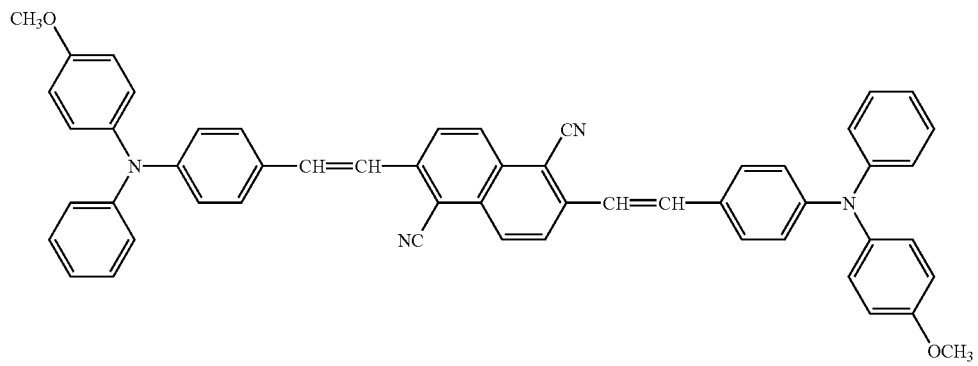

-continued
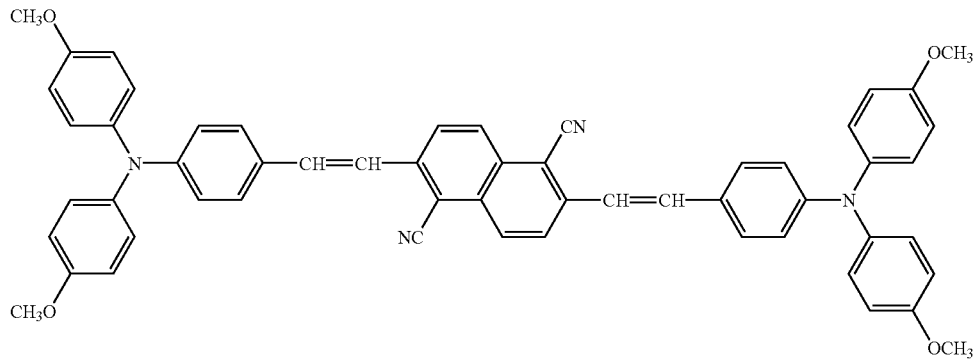
(17)-2
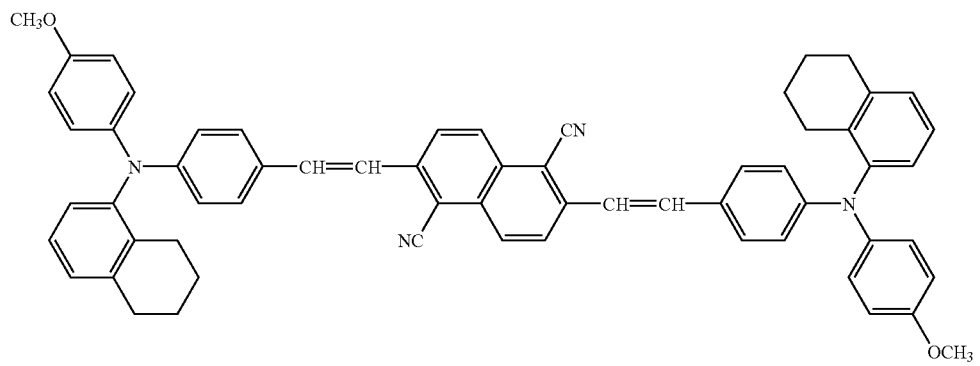
(17)-3
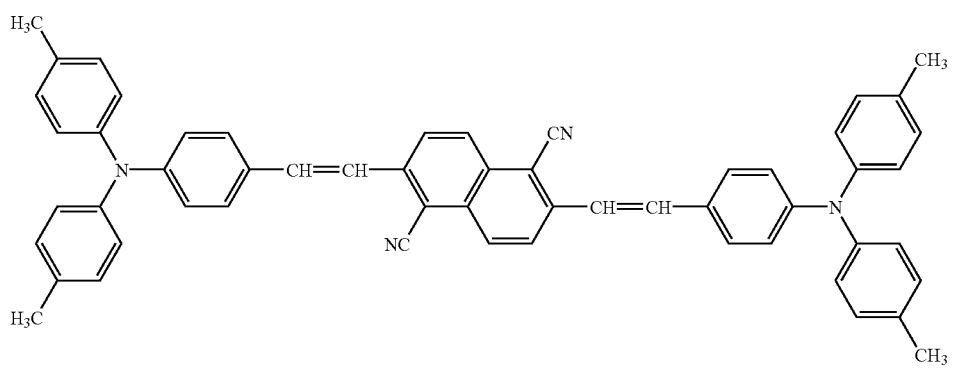
(17)-4
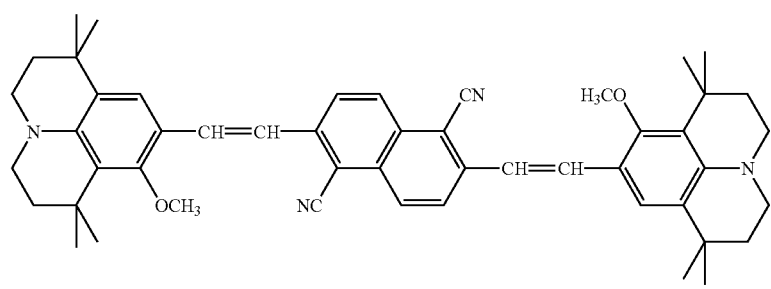
(17)-5
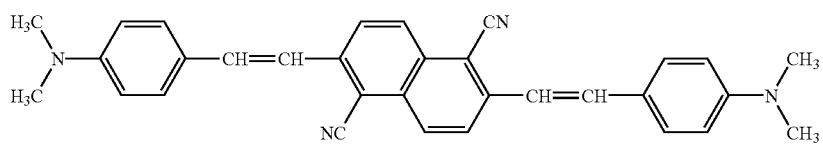
(17)-6

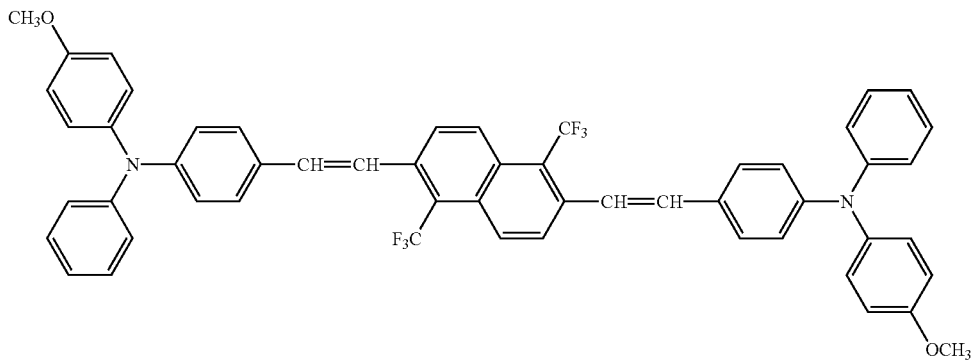
(18)-1
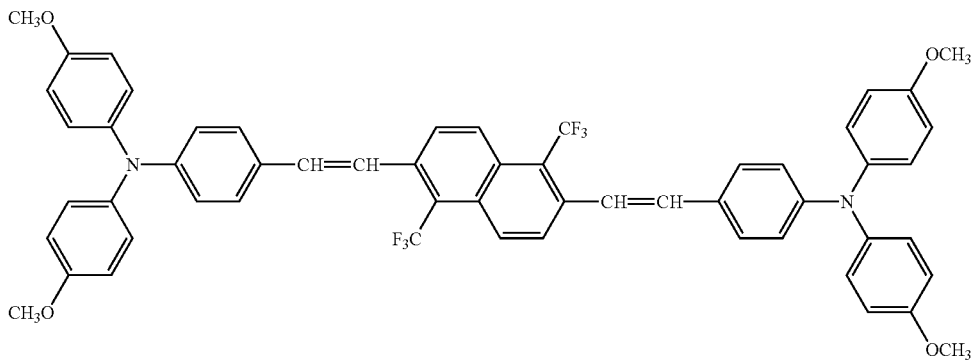
(18)-2
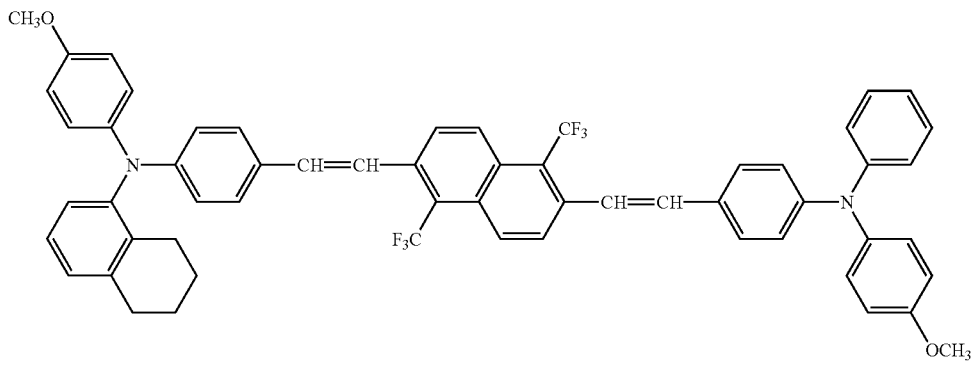
(18)-3
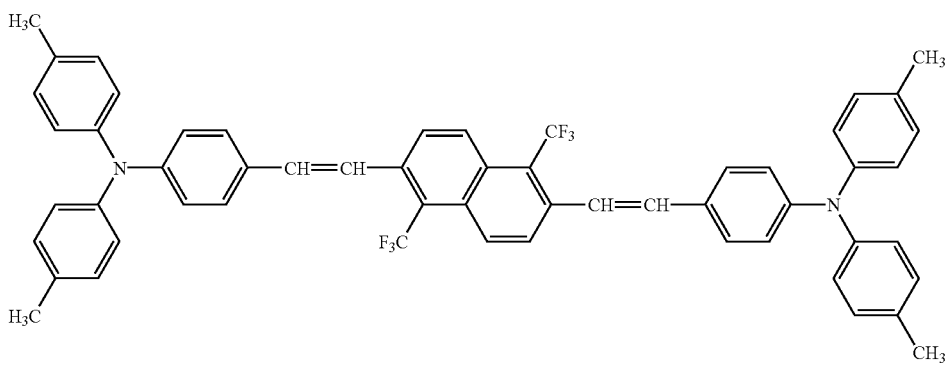
(18)-4

-continued

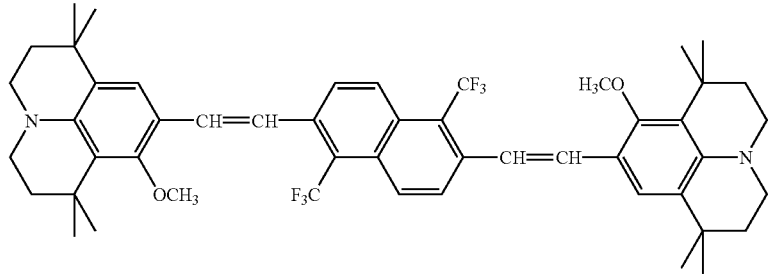
(18)-5

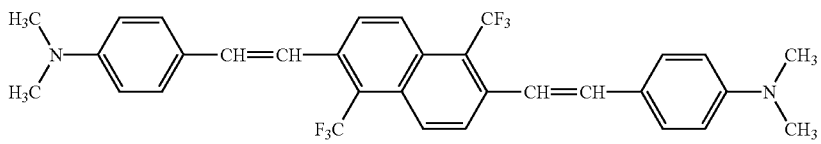
(18)-6

(c) a hole blocking layer disposed between the cathode and organic layer (b) wherein said hole blocking layer comprises one or more compounds of formula A

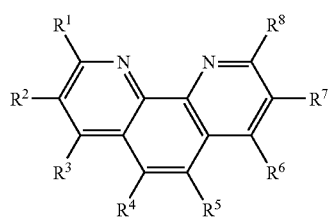
A wherein $R^1$ to $R^8$ are independently selected from hydrogen, alkyl, aryl, amino, halogen, cyano and hydroxyl.

11. The electroluminescent element as defined in claim 10, wherein the organic layer is of organic multilayer structure composed of a hole transfer layer and an electron transfer layer, wherein the electron transfer layer in the organic multilayer structure comprises said aminostyryl compound.

12. The electroluminescent element as defined in claim 10, wherein the organic layer is of organic multilayer structure composed of a hole transfer layer and an electron transfer layer, wherein the hole transfer layer in the organic multilayer structure comprises said aminostyryl compound.

13. The electroluminescent element as defined in claim 10, wherein the organic layer is of organic multilayer structure composed of a hole transfer layer and an electron transfer layer, wherein the hole transfer layer comprises said aminostyryl compound, and wherein the electron transfer layer comprises said aminostyryl compound, the electroluminescent layer further comprising a hole blocking layer between the cathode and the electron transfer layer.

14. The electroluminescent element as defined in claim 10, wherein the organic layer is of organic multilayer structure composed of a hole transfer layer, a luminescent layer, and an electron transfer layer, wherein the luminescent layer comprises said aminostyryl compound.

15. The electroluminescent element according to claim 1, wherein said hole transfer material is an aromatic amine.

16. The electroluminescent element according to claim 1 wherein said electron transfer material is selected from the group consisting of Alq3 and pyrazoline.

17. The electroluminescent element according to claim 1 wherein said dopant for red light emission is selected from the group consisting of DCM, DCM analog compounds, porphyrins, phthalocyanines, perylene compounds, Nile red, and squarilium compounds.

* * * * *